US005646156A

United States Patent [19]
Jacobson et al.

[11] Patent Number: 5,646,156
[45] Date of Patent: Jul. 8, 1997

[54] INHIBITION OF EOSINOPHIL ACTIVATION THROUGH A3 ADENOSINE RECEPTOR ANTAGONISM

[75] Inventors: Marlene A. Jacobson, Elkins Park; Robert G. Johnson, Rosemont; Christopher A. Salvatore, North Wales, all of Pa.

[73] Assignee: Merck & Co., Inc., Rahway, N.J.

[21] Appl. No.: 233,009

[22] Filed: Apr. 25, 1994

[51] Int. Cl.$^6$ ................................. A61K 31/52
[52] U.S. Cl. ............... 514/263; 514/826; 514/861; 514/863; 514/870; 514/886
[58] Field of Search ................ 514/263, 265, 514/826, 861, 863, 870, 886

[56] References Cited

U.S. PATENT DOCUMENTS

| | | | |
|---|---|---|---|
| 4,722,929 | 2/1988 | Austel et al. | 514/303 |
| 4,883,801 | 11/1989 | Nathanson | 514/263 |
| 5,021,574 | 6/1991 | Hajos et al. | 544/276 |

FOREIGN PATENT DOCUMENTS

| | | |
|---|---|---|
| 724173 | 12/1965 | Canada . |
| 0184738 | 6/1986 | European Pat. Off. . |
| 0203721 | 12/1986 | European Pat. Off. . |
| 0299209A2 | 1/1989 | European Pat. Off. . |
| 0379979A1 | 8/1990 | European Pat. Off. . |
| 0389282A2 | 9/1990 | European Pat. Off. . |
| 0399731A1 | 11/1990 | European Pat. Off. . |
| 0402087A2 | 12/1990 | European Pat. Off. . |
| 0415886A2 | 3/1991 | European Pat. Off. . |
| 0456204A2 | 11/1991 | European Pat. Off. . |
| 0480659A2 | 4/1992 | European Pat. Off. . |
| 0497258A2 | 8/1992 | European Pat. Off. . |
| 0503838A2 | 9/1992 | European Pat. Off. . |
| 0540766A1 | 5/1993 | European Pat. Off. . |
| 63-246739 | 4/1987 | Japan . |
| 64-22894 | 7/1987 | Japan . |
| 256428 | 8/1988 | Japan . |
| 313934 | 6/1989 | Japan . |
| 313940 | 6/1989 | Japan . |
| 467140 | 7/1989 | Japan . |
| 2264948 | 9/1993 | United Kingdom . |
| WO88/05775 | 8/1988 | WIPO . |
| WO90/00056 | 1/1990 | WIPO . |
| WO91/01730 | 2/1991 | WIPO . |
| WO91/07945 | 6/1991 | WIPO . |
| WO91/08741 | 6/1991 | WIPO . |
| WO92/05175 | 4/1992 | WIPO . |
| WO92/05176 | 4/1992 | WIPO . |
| WO92/11260 | 7/1992 | WIPO . |
| WO93/19747 | 10/1993 | WIPO . |
| WO93/22328 | 11/1993 | WIPO . |
| WO93/25677 | 12/1993 | WIPO . |
| WO94/02605 | 2/1994 | WIPO . |
| WO94/03173 | 2/1994 | WIPO . |
| WO94/03456 | 2/1994 | WIPO . |

OTHER PUBLICATIONS

J. Linden et al., Molecular Pharmacology, 44: pp. 524–532 (1993).
W. Meyerhof et al., Federation of European Biochemical Soc. 284, No. 2, pp. 155–160 (Jun. 1991).
F. Libert et al., Biochemical and Biophysical Res. Comm., 187, No. 2 pp. 919–926 (Sep. 16, 1992).
V. Ramkumar et al., J. of Biolocial Chem., 286, No. 23 pp. 16887–16890 (1993).
H. Goldner et al., Abstract 16273, 38–Heterocyclic Compounds, 62 (1965).
H. Goldner et al., Chemical Abstract 19611–19614, 64 (1966).
F. Bergmann et al., Chemical Abstract 3480–3482, 56, (1962).
H.C. Koppel et al., Chemical Abstract 6747–6748, 54 (1959).
H. C. Koppel et al., Chemical Abstract 18426–18428, 52, (1958).
I. I. Popv et al., Khim. Geterotsikl Soedin., 9, p. 1275 (1991).
G. Zvilichovsky et al., J. Heterocycl. Chem., 19(1) pp. 205–209 (1982).
F. Bergmann et al., Biochim. Biophys. Acta, 484(2), pp. 275–289 (1977).
F. Yoneda et al., Heterocycles, 4(11), pp. 1759–1764 (1976).
F. Yoneda et al., J. Chem. Soc., Perkin Trans. 1(14), pp. 1547–1550, 1976).
F. Bergmann et al., J. Chem. Soc. C, (13) pp. 1254–1260 (1967).
S.–C. J. Fu et al., J. Heterocycl. Chem., 3(4), pp. 476–481 (1966).
F. Libert, et al., Science, 244, pp. 569–572 (1989).
M. F. Jarvis, et al., J. Pharma, Exp. Therap., 251, pp. 888–893 (1989).
K. A. Jacobson, et al., J. Med. Chem. 32, pp. 1043–1051 (1989).
R. F. Burns, et al., Proc. Natl. Acad. Sci, USA, 80, pp. 2077–2080 (1983.
T. J. Furlong et al., Molecular Brain Research, 15, pp. 62–66 (1992).
K. D. Pierce et al., Biochem. & Biophysical Res. Comm., 187, No. 1, pp. 86–93 (Aug. 31, 1992).
Q.–Y. Zhou et al., Proc. Natl. Acad. Sci., 89, pp. 7432–7436 (Aug. 1992).
H. Nakata, J. Biol. Chem., 264, No. 28 pp. 16545–16551, (1989).
J. S. Fink et al., Molecular Brain Res., 14, pp. 186–195 (1992).

(List continued on next page.)

*Primary Examiner*—Kimberly Jordan
*Attorney, Agent, or Firm*—Richard S. Parr; Melvin Winokur

[57] ABSTRACT

The invention concerns the identification on eosinophils of the A3 adenosine receptor subtype and the blockade of said receptor in order to achieve inhibition of eosinophil activation and degranulation.

6 Claims, 24 Drawing Sheets

OTHER PUBLICATIONS

H. L. Tiffany & P.M. Murphy Gen Bank Accession M97370 (1992).

Y. Chern et al., Biochem. & Biophys. Res. Comm. 185, No. 1, pp. 304–309 (May 29, 1992).

M. E. Olah et al., J. Biological Chem., 267, No. 15 pp. 10765–10770 (1992).

J. H. Stehle et al., Molecular Endocrinology, 6, No. 3, pp. 384–392 (Mar. 1992).

A. L. Tucker et al., FEBS 297 No. 1.2, pp. 107–111 (Feb. 1992).

S. M. Reppert et al., Molecular Endocrinology, 5, pp. 1037–1048 (1991).

L. C. Mahan et al., Molecular Pharm. 40, pp. 1–7 (1991).

C. Maenhaut et al., Biochem. & Biophys. Res. Comm. 173, No. 3, pp. 1169–1178 (Nov. 31, 1990).

F. Libert et al., EMBO J., 10, pp. 1677–1682 (1991).

R. F. Bruns, et al. Molecular Pharm., 29, pp. 331–346 (1986).

F.G. Sajjadi and G.S. Firestein, B.B.A. 1179, pp. 105–107 (1993).

H. Kita et al., J. of Immuno., 146, No. 8, 2712–2718 (1991).

M. Cushley, et al., Am Rev Respir Dis, 129:380–384 (1984).

T. Björck, et al., Am Rev Respir Dis, 145:1087–1091 (1992).

M. Castañón, et al., Biochem. & Ciophys. Res. Comm., 198 No. 2., 626–631 (1994).

Salvatore, et al., P.N.A.S. USA, 90, 160365–106369 (Nov. 1993).

```
                           10                                    20
Met Pro Pro Ser Ile Ser Ala Phe Gln Ala Ala Tyr Ile Gly Ile Glu Val Leu Ile Ala
                     30                                    40
Leu Val Ser Val Pro Gly Asn Val Leu Val Ile Trp Ala Val Lys Val Asn Gln Ala Leu
                     50                                    60
Arg Asp Ala Thr Phe Cys Phe Ile Val Ser Leu Ala Val Ala Asp Val Ala Val Gly Ala
                     70                                    80
Leu Val Ile Pro Leu Ala Ile Leu Ile Asn Ile Gly Pro Gln Thr Tyr Phe His Thr Cys
                     90                                   100
Leu Met Val Ala Cys Pro Val Leu Ile Leu Thr Gln Ser Ser Ile Leu Ala Leu Leu Ala
                    110                                   120
Ile Ala Val Asp Arg Tyr Leu Arg Val Lys Ile Pro Leu Arg Tyr Lys Met Val Val Thr
                    130                                   140
Pro Arg Arg Ala Ala Val Ala Ile Ala Gly Cys Trp Ile Leu Ser Phe Val Val Gly Leu
                          150                                   160
Thr Pro Met Phe Gly Trp Asn Asn Leu Ser Ala Val Glu Arg Ala Trp Ala Ala Asn Gly
                    170                                   180
Ser Met Gly Glu Pro Val Ile Lys Cys Glu Phe Glu Lys Val Ile Ser Met Glu Tyr Met
                    190                                   200
Val Tyr Phe Asn Phe Phe Val Trp Val Leu Pro Pro Leu Leu Leu Met Val Leu Ile Tyr
                    210                                   220
Leu Glu Val Phe Tyr Leu Ile Arg Lys Gln Leu Asn Lys Lys Val Ser Ala Ser Ser Gly
                    230                                   240
Asp Pro Gln Lys Tyr Tyr Gly Lys Glu Leu Lys Ile Ala Lys Ser Leu Ala Leu Ile Leu
                    250                                   260
Phe Leu Phe Ala Leu Ser Trp Leu Pro Leu His Ile Leu Asn Cys Ile Thr Leu Phe Cys
                    270                                   280
Pro Ser Cys His Lys Pro Ser Ile Leu Thr Tyr Ile Ala Ile Phe Leu Thr His Gly Asn
                    290                                   300
Ser Ala Met Asn Pro Ile Val Tyr Ala Phe Arg Ile Gln Lys Phe Arg Val Thr Phe Leu
                    310                                   320
Lys Ile Trp Asn Asp His Phe Arg Cys Gln Pro Ala Pro Pro Ile Asp Glu Asp Leu Pro
                       326
Glu Glu Arg Pro Asp Asp
```

FIG.1

```
        10                      30                      50
atgccgccct ccatctcagc tttccaggcc gcctacatcg gcatcgaggt gctcatcgcc
        70                      90                     110
ctggtctctg tgcccgggaa cgtgctggtg atctgggcgg tgaaggtgaa ccaggcgctg
       130                     150                     170
cgggatgcca ccttctgctt catcgtgtcg ctggcggtgg ctgatgtggc cgtgggtgcc
       190                     210                     230
ctggtcatcc ccctcgccat cctcatcaac attgggccac agacctactt ccacacctgc
       250                     270                     290
ctcatggttg cctgtccggt cctcatcctc acccagagct ccatcctggc cctgctggca
       310                     330                     350
attgctgtgg accgctacct ccgggtcaag atccctctcc ggtacaagat ggtggtgacc
       370                     390                     410
ccccggaggg cggcggtggc catagccggc tgctggatcc tctccttcgt ggtgggactg
       430                     450                     470
accccttatgt ttggctggaa caatctgagt gcggtggagc gggcctgggc agccaacggc
       490                     510                     530
agcatggggg agcccgtgat caagtgcgag ttcgagaagg tcatcagcat ggagtacatg
       550                     570                     590
gtctacttca acttctttgt gtgggtgctg ccccgcttc tcctcatggt cctcatctac
       610                     630                     650
ctggaggtct tctacctaat ccgcaagcag ctcaacaaga aggtgtcggc ctcctccggc
       670                     690                     710
gacccgcaga agtactatgg gaaggagctg aagatcgcca agtcgctggc cctcatcctc
       730                     750                     770
ttcctctttg ccctcagctg gctgcctttg cacatcctca ctgcatcac cctcttctgc
       790                     810                     830
ccgtcctgcc acaagcccag catccttacc tacattgcca tcttcctcac gcacggcaac
       850                     870                     890
tcggccatga accccattgt ctatgccttc cgcatccaga agttccgcgt caccttcctt
       910                     930                     950
aagatttgga atgaccattt ccgctgccag cctgcacctc ccattgacga ggatctccca
       970
gaagagaggc ctgatgacta g
```

FIG.2

```
                        10                                          20
Met Pro Ile Met Gly Ser Ser Val Tyr Ile Thr Val Glu Leu Ala Ile Ala Val Leu Ala
                        30                                          40
Ile Leu Gly Asn Val Leu Val Cys Trp Ala Val Trp Leu Asn Ser Asn Leu Gln Asn Val
                        50                                          60
Thr Asn Tyr Phe Val Val Ser Leu Ala Ala Ala Asp Ile Ala Val Gly Val Leu Ala Ile
                        70                                          80
Pro Phe Ala Ile Thr Ile Ser Thr Gly Phe Cys Ala Ala Cys His Gly Cys Leu Phe Ile
                        90                                          100
Ala Cys Phe Val Leu Val Leu Thr Gln Ser Ser Ile Phe Ser Leu Leu Ala Ile Ala Ile
                        110                                         120
Asp Arg Tyr Ile Ala Ile Arg Ile Pro Leu Arg Tyr Asn Gly Leu Val Thr Gly Thr Arg
                        130                                         140
Ala Lys Gly Ile Ile Ala Ile Cys Trp Val Leu Ser Phe Ala Ile Gly Leu Thr Pro Met
                        150                                         160
Leu Gly Trp Asn Asn Cys Gly Gln Pro Lys Glu Gly Lys Asn His Ser Gln Gly Cys Gly
                        170                                         180
Glu Gly Gln Val Ala Cys Leu Phe Glu Asp Val Val Pro Met Asn Tyr Met Val Tyr Phe
                        190                                         200
Asn Phe Phe Ala Cys Val Leu Val Pro Leu Leu Leu Met Leu Gly Val Tyr Leu Arg Ile
                        210                                         220
Phe Leu Ala Ala Arg Arg Gln Leu Lys Gln Met Glu Ser Gln Pro Leu Pro Gly Glu Arg
                        230                                         240
Ala Arg Ser Thr Leu Gln Lys Glu Val His Ala Ala Lys Ser Leu Ala Ile Ile Val Gly
                        250                                         260
Leu Phe Ala Leu Cys Trp Leu Pro Leu His Ile Ile Asn Cys Phe Thr Phe Phe Cys Pro
                        270                                         280
Asp Cys Ser His Ala Pro Leu Trp Leu Met Tyr Leu Ala Ile Val Leu Ser His Thr Asn
                        290                                         300
Ser Val Val Asn Pro Phe Ile Tyr Ala Tyr Arg Ile Arg Glu Phe Arg Gln Thr Phe Arg
                        310                                         320
Lys Ile Ile Arg Ser His Val Leu Arg Gln Gln Glu Pro Phe Lys Ala Ala Gly Thr Ser
                        330                                         340
Ala Arg Val Leu Ala Ala His Gly Ser Asp Gly Glu Gln Val Ser Leu Arg Leu Asn Gly
                        350                                         360
His Pro Pro Gly Val Trp Ala Asn Gly Ser Ala Pro His Pro Glu Arg Arg Pro Asn Gly
                        370                                         380
Tyr Ala Leu Gly Leu Val Ser Gly Gly Ser Ala Gln Glu Ser Gln Gly Asn Thr Gly Leu
                        390                                         400
Pro Asp Val Glu Leu Leu Ser His Glu Leu Lys Gly Val Cys Pro Glu Pro Pro Gly Leu
                        410
Asp Asp Pro Leu Ala Gln Asp Gly Ala Gly Val Ser
```

FIG.3

```
         10                30                50
atgcccatca tgggctcctc ggtgtacatc acggtggagc tggccattgc tgtgctggcc
         70                90               110
atcctgggca atgtgctggt gtgctgggcc gtgtggctca acagcaacct gcagaacgtc
        130               150               170
accaactact ttgtggtgtc actggcggcg gccgacatcg cagtgggtgt gctcgccatc
        190               210               230
cccttttgcca tcaccatcag caccgggttc tgcgctgcct gccacggctg cctcttcatt
        250               270               290
gcctgcttcg tcctggtcct cacgcagagc tccatcttca gtctcctggc catcgccatt
        310               330               350
gaccgctaca ttgccatccg catcccgctc cggtacaatg gcttggtgac cggcacgagg
        370               390               410
gctaagggca tcattgccat ctgctgggtg ctgtcgtttg ccatcggcct gactcccatg
        430               450               470
ctaggttgga acaactgcgg tcagccaaag gagggcaaga accactccca gggctgcggg
        490               510               530
gagggccaag tggcctgtct ctttgaggat gtggtcccca tgaactacat ggtgtacttc
        550               570               590
aacttctttg cctgtgtgct ggtgccccctg ctgctcatgc tgggtgtcta tttgcggatc
        610               630               650
ttcctggcgg cgcgacgaca gctgaagcag atggagagcc agcctctgcc gggggagcgg
        670               690               710
gcacggtcca cactgcagaa ggaggtccat gctgccaagt cactggccat cattgtgggg
        730               750               770
ctctttgccc tctgctggct gccccctacac atcatcaact gcttcactttt cttctgcccc
        790               810               830
gactgcagcc acgcccctct ctggctcatg tacctggcca tcgtcctctc ccacaccaat
        850               870               890
tcggttgtga atcccttcat ctacgcctac cgtatccgcg agttccgcca gaccttccgc
        910               930               950
aagatcattc gcagccacgt cctgagggag caagaacctt tcaaggcagc tgcaccagt
        970               990              1010
gcccgggtct tggcagctca tggcagtgac ggagagcagg tcagcctccg tctcaacggc
       1030              1050              1070
caccccgccag gagtgtgggc caacggcagt gctccccacc ctgagcggag gcccaatggc
       1090              1110              1130
tatgccctgg ggctggtgag tgggggagt gcccaagagt cccaggggaa cacgggcctc
       1150              1170              1190
ccagacgtgg agctccttag ccatgagctc aagggagtgt gcccagagcc ccctggccta
       1210              1230
gatgacccc tggcccagga tgggagcagga gtgtccctga
```

FIG.4

```
                                    10                                      20
    Met Leu Leu Glu Thr Gln Asp Ala Leu Tyr Val Ala Leu Glu Leu Val Ile Ala Ala Leu
                                    30                                      40
    Ser Val Ala Gly Asn Val Leu Val Cys Ala Ala Val Gly Thr Ala Asn Thr Leu Gln Thr
                                    50                                      60
    Pro Thr Asn Tyr Phe Leu Val Ser Leu Ala Ala Ala Asp Val Ala Val Gly Leu Phe Ala
                                    70                                      80
    Ile Pro Phe Ala Ile Thr Ile Ser Leu Gly Phe Cys Thr Asp Phe Tyr Gly Cys Leu Phe
                                    90                                     100
    Leu Ala Cys Phe Val Leu Val Leu Thr Gln Ser Ser Ile Phe Ser Leu Leu Ala Val Ala
                                   110                                     120
    Val Asp Arg Tyr Leu Ala Ile Cys Val Pro Leu Arg Tyr Lys Ser Leu Val Thr Gly Thr
                                   130                                     140
    Arg Ala Arg Gly Val Ile Ala Val Leu Trp Val Leu Ala Phe Gly Ile Gly Leu Thr Pro
                                   150                                     160
    Phe Leu Gly Trp Asn Ser Lys Asp Ser Ala Thr Asn Asn Cys Thr Glu Pro Trp Asp Gly
                                   170                                     180
    Thr Thr Asn Glu Ser Cys Cys Leu Val Lys Cys Leu Phe Glu Asn Val Val Pro Met Ser
                                   190                                     200
    Tyr Met Val Tyr Phe Asn Phe Phe Gly Cys Val Leu Pro Pro Leu Leu Ile Met Leu Val
                                   210                                     220
    Ile Tyr Ile Lys Ile Phe Leu Val Ala Cys Arg Gln Leu Gln Arg The Glu Leu Met Asp
                                   230                                     240
    His Ser Arg Thr Thr Leu Gln Arg Glu Ile His Ala Ala Lys Ser Leu Ala Met Ile Val
                                   250                                     260
    Gly Ile Phe Ala Leu Cys Trp Leu Pro Val His Ala Val Asn Cys Val Thr Leu Phe Gln
                                   270                                     280
    Pro Ala Gln Gly Lys Asn Lys Pro Lys Trp Ala Met Asn Met Ala Ile Leu Leu Ser His
                                   290                                     300
    Ala Asn Ser Val Val Asn Pro Ile Val Tyr Ala Tyr Arg Asn Arg Asp Phe Arg Tyr Thr
                                   310                                     320
    Phe His Lys Ile Ile Ser Arg Tyr Leu Leu Cys Gln Ala Asp Val Lys Ser Gly Asn Gly
                                   330
    Gln Ala Gly Val Gln Pro Ala Leu Gly Val Gly Leu
```

FIG.5

```
        10              30              50
atgctgctgg agacacagga cgcgctgtac gtggcgctgg agctggtcat cgccgcgctt
        70              90              110
tcggtggcgg gcaacgtgct ggtgtgcgcc gcggtgggca cggcgaacac tctgcagacg
        130             150             170
cccaccaact acttcctggt gtccctggct gcggccgacg tggccgtggg gctcttcgcc
        190             210             230
atcccctttg ccatcaccat cagcctgggc ttctgcactg acttctacgg ctgcctcttc
        250             270             290
ctcgcctgct tcgtgctggt gctcacgcag agctccatct tcagccttct ggccgtggca
        310             330             350
gtcgacagat acctggccat ctgtgtcccg ctcaggtata aaagtttggt cacggggacc
        370             390             410
cgagcaagag gggtcattgc tgtcctctgg gtccttgcct ttggcatcgg attgactcca
        430             450             470
ttcctggggt ggaacagtaa agacagtgcc accaacaact gcacagaacc ctgggatgga
        490             510             530
accacgaatg aaagctgctg ccttgtgaag tgtctctttg agaatgtggt ccccatgagc
        550             570             590
tacatggtat atttcaattt ctttgggtgt gttctgcccc cactgcttat aatgctggtg
        610             630             650
atctacatta agatcttcct ggtggcctgc aggcagcttc agcgcactga gctgatggac
        670             690             710
cactcgagga ccacccteca gcgggagatc catgcagcca gtcactggc catgattgtg
        730             750             770
gggatttttg ccctgtgctg gttacctgtg catgctgtta actgtgtcac tctttttcag
        790             810             830
ccagctcagg gtaaaaataa gcccaagtgg gcaatgaata tggccattct tctgtcacat
        850             870             890
gccaattcag ttgtcaatcc cattgtctat gcttaccgga accgagactt ccgctacact
        910             930             950
tttcacaaaa ttatctccag gtatcttctc tgccaagcag atgtcaagag tgggaatggt
        970             990
caggctgggg tacagcctgc tctcggtgtg ggcctatga
```

FIG.6

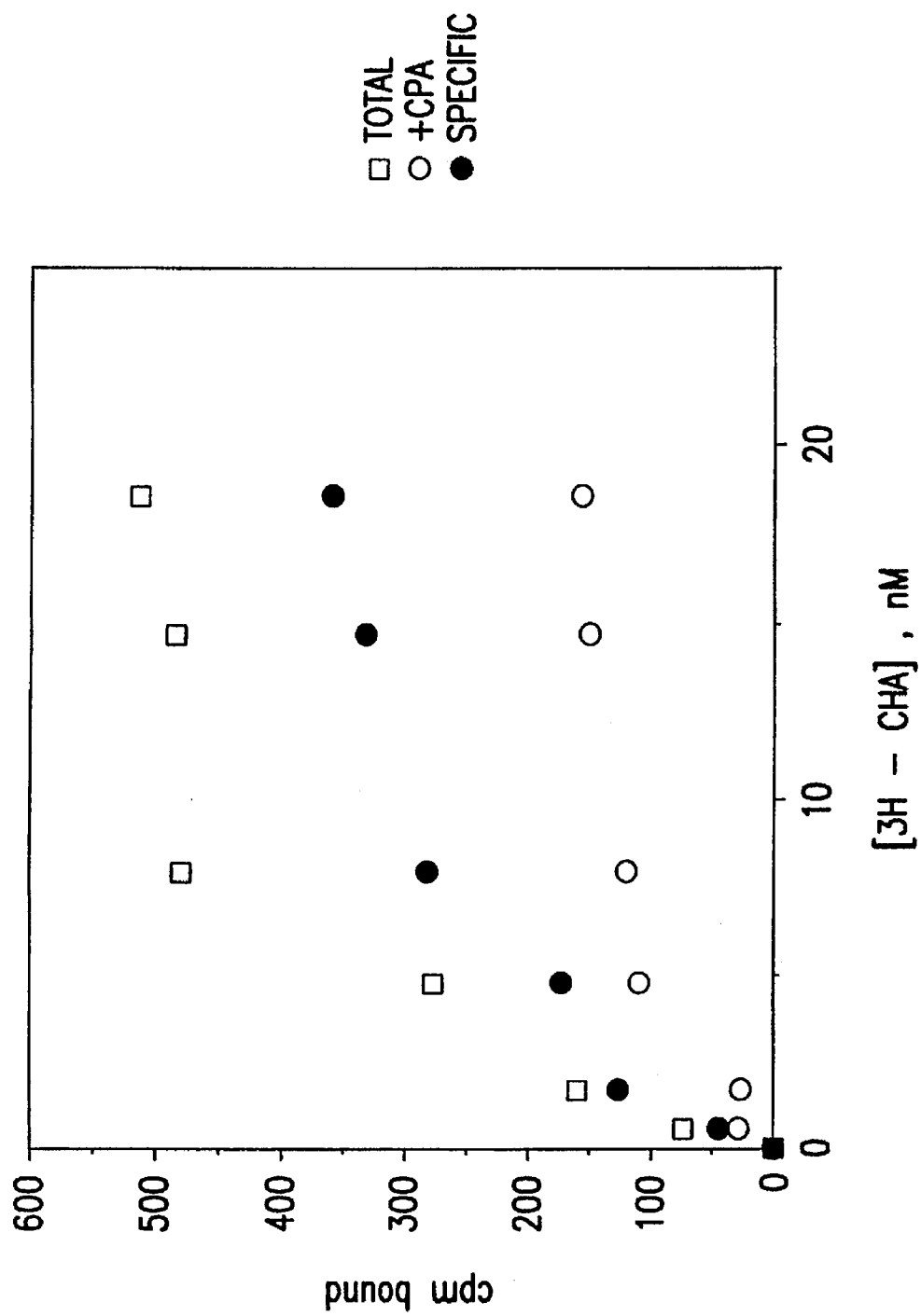

```
                        10                                      20
Met Pro Asn Asn Ser Thr Ala Leu Ser Leu Ala Asn Val Thr Tyr Ile Thr Met Glu Ile
                        30                                      40
Phe Ile Gly Leu Cys Ala Ile Val Gly Asn Val Leu Val Ile Cys Val Val Lys Leu Asn
                        50                                      60
Pro Ser Leu Gln Thr Thr Thr Phe Tyr Phe Ile Val Ser Leu Ala Leu Ala Asp Ile Ala
                        70                                      80
Val Gly Val Leu Val Met Pro Leu Ala Ile Val Val Ser Leu Gly Ile Thr Ile His Phe
                        90                                     100
Tyr Ser Cys Leu Phe Met Thr Cys Leu Leu Leu Ile Phe Thr His Ala Ser Ile Met Ser
                       110                                     120
Leu Leu Ala Ile Ala Val Asp Arg Tyr Leu Arg Val Lys Leu Thr Val Arg Tyr Lys Arg
                       130                                     140
Val Thr Thr His Arg Arg Ile Trp Leu Ala Leu Gly Leu Cys Trp Leu Val Ser Phe Leu
                       150                                     160
Val Gly Leu Thr Pro Met Phe Gly Trp Asn Met Lys Leu Thr Ser Glu Tyr His Arg Asn
                       170                                     180
Val Thr Phe Leu Ser Cys Gln Phe Val Ser Val Met Arg Met Asp Tyr Met Val Tyr Phe
                       190                                     200
Ser Phe Leu Thr Trp Ile Phe Ile Pro Leu Val Val Met Cys Ala Ile Tyr Leu Asp Ile
                       210                                     220
Phe Tyr Ile Ile Arg Asn Lys Leu Ser Leu Asn Leu Ser Asn Ser Lys Glu Thr Gly Ala
                       230                                     240
Phe Tyr Gly Arg Glu Phe Lys Thr Ala Lys Ser Leu Phe Leu Val Leu Phe Leu Phe Ala
                       250                                     260
Leu Ser Trp Leu Pro Leu Ser Ile Ile Asn Cys Ile Ile Tyr Phe Asn Gly Glu Val Pro
                       270                                     280
Gln Leu Val Leu Tyr Met Gly Ile Leu Leu Ser His Ala Asn Ser Met Met Asn Pro Ile
                       290                                     300
Val Tyr Ala Tyr Lys Ile Lys Lys Phe Lys Glu Thr Tyr Leu Leu Ile Leu Lys Ala Cys
                       310
Val Val Cys His Pro Ser Asp Ser Leu Asp Thr Ser Ile Glu Lys Asn Ser Glu
```

FIG.9

```
          10                    30                    50
atgcccaaca acagcactgc tctgtcattg gccaatgtta cctacatcac catggaaatt
          70                    90                   110
ttcattggac tctgcgccat agtgggcaac gtgctggtca tctgcgtggt caagctgaac
         130                   150                   170
cccagcctgc agaccaccac cttctatttc attgtctctc tagccctggc tgacattgct
         190                   210                   230
gttggggtgc tggtcatgcc tttggccatt gttgtcagcc tgggcatcac aatccacttc
         250                   270                   290
tacagctgcc tttttatgac ttgcctactg cttatcttta cccacgcctc catcatgtcc
         310                   330                   350
ttgctggcca tcgctgtgga ccgatacttg cgggtcaagc ttaccgtcag atacaagagg
         370                   390                   410
gtcaccactc acagaagaat atggctggcc ctgggccttt gctggctggt gtcattcctg
         430                   450                   470
gtgggattga cccccatgtt tggctggaac atgaaactga cctcagagta ccacagaaat
         490                   510                   530
gtcaccttcc tttcatgcca atttgtttcc gtcatgagaa tggactacat ggtatacttc
         550                   570                   590
agcttcctca cctggatttt catccccctg gttgtcatgt gcgccatcta tcttgacatc
         610                   630                   650
tttacatca ttcggaacaa actcagtctg aacttatcta actccaaaga gacaggtgca
         670                   690                   710
ttttatggac gggagttcaa gacggctaag tccttgtttc tggttctttt cttgtttgct
         730                   750                   770
ctgtcatggc tgcctttatc tatcatcaac tgcatcatct actttaatgg tgaggtacca
         790                   810                   830
cagcttgtgc tgtacatggg catcctgctg tcccatgcca actccatgat gaaccctatc
         850                   870                   890
gtctatgcct ataaaataaa gaagttcaag gaaacctacc ttttgatcct caaagcctgt
         910                   930                   950
gtggtctgcc atccctctga ttctttggac acaagcattg agaagaattc tgagtag
```

FIG.10

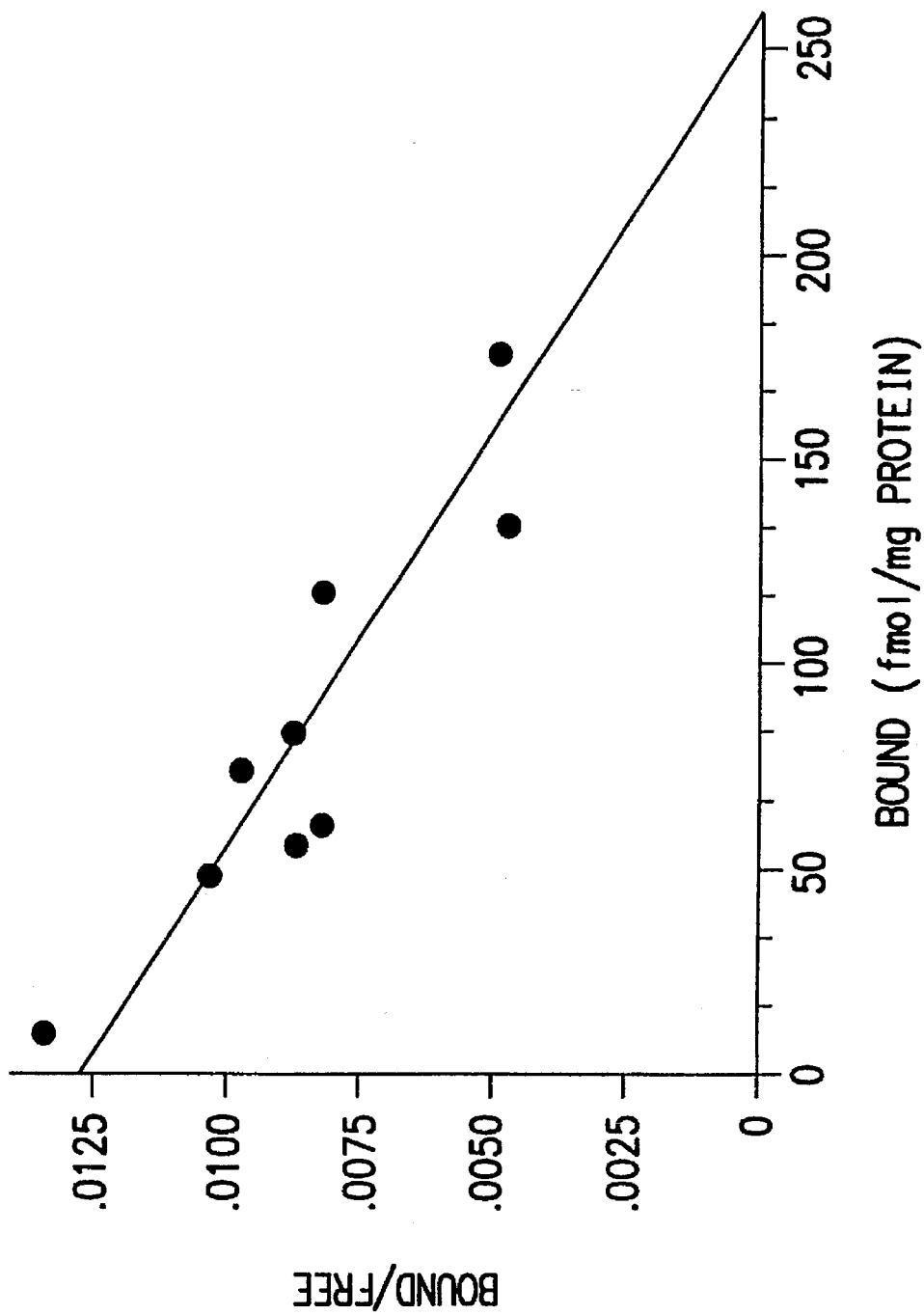

INHIBITION OF EOSINOPHIL ACTIVATION THROUGH A3 ADENOSINE RECEPTOR ANTAGONISM

BACKGROUND OF THE INVENTION

1. Field of the Invention

The present invention concerns the identification on human eosinophils of the A3 adenosine receptor, and the use of compounds identified as specific modulators of adenosine's physiological actions to block activation of eosinophils. The pharmacology of compounds useful according to this invention is characterized through the use of cloned human adenosine A1, A2a, A2b and A3 receptor subtypes and functional assays. Compounds identified as antagonists of the A3 adenosine receptor subtype prevent the decrease in intracellular cAMP caused by activation of the A3 adenosine receptor by adenosine agonists. In this manner, A3 adenosine receptor specific antagonists are useful in preventing eosinophil activation and are therefore useful in the treatment or prevention of disease states induced by activation of the A3 adenosine receptor. These disease states include but are not limited to asthma, hypersensitivity, rhinitis, hay fever, serum sickness, allergic vasculitis, atopic dermatitis, dermatitis, psoriasis, eczema, idiopathic pulmonary fibrosis, eosinophillic cholecystitis, chronic airway inflammation, hypereosinophilic syndromes, eosinophillic gastroenteritis, edema, urticaria, eosinophilic myocardial disease, episodic angioedema with eosinophilia, inflammatory bowel disease, ulcerative colitis, allergic granulomatosis, carcinomatosis, eosinophilic granuloma and familial histiocytosis.

2. Background

Adenosine is a naturally occurring nucleoside which exhibits diverse and potent physiological actions in the cardiovascular, nervous, pulmonary, renal and immune systems. Adenosine has been demonstrated to terminate supraventricular tachycardia through blockage of atrioventricular nodal conduction (J. P. DiMarco, et al., (1985) J. Am. Col. Cardiol. 6:417–425, A. Munoz, et al., (1984) Eur. Heart J. 5:735–738). Adenosine is a potent vasodilator except in the kidney and placenta (R. A. Olsson, (1981) Ann. Rev. Physiol. 43:385–395). Adenosine produces bronchoconstriction in asthmatics but not in nonasthmatics (Cushly et al., 1984, Am. Rev. Respir. Dis. 129:380–384). Adenosine has been implicated as a preventative agent and in treatment of ventricular dysfunction following episodes of regional or global ischemia (M. B. Forman and C. E. Velasco (1991) Cardiovasc. Drugs and Therapy 5:901–908) and in cerebral ischemia(M. C. Evans, et al., (1987) Neurosci. Lett. 83:287, D. K. J. E., Von Lubitz, et al., (1988) Stroke 19:1133).

Dog A1 and A2a adenosine receptors were the first adenosine receptors to be cloned. See F. Libert, et al., (1989) Science 244:569–572, C. Maenhaut, et al., Biochem. Biophys. Res. Comm., (1990) 173:1169–1178, and F. Libert, et al. (1991) EMBO J. 10:1677–1682. The rat A1 adenosine receptor was cloned by L. C. Mahan, et al., (1991) Mol. Pharm. 40:1–7 and S. M. Reppert, et al., (1991) Mol. Endocrin. 5:1037–1048, the rat A2a by Fink et. al., (1992) Mol. Brain Res. 14:186–195, and the rat A2b by Stehle et al. (1992) Mol. Endocrinol. 6:384–393. Cloning of the rat A3 adenosine receptor was reported by Meyerhof et al., (1991) FEBS Lett. 284:155–160 and Zhou et al., (1992) PNAS U.S.A. 89:7432–7436. Cloning of the sheep A3 adenosine receptor has been reported by Linden et al., (1993) Mol. Pharm. 44:524–532. Cloning of the human A1, A2a, A2b and A3 receptors were reported in GB 2264948-A (Sep. 15, 1993). The human A1 adenosine receptor differs by 18 amino acids from the dog A1 sequence and 16 amino acids from the rat A1 sequence. The human A2a adenosine receptor differs by 28 and 71 amino acids, respectively from the dog and rat A2a sequences. The amino acid sequence for the human A3 receptor is 72% identical with the rat A3 receptor and 85% identical with the sheep A3 receptor sequences.

The actions of adenosine are mediated through the G-protein coupled receptors A1, A2a, A2b and A3 adenosine receptors. Upon activation of the adenosine receptors, the G-protein exerts either a stimulatory effect (A2a and A2b adenosine receptor coupled G-proteins) or an inhibitory effect (A1 and A3 adenosine receptor coupled G-proteins) on adenylate cyclase. Thus, adenosine receptor activation induces changes in intracellular cAMP and thereby initiates a cascade of intracellular events.

The adenosine receptors were initially classified into A1 and A2 subtypes on the basis of pharmacological criteria and coupling to adenylate cyclase (Van Caulker, D., Muller, M. and Hamprecht, B. (1979) J. Neurochem. 33, 999–1003.). Further pharmacological classification of adenosine receptors prompted subdivision of the A2 class into A2a and A2b subtypes on the basis of high and low affinity, respectively, for adenosine and the agonists NECA and CGS-21680 (Bruns, R. F., Lu, G. H. and Pugsley, T. A. (1986) Mol. Pharmacol. 29, 331–346; Wan, W., Sutherland, G. R. and Geiger, J. D. (1990) J. Neurochem. 55, 1763–1771). The existence of A1, A2a and A2b subtypes has been confirmed by cloning and functional characterization of expressed bovine, canine, rat and human receptors. A fourth subtype, A3, had remained pharmacologically undetected until its recent identification by molecular cloning. The rat A3 sequence, tgpcr1, was first cloned from rat testis by Meyerhoff et al. (see above). Subsequently, a cDNA encoding the identical receptor was cloned from striatum and functionally expressed by Zhou et al. (see above). When compared to the other members of the G-protein coupled receptor family, the rat sequence had the highest homology with the adenosine receptors (>40% overall identity, 58% within the transmembrane regions). When stably expressed in CHO cells, the receptor was found to bind the radioligand $^{125}$I-APNEA ($N^6$-2-(4-amino-3-iodophenyl)ethyladenosine) and when transfected cells were treated with adenosine agonists, cyclic AMP accumulation was inhibited with a potency order of NECA=R-PIA>CGS21680. The rat A3 receptor exhibited a unique pharmacology relative to the A1 and A2 adenosine receptor subtypes and was reported not to bind the xanthine antagonists 1,3-dipropyl-8-phenylxanthine (DPCPX) and xanthine amine congener (XAC). Messenger RNA for the rat A3 adenosine receptor is primarily expressed in the testis.

The sheep homolog of the A3 receptor was cloned from hypophysial pars tuberalis (see Linden et al. above). The sheep receptor is 72% identical to the rat receptor, binds the radioligand $^{125}$I-ABA and is also coupled to inhibition of cyclic AMP. The agonist affinity order of the sheep receptor is I-ABA>APNEA>NECA≧R-PIA>>CPA. The pharmacology of xanthine antagonists was extensively studied and the sheep receptor was found to exhibit high affinity for 8-phenylxanthines with para-acidic substitutions. In contrast to the rat transcript, the expression of the sheep A3 adenosine receptor transcript is widespread throughout the brain and is most abundant in the lung and spleen. Moderate amounts of transcript are also observed in pineal and testis. Thus, because the published literature provides an inconsistent profile of adenosine A3 receptor pharmacology and tissue distribution, it has not been possible to predict the pharmacology or tissue distribution of the human A3 adenosine receptor.

The human A1, A2a and A2b adenosine receptor cDNAs have been cloned, and the tissue distribution of human adenosine receptor transcripts has been defined [Salvatore et al., *P.N.A.S.* 90:10365–10369, November 1993]. Based on the use of these cloned receptors, an assay has been described to identify adenosine receptor agonists, antagonists and enhancers and determine their binding affinity (see GB 2 264 948 A, published Sep. 15, 1993; see also R. F. Bruns, et al., (1983) Proc. Natl. Acad. Sci. U.S.A. 80:2077–2080; R. F. Brtms, et al., (1986) Mol. Pharmacol. 29:331–346; M. F. Jarvis, et al. (1989) J. Pharma. Exp. Therap. 251:888–893; K. A. Jacobson et al., (1989) J. Med. Chem. 32:1043–1051).

Adenosine receptor agonists, antagonists and binding enhancers have been identified and implicated for usage in the treatment of physiological complications resulting from cardiovascular, pulmonary, renal and neurological disorders. Adenosine receptor agonists have been identified for use as vasodilators ((1989) FASEB. J. 3(4) Abs 4770 and 4773, (19910 J. Med. Chem. (1988) 34:2570), antihypertensive agents (D. G. Taylor et al., FASEB J. (1988) 2:1799), and anti-psychotic agents (T. G. Heffner et al., (1989) Psychopharmacology 98:31–38). Adenosine receptor agonists have been identified for use in improving renal function (R. D. Murray and P. C. Churchill,(1985) J. Pharmacol. Exp. Therap. 232:189–193). Adenosine receptor allosteric or binding enhancers have shown utility in the treatment of ischemia, seizures or hypoxia of the brain (R. F. Bruns, et al. (1990) Mol. Pharmacol. 38:939–949; C. A. Janusz, et al., (1991) Brain Research 567:181–187). The cardioprotective agent, 5-amino-4-imidazole carboxamide (AICA) ribose has utility in the treatment of ischemic heart conditions, including unstable angina and acute myocardial infarction (H. E. Graber, et al. (1989) Circulation 80: 1400–1414).

8-phenylxanthines, methods of their synthesis and their use in human and veterinary therapy for conditions associated with the cell surface effects of adenosine have been described (EP 0 203 721, published Dec. 3, 1986). However, this publication is silent as to adenosine receptor subtypes and subtype specificity of disclosed compounds. In WO 90/00056, a group of 1,3-unsymmetrical straight chain alkyl-substituted 8-phenylxanthines were described as being potent bronchodilators. This disclosure is likewise silent as to the subtype specificity of disclosed compounds.

Through the use of homogenous, recombinant adenosine receptors, the identification and evaluation of compounds which have selectivity for a single receptor subtype has now been accomplished. Moreover, because of the variable effects of adenosine documented in other species, the utilization of human adenosine receptor subtypes is advantageous for the development of human therapeutic adenosine receptor agonists, antagonists or enhancers. The instant patent disclosure defines compounds which unexpectedly exhibit selective binding affinity for eosinophils by virtue of the presence on this cell type of the A3 adenosine receptor and therefore provides a method of using such compounds which overcomes the disadvantages of using compounds of uncharacterized specificity, by specifically blocking the activities mediated through the activation of the A3 receptor subtype without substantially blocking the activities of the other adenosine receptor subtypes.

Corticoidsteroids administered orally or through inhalation, are effective agents for the treatment of allergic, inflammatory and asthmatic states. Specifically, the use of corticoidsteroids for asthma reduces bronchial hyperresponsivness. The mechanism of action results from antiinflammatory effects in part on eosinophils. The chronic use of corticoidsteroids results in a reduction in the number of eosinophils in the systemic circulation and within tissues, and in a decrease of the migration of eosinophils to sites of inflammation. A number of adverse systemic side effects are associated with the use of steroids including fluid retention, hypertension, peptic ulceration, and adrenal suppression. These side effects are the result of the multiple actions of steroids on tissues and organs. A eosinophil selective therapy would therefore, be advantageous for the reduction or elimination of these adverse effects.

Recently, the effectiveness of a monoclonal antibody raised against the integrin α4 chain was demonstrated in an allergic sheep model of airway late phase responses and airway hyperresponsivness (Abraham, et al. (1994) J. Clin. Invest. 93: 776–787). Administration of the blocking antibody either prior or after allergic challenge was found to be effective. The antibody was also found to reduce the platelet-activating factor induced peroxidase release from eosinophils and supported a mechanism of inhibiting eosinophil function for the alleviation of late phase responses and persisting airway hyperresponsiveness after antigen challenge. These data support the importance of eosinophil activation and degranulation in mediating allergic, asthmatic and hyperresponsive conditions and illustrates that agents which can modulate and inhibit eosinophil functions are effective in preventing and treating such conditions.

Salvatore et al., [*P.N.A.S.* 90:10365–10369, November 1993] disclosed the pharmacological profile of the human A3 adenosine receptor, and the tissue distribution of human A1, A2a, A2b and A3 adenosine receptor transcripts. In addition, the activity of certain substituted 8-phenyl xanthines as specific antagonists of the human A3 adenosine receptor was disclosed. The instant invention extends the characterization of the A3 adenosine receptor subtype by demonstrating the existence of the A3 adenosine receptor subtype on eosinophils. In view of the known association of intracellular cAMP decreases with eosinophil activation [see Kuehl, et al, (1987) Am. Rev. Respir. Dis. 136: 210–213; see also Kita et al., *J. Immunol.* 146:2712–2718, 1991, regulation of Ig-induced eosinophil degranulation by adenosine 3',5'-cyclic monophosphate], and the known coupling of the A3 adenosine receptor to inhibition of adenylate cyclase [Salvatore et al., *P.N.A.S.* 90:10365–10369, November 1993] and as confirmed herein, our discovery of the expression of the A3 adenosine receptor subtype in eosinophils demonstrates the utility of A3 adenosine receptor antagonists in the prevention of that component of eosinophil activation attributable to the decrease in intracellular cAMP normally induced by activation of the A3 adenosine receptor on eosinophils.

BRIEF DESCRIPTION OF THE DRAWINGS

FIG. 1 Full length amino acid sequence of human A1 adenosine receptor.

FIG. 2 Full length nucleotide sequence of the cloned human A1 adenosine receptor complementary DNA depicted from the 5' to 3' terminus.

FIG. 3 Full length amino acid sequence of human A2a adenosine receptor.

FIG. 4 Full length nucleotide sequence of cloned human A2a adenosine receptor complementary DNA depicted from the 5' to 3' terminus.

FIG. 5 Full length amino acid sequence of human A2b receptor.

FIG. 6 Full length nucleotide sequence of cloned human A2b adenosine receptor complementary DNA depicted from the 5' to 3' terminus.

FIG. 7 Saturation binding of [$^3$H]-cyclohexyladenosine (CHA) to human A1 adenosine receptor in COS7 assay.

FIG. 9 Full length amino acid sequence of human A3 adenosine receptor.

FIG. 10 Full length nucleotide sequence of the cloned human A3 adenosine receptor complementary DNA depicted from the 5' to 3' terminus.

FIG. 20 40× magnification of antisense hybridization on eosinophils from FIG. 19a.

SUMMARY OF THE INVENTION

Figure 8:
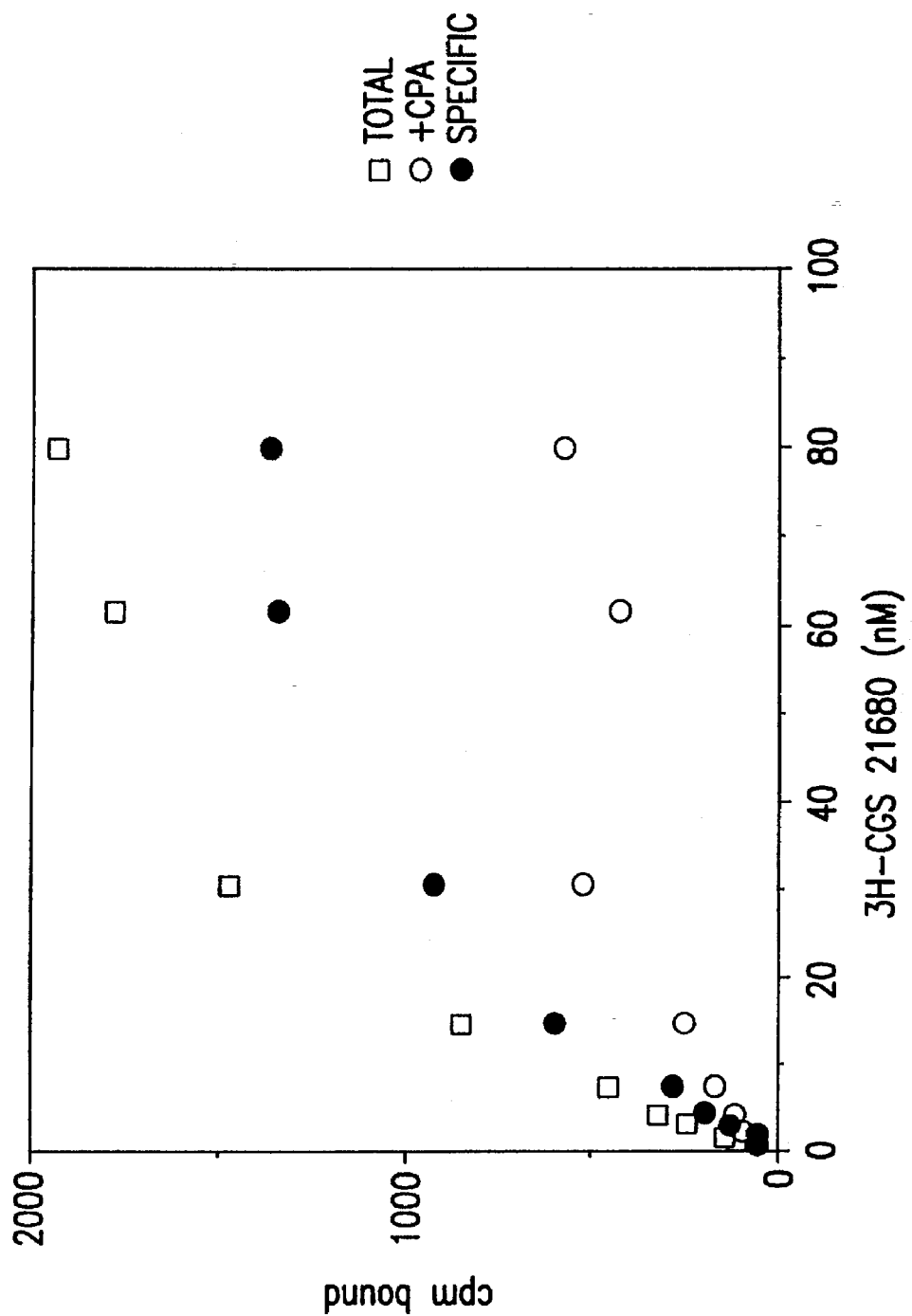
FIG. 8 Saturation binding of [$^3$H]-CGS21680 to human A2a adenosine receptor in COS7 assay.

This invention concerns the identification on eosinophils of the A3 adenosine receptor subtype and the blockade of said receptor in order to achieve inhibition of eosinophil activation. In addition, the invention discloses a method for achieving blockade of cytokine induced hypersensitivity of eosinophils to adenosine agonists which comprises contacting eosinophils with an antagonistically effective amount of an A3 adenosine receptor subtype specific antagonist. Compounds identified as being A3 adenosine receptor specific antagonists through the use of recombinant human adenosine receptors A1, A2a, A2b and A3, and functional assays including intracellular cyclic AMP determinations, are useful according to the method of this invention.

ABBREVIATIONS

[$^3$H]-CHA, [$^3$H]-cyclohexyladenosine; [$^3$H]-NECA, [$^3$H]-5'-N-ethylcarboxamido-adenosine; $^{125}$I-ABA, N$^6$-(4-amino-3-$^{125}$iodobenzyl)adenosine; $^{125}$I-APNEA, N$^6$-2-(4-amino-3-$^{125}$iodophenyl)ethyladenosine; NECA, N-ethylcarboxamidoadenosine; CGS21680, 2-[4-(2-carboxyethyl)phenyl]ethylamino-5'-N-ethylcarboxamidoadenosine; (R,S)-PIA, (R,S)-N$^6$-phenyl-2-propyladenosine; CPA, N$^6$-cyclopentyladenosine; I-ABOPX, (3-(3-iodo-4-aminobenzyl)-8-(4-oxyacetate) phenyl-1-propopylxanthine; BW-A1433, 1,3-dipropyl-8-(4-acrylate)phenylxanthine; XAC, xanthine amine cogener; DPCPX, 1,3-dipropyl-8-cyclopentylxanthine; GTPgS, guanosine 5'-O-3-thiotriphosphate; Gpp(NH)p, 5'-guanylimidodiphosphate; G protein, guanine nucleotide-binding proteins.

DETAILED DESCRIPTION OF THE INVENTION

We have determined that A3 adenosine receptors are expressed on human eosinophils by reverse-transcriptase polymerase chain reaction and in situ hybridization of lung sections. A particular set of oligonucleotide probes and primers was prepared for this purpose. Accordingly, one embodiment of this invention is a method of identifying the expression of a particular adenosine receptor subtype which comprises using any the disclosed oligonucleotide sequences as an in-situ hybridization probe or as a primer for reverse transcriptase polymerase chain reaction analysis.

We have discovered that the expression of A3 transcripts on eosinophils is upregulated with cytokine stimulation. This suggests that activation of A3 receptors by adenosine is amplified in inflammatory states.

The A3 receptor is coupled to the inhibition of adenylyl cyclase. Activation of A3 receptors on eosinophils by the agonist adenosine results in a decrease in intracellular cAMP levels and ultimately, eosinophil degranulation and effector function. Antagonism of A3 receptors prevents the decrease in intracellular cAMP levels. This inhibits eosinophil effector function and degranulation. Blockade of eosinophil A3 adenosine receptors acts synergistically with the β-adrenergic stimulation, which is known to stimulate adenylate cyclase. Thus, a combination therapy including A3 adenosine receptor blockade and β-adrenergic receptor stimulation maintains elevated intracellular cAMP and thereby inhibits release of eosinophilic mediators.

In asthmatics, mean adenosine concentrations measured in BAL fluid are significantly elevated relative to normal patients (Driver, et al. (1993) Am. Rev. Respir. Dis. 148:91–97). High concentrations of adenosine in airway fluids are therefore available for binding to and activation of A3 receptors that we have discovered are present on eosinophils. Accumulation of activated eosinophils in bronchial mucosa in response to an allergic challenge and activation of the A3 receptors results in eosinophil degranulation and exacerbation of the inflammatory and allergic responses.

Thus the use of an A3 adenosine receptor antagonist to suppress eosinophil effector responses forms an integral part of this invention.

In view of the role of A3 receptor blockade on eosinophil degranulation, this method is useful in the treatment and prevention of diseased states associated with allergy and intimation including asthma, hypersensitivity, rhinitis, hay fever, serum sickness, allergic vasculitis, dermatitis, psoriasis, eczema, atopic dermatitis, idiopathic pulmonary fibrosis, eosinophillic cholecystitis, chronic airway inflammation, eosinophillic gastroenteritis, edema and urticaria, eosinophillic myocardial disease, episodic angioedema with eosinophillia, inflammatory bowel disease, hypereosinophilic syndromes, ulcerative colitis, allergic granulomatosis, carcinomatosis, eosinophilic granuloma and familial histiocytosis.

Eosinophils are important effector cells in inflammatory, allergic and asthmatic diseases. Increasing evidence has correlated the recruitment of activated eosinophils to airways and the accumulation in the bronchial mucosa with the development of the late-phase response and bronchial hyperresponsiveness in asthma. Eosinophils are a source of potent inflammatory mediators which cause bronchoconstriction such as leukotrienes (Shaw et al. (1985) Nature 316:150–152) and platelet activating factor (Cromwell et al. (1990) J. Immunol. 145: 3419–3423). Eosinophils release major basic protein and cationic protein which damage respiratory epithelium and can provoke airway hyperresponsiveness. In an animal model of asthma, allergic sheep that develop antigen-induced late airway responses have been reported to have increased numbers of eosinophils in bronchoalveolar lavage (BAL) fluid obtained during the late phase response (Abraham, et al. (1988), Am. Rev. Respir. Dis. 138: 1565–1571). In contrast, animals that responded immediately to antigen challenge, acute responders, exhibited no increase in eosinophil recruitment. In BAL fluid (De Monchy et al. (1985) Am. Rev. Respir. Dis. 131:373–376) and biopsed airway tissues from asthmatic patients (Beasley, et al. (1989) Am. Rev. Respir. Dis. 139:806–817; Azzawi et al. (1989) Thorax 44:882P-883P; Azzawi et al. (1992) Am. Rev. Respir. Dis. 145: 1477–1482), an increase in the number of eosinophils has been documented. The degree of associated bronchial hyperresponsiveness in atopic asthmatics who develop late phase bronchoconstriction correlated with peripheral blood eosinophil counts (Durham and Kay (1985) Clin. Allergy 15: 411–418; Bousquet et al. (1990) 323: 1033–1039). In view of these findings, our discovery of a mechanism to inhibit eosinophil activation represents a substantial advance in the discovery of treatments for pathologies associated with eosinophil activation.

Exposure of normal peripheral eosinophils to cytokines such as granulocyte-macrophge colony stimulating factor (GM-CSF), interleukin IL-3 or IL-5 results in functional priming of the eosinophil. The cytokine-induced priming causes a change from a normodense state to a hypodense state. In addition to the decrease in density, functional consequences of priming include increased eosinophil viability (Begley et al. (1986) Blood 68: 162–166), increased expression of lymphocyte-function-related antigen (LFA-1) which results in an increased potential for adherence, increased antibody-dependent cytotoxicity, augmentation of degranulation, phagocytosis, superoxide generation, leukotriene generation (Silberstein et al. (1986) J. Immunol. 137: 3290–3294) and proteoglycan synthesis.

Beta$_2$-adenrenoceptor agonists ($\beta_2$-agonists) and theophylline are commonly used as "first-line" maintenance treatments for asthma. $\beta_2$-agonists are potent bronchodilators and are effective in reversing airway obstruction in asthmatics and allergic patients. The therapeutic effect of $\beta_2$-agonists is derived form the direct action on $\beta_2$-receptors present on airway smooth muscle and indirectly through inhibition of mediator release from inflammatory cells. $\beta_2$-receptors are coupled to adenylyl cyclase and when activated, cause an increase in intracellular adenosine 3',5'-cyclic monophoshate, cAMP. The mechanism of therapeutic action of theophylline is unclear. Theophylline functions as a phophodiesterase inhibitor and prevents the hydrolysis of cAMP. Theophylline is also an adenosine receptor antagonist. A common end-result of $\beta_2$-receptor activation and phosphodiesterase inhibition is an increase in intracellular cAMP levels. Increases in intracellular cAMP has been linked to suppression of eosinophil degranulation. Kito et al. ((1990) J. Immunol. 146: 2712–2718) has shown that increases in intracellular cAMP levels has an inhibitory effect on eosinophil activation. Pretreatment with cAMP analogs, phosphodiesterase inhibitors and $\beta_2$-agonists inhibited IgG or secretory IgA-induced eosinophil effector function. These results implicated the significance of a cAMP-dependent signal transduction mechanism on eosinophils which negatively regulates Ig-induced degranulation. Pretreatment of eosinophils with permssis toxin resulted in the inhibition of secretory IgA-induced eosinophil degranulation and suggested that the uncoupling of $G_i$ proteins is effective for inhibition of eosinophil effector function.

Adenosine induces bronchoconstriction in asthmatics but not in normal individuals. The mechanism of this effect is unknown. Adenosine mediated bronchoconstriction is asthmatics is blocked by a combination of histamine and leukotriene antagonists (Bjorck et al., (1992) Am. Rev. Respir. Dis. 145: 1087–1091) indicating that adenosine acts by induction or augmentation of histamine, leukotriene and other mediators from inflammatory cells involved in a allergic/asthmatic response. Adenosine has been shown to potentiate the release of histamine from activated mast cells (Hughes et al., (1984) Biochem. Pharmacol. 33: 3847–3852). Additionally, adenosine mediates the action of inflammatory cells including neutrophils (Rose et al. (1988) J. Exp. Med. 167: 1186–1194; Cronstein et al. (1985) J. Immunol. 135: 1366–1371), eosinophils (Yukawa et al., (1989) Am. Rev. Respir. Dis. 140: 327–333) and stimulated monocytes (Vraux et al. (1993) Life Sci. 52: 1917–1924) through receptor subtypes expressed on the cell surface. The adenosine receptors are coupled to adenylyl cyclase and upon activation with the agonist, adenosine, modulate the levels of intracellular cAMP. Activation of the A3 adenosine receptor subtype results in the decrease of intracellular cAMP.

Salvatore et al., [P.N.A.S. 90:10365–10369, November 1993] determined that expression of human A3 adenosine receptor subtype transcripts is abundant in the human lung. Linden et al, determined that expression of sheep A3 adenosine receptor subtype transcripts is abundant in the sheep lung. Using in-situ hybridization methodology, we disclose herein the expression of the A3 adenosine receptor subtype on eosinophils in the submucosa of asthmatic or atopic human lung and in sheep lung. For both species, we detected no hybridization in the epithelium, endothelium, smooth muscle or glands. Using reverse transcriptase polymerase chain reaction, we have detected changes in adenosine receptor subtype expression on human eosinophils cultured in the presence of the cytokine GM-CSF. Specifically, we have discovered that A3 transcripts are upregulated 10-fold and A2b transcripts are up-regulated 3 to 4-fold under these conditions. In contrast, we have discovered that the level of A2a and A1 subtype transcript expression remained unchanged. The cytokine-induced increase in adenosine receptor transcript expression demonstrates the importance of these receptor subtypes in activated eosinophil function, and indicates that cytokines induce hypersensitivity of eosinophils to adenosine through up-regulation of the A3 and A2b adenosine receptors. The A3 receptor is negatively coupled to adenylate cyclase through its G-protein, while the A2b receptor is positively coupled. However, since the A2b receptor is a low affinity adenosine receptor and the A3 receptor is a high affinity receptor, except in high concentrations of adenosine, the principal effect of adenosine agonism on eosinophils will be through the A3 receptor subtype. Thus, decreases in eosinophil intracellular cAMP and subsequent mediator release is associated with exposure of eosinophils to cytokines, including GM-CSF, interferon IL-3 and IL-5. Thus, one object of this invention is to provide a method to overcome this cytokine induced eosinophil hypersensitivity to adenosine which comprises contacting eosinophils with an antagonistically effective amount of an A3 adenosine receptor subtype specific antagonist.

Mediation at the A3 and/or A2b adenosine receptor subtypes affects the proinflammatory state of activated eosinophils. Intervention at A3 receptors on eosinophils therefore has therapeutic potential for allergic and inflammatory diseases including asthma, hypersensitivity, rhinitis, hay fever, serum sickness, allergic vasculitis, dermatitis, psoriasis, eczema, atopic dermatitis, idiopathic pulmonary fibrosis, eosinophillic cholecystitis, chronic airway inflammation, eosinophillic gastroenteritis, edema and urticaria, eosinophillic myocardial disease, episodic angioedema with eosinophillia, inflammatory bowel disease, hypereosinophilic syndromes, ulcerative colitis, allergic granulomatosis, carcinomatosis, eosinophilic granuloma and familial histiocytosis.

Accordingly, this invention provides a method for achieving specific blockade of the A3 subtype of the adenosine receptor on eosinophils.

The method of this invention provides a means for preventing or treating disease states associated with activation of the A3 subtype of the adenosine receptor on eosinophils. The method comprises contacting said receptor with an amount of a compound which selectively blockades activation of the A3 adenosine receptor subtype. In one embodiment of the invention, xanthine or a xanthine derivative is used to effect a reduction in eosinophil activation without any substantial effect (binding or blockade) of the A1, A2a or A2b subtypes of the adenosine receptor. The method extends to the treatment or prevention of disease states mediated through activation of the A3 subtype of the adenosine receptor on eosinophils. Prevention of agonist induced eosinophil activation through blockade of the A3 subtype of the adenosine receptor by contacting eosinophils with an antagonistically effective amount of a xanthine or xanthine derivative specific for the A3 receptor subtype therefore also forms part of this invention.

A cDNA from human striatum designated HS-21a that encodes a human A3 adenosine receptor has been cloned. The cDNA is homologous with rat [Meyerhof, W., Muller-Brechlin, R. and Richter, D. (1991) FEBS Lett. 284, 155–160; Zhou, Q-Y, Chuanyi, L., Olah, M. E., Johnson, R. A., Stiles, G. L. and Civelli, O. (1992) Proc. Natl. Acad. Sci. U.S.A. 89 7432–7436] and sheep clones [Linden, J. Taylor, H. E., Robeva, A. S., Tucker, A. L., Stehle, J. H., Rivkees, S. A., Fink, S. J. and Reppert, S. M., (1993) Mol. Pharm. 44:524–532], and all three sequences encode receptors that couple adenosine induced inhibition of cAMP accumulation when stably expressed in CHO cells. $^{125}$I-ABA, previously used as a radioligand for A1 adenosine receptors [Linden, J., Patel, A. and Sadek, S. (1985) Cir. Res. 56, 279–284], was found to be suitable for detecting recombinant human A3 adenosine receptors expressed in CHO cells.

The sheep A3 adenosine receptor transcript is widely distributed, with high levels found in lung and spleen and moderate levels found in brain, pineal and testis. In marked contrast, the rat A3 adenosine receptor transcript is found primarily in testis. The human transcript is found to be more similar to the sheep than the rat homolog, with high expression in lung, moderate expression in brain and low expression in testis [Salvatore et al., P.N.A.S. 90:10365–10369, November 1993].

The rat A3 adenosine receptor differs from the human and sheep receptors in that it was reported not to bind the xanthine antagonists, XAC and DPCPX [Zhou, Q-Y, Chuanyi, L., Olah, M. E., Johnson, R. A., Stiles, G. L. and Civelli, O. (1992) Proc. Natl. Acad. Sci. U.S.A. 89 7432–7436]. The sheep and the human A3 adenosine receptors bind both antagonists and also have high affinity for 8-substituted xanthines having acidic substitutions. At the same time that the acidic substitutions increase the binding affinity of these compounds for the A3 receptor, they decrease the affinity for the A1, A2a and A2b subtypes. A limited number of xanthine analogs were evaluated in the pharmacological characterization of the rat A3 receptor and it was reported that these compounds do not significantly bind to the rat A3 receptor. The opposite is true in the case with the sheep A3 homolog and the human A3 receptor which has a high affinity for this class of compounds.

A few significant differences in ligand binding and transcript expression exist between the human and sheep receptors. I-ABA appears to be a full and partial agonist, respectively, for lowering cyclic AMP in CHO cells transfected with sheep and human receptors. The human receptor has higher affinity for CPA in comparison to the sheep receptor. An agonist affinity order of I-ABA>NECA>R-PIA>S-PIA>>CPA was established for the sheep receptor [Linden, J. Taylor, H. E., Robeva, A. S., Tucker, A. L., Stehle, J. H., Rivkees, S. A., Fink, S. J. and Reppert, S. M., (1993) Mol. Pharm. 44:524–532]. By comparison, the human receptor has a generally higher affinity for all of the agonists and a preference for CPA over S-PIA, resulting in an agonist profile of I-ABA>NECA>R-PIA>CPA>S-PIA.

The antagonist affinity order profiles are similar between human and sheep receptors. However, the human receptor exhibits a higher affinity for XAC. 8-Phenylxanthines with para-acidic residues were found to bind with high affinity to sheep A3 adenosine receptors [Linden, J. Taylor, H. E., Robeva, A. S., Tucker, A. L., Stehle, J. H., Rivkees, S. A., Fink, S. J. and Reppert, S. M., (1993) Mol. Pharm. 44:524–532]. Included among these are compounds with various 3-substitutions that were evaluated previously as potent antagonists of A1 adenosine receptors [Linden, J., Patel, A., Earl, C. Q., Craig, R. H. and Daluge, S. M. (1988) J. Med. Chem. 31, 745–751]. One of these compounds, I-ABOPX, was found to have the highest affinity as an A3 adenosine receptor antagonist, with a $K_i$ of 18 nM for the human receptor and 2 nM for the sheep receptor.

The potency order profiles of agonist and antagonist binding to the A3 receptor differ substantially from the profiles established for the other cloned human adenosine receptor subtypes [Linden, J., Jacobson, M. A., Hutchins, C. and Williams, M. (1994) Adenosine Receptors in *Handbook of Receptors and Channels*, Vol 1. G Protein-Linked Receptors, ed Peroutka, D. J. (CRC Press, Boca Raton. Fla.), p.29–43]. Pharmacologically, the A3 receptors appear to more closely resemble A1 than the A2 and consistent with the fact that the human A3 sequence is more similar to the A1 subtype (identity score 49%) than to the A2a and A2b subtypes. All subtypes of human adenosine receptors are blocked by xanthine antagonists such as BW-A1433, XAC and DPCPX, but differ in their affinities and potency order profiles for these ligands. The A1 subtype has high affinity for agonists with saturated rings in the $N^6$ position of the adenine ring, and xanthine antagonists with saturated rings in the $C^8$ position.

The human A3 receptor has a slightly higher affinity for ligands with unsaturated than saturated rings in the $N^6$ position of agonists (R-PIA>CPA) and in the $C^8$ position of xanthines (BW-A1433 and XAC>DPCPX). On the basis of structure-activity relationships of A1 agonists and antagonists, a model has been proposed in which the $N^6$-substituents of the adenine ring can be superimposed upon the $C^8$-regions of xanthines [Peet, N. P., Lentz, N. L., Meng, E. C., Dudley, M. W., Ogden, A. M. L., Demeter, D. A., Weintraub, H. J. R. and Bey, P. (1990) J. Med Chem. 33, 3127–3130; Van der Wenden, E. M., IJzerman, A. P. and Soudijn, W. (1992) J. Med Chem. 35, 629–635]. A similar relationship has been suggested to exist for the sheep A3 receptor since parallel changes in potency for agonists and antagonists were observed when the $N^6$ and $C^8$ positions, respectively were substituted with unsaturated or saturated rings [Linden, J. Taylor, H. E., Robeva, A. S., Tucker, A. L., Stehle, J. H., Rivkees, S. A., Fink, S. J. and Reppert, S. M., (1993) Mol. Pharm. 44:524–532]. The human A3 receptor was found to also exhibit corresponding changes in agonist and antagonist affinities when saturated substitutions were introduced at the $N^6$ and $C^8$ positions.

In one embodiment of this invention, an A3 adenosine receptor antagonist having a pKi for the A3 sutype of 7 or greater, and a pKi for other adenosine receptor subtypes of 6 or less is used to antagonize the A3 adenosine receptor on eosinophils.

Salvatore et al., [P.N.A.S. 90:10365–10369, November 1993] disclosed the following potencies for specific antagonists which may be used to inhibit the eosinophil A3 adenosine receptor according to this invention:

|  | BINDING pKi | cAMP pKi |
|---|---|---|
| Antagonists |  |  |
| IABOPX | 7.74 | 8.13 |
| XAC | 7.15 | 7.66 |
| BW-A1433 | 7.26 | 7.0 |
| DPCPX | 6.12 | 5.36 |

The use of a class of xanthines and their derivatives having the following characteristics is defined as having selective binding properties for the vertebrate (including sheep and human) eosinophil A3 adenosine receptor:

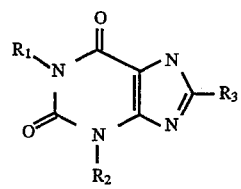

wherein $R_1$, $R_2$, and $R_3$, independently, are as defined below:

| $R_2$ | $R_2$ | R3 |
|---|---|---|
| alkyl | aryl | acidic aryl |
| alkenyl | substituted aryl | substituted acidic aryl |
| cycloalkyl | hetero-aryl |  |
|  | substituted hetro-aryl |  | wherein:

alkyl, alkenyl, cycloalkyl is substituted or unsubstituted aryl is benzyl, phenyl;

substituted aryl is an aryl substituted with an alkyl, amino or halogen; and acidic aryl is an aryl substituted with a carboxylate, oxyacetate, acrylate, sulphonate, phosphonate, or tetrazol.

In a preferred embodiment of this invention, the xanthine is:

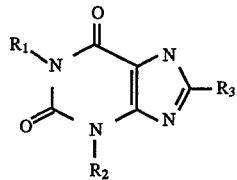

wherein $R_1$, $R_2$, and $R_3$, independently, are as defined below:

| $R_1$ | $R_2$ | R3 |
|---|---|---|
| lower alkyl | benzyl | benzyl-acid |
|  | halogenated benzyl |  |
|  | amino-benzyl |  |
|  | halogenated amino-benzyl. |  |

In a further embodiment, the xanthine is:

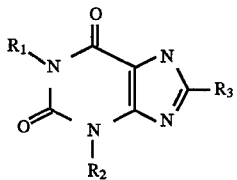

wherein $R_1$, $R_2$, and $R_3$, independently, are as defined below:

| $R_1$ | $R_2$ | R3 |
|---|---|---|
| —$C_3H_7$ | —$C_3H_7$ | —$CH_2$—$C_6H_4$—O-acid |
| —$CH_3$ | -benzyl | —$CH_2$—COO— |

-continued

| R₁ | R₂ | R3 |
|---|---|---|
| —C₂H₅ | -halogenated benzyl<br>-aminobenzyl<br>-halogenated aminobenzyl | -indole | wherein said acid is -indole, -carboxylate, sulphonate, phosphonate. In specific embodiments of the invention, the xanthine is selected from the group consisting of IABOPX, XAC, BW-A1433, DPCPX The abundant mRNA observed in the human and sheep lung is evidence that the A3 adenosine receptor subtype mediates a physiological action in the pulmonary system. Adenosine has been shown to mediate both vasodilation and vasoconstriction [Neely, C. F., Kadowitz, P. J., Lippton, H., Neiman, M. and Hyman, A. (1989) J. Pharmacol. Exp. Ther 250, 170–176; Konduri, G. G., Woodward, L. L., Mukhopadhyay, A. and Deshmukh, D. R. (1992) Am. Rev. Respir. Dis. 146, 670–676]. in the pulmonary vasculature. In asthmatics, but not in normal patients, adenosine produces bronchoconstriction which can be antagonized by theophylline [Cushley, M. J., Tattersfield, A. E. and Holgate, S. T. (1984) Am. Rev. Respir. Dis. 129, 380–384]. The established pharmacological profile for the A3 receptor in both the human and the sheep, and the availability of subtype selective ligands facilitates the identification of the physiological functions mediated by the eosinophil A3 adenosine receptor subtype and the treatment of disease states mediated through agonism of the eosinophil A3 adenosine receptor subtype.

Assays utilized to characterize adenosine receptor ligands were developed as follows: The human A1, A2a, A2b and A3 receptor subtype cDNAs were subcloned into the expression vectors pSVL (PHARMACIA), CMV5 (Mumby, et al. 1990, PNAS, 87:728–732) or pREP (INVITROGEN). Transient expression in COS7 cells (monkey kidney cell line, ATCC CRL 1651, ATCC, Rockville, Md.) was accomplished by transfection of the cloned adenosine receptor cDNAs under the control of the SV40 promoter into mammalian cells (e.g.,COS7). Membranes prepared from the transfected cells were utilized for the determination of binding affinity, selectivity and specificity of the human adenosine receptors for various ligands. Stable expression of the human adenosine receptors in mammalian cells (e.g., CHO, HEK 293) was achieved after integration of the transfected cDNA into the chromosomes of the host cells. These stable cell lines constituently express the cloned human adenosine receptors and can be propagated infinitely. Stable cell lines expressing the human adenosine subtype cDNAs individually can be used in the binding assay to measure the affinity and selectivity of the receptors for adenosine agonists, antagonists and enhancers.

Membranes prepared from transfected COS7 cells were utilized in a binding assay to measure the affinity of the human adenosine receptors for the radiolabeled adenosine agonists, [$^3$H]-cyclohexyladenosine (CHA), [$^3$H]-CGS21680 (2-(p-(2-carboxyethyl)-phenylamino)-5'-N-ethyl-carboxamidoadenosine), [$^3$H]-5'-N-ethylcarboxamido adenosine ([$^3$H]-NECA), or [$^{125}$I]-N$^6$-aminobenzyl adenosine ($^{125}$I-ABA). Monolayer cell culture of transfected COS7 cells were dissociated with 1 mM EDTA in phosphate buffered saline and resuspended in 5 mM Tris, pH7.6/10 mM MgCl$_2$. The cells were subjected to freeze-thaw lysis and the suspension was homogenized in a glass dounce homogenizer. The membranes were pelleted, resuspended in binding buffer, 50 mM Tris pH 7.6/10 mM MgCl$_2$ and incubated with adenosine deaminase before the binding assay. The binding assay was performed by incubating 50–100 mg of membranes with increasing concentrations of radiolabeled adenosine agonists. Bound ligand was separated from free ligand by filtration on a SKATRON CELL HARVESTER equipped with a receptor binding filtermat. Bound radioactivity was measured by scintillation counting. Substances which bind to or enhance binding to expressed human adenosine receptors in COS, CHO and HEK 293 cells can be identified in competition binding assays with radiolabeled adenosine or xanthine analogs. For the competition binding assay, membranes were incubated with 5nM [$^3$H]-CHA 5 nM [$^3$H]-CGS21680,10 nM [$^3$H]-NECA or 1 nM [$^{125}$I-ABA] and various concentrations of adenosine agonists or antagonists.

A transient expression system in Xenopus oocytes was established by microinjection of in vitro transcribed mRNA from the cloned adenosine receptor cDNAs. The expression system allows the measurement of the biological effects (i.e., changes in cAMP levels) upon activation of the expressed adenosine receptors with ligand binding. The cAMP levels are measured by a radioimmunoassay (RIANEN kit, DuPont/NEN) using the acetylation protocol. Activation of the expressed receptors by ligand binding are coupled to either increases or decreases in the intracellular cAMP levels dependent upon the subtype of adenosine receptor (Van Calker et al., (1979) J. Neurochem. 33:999–1003; Londos et al. (1980) Proc. Natl. Acad. Sci. U.S.A. 77:2551–2554). The activity of any potential adenosine receptor agonist can be evaluated by measuring the changes in cAMP levels in oocytes injected with adenosine receptor mRNA but not in uninjected or negative control injected oocytes. The activity of any potential adenosine receptor antagonist can be evaluated by determining the inhibition of the cAMP response induced by adenosine in oocytes injected with adenosine receptor transcripts but not negative control or uninjected oocytes. The changes in cAMP accumulation can alternatively be measured in stably transfected CHO cells expressing the human adenosine receptor subtypes.

The cAMP accumulation assay has a number of advantages over the binding assay established in the mammalian cell expression system as a screen for adenosine receptor modulating agents. The assay allows the measurement of a biological effect (i.e., changes in cAMP levels) resulting from the activation of the expressed receptors by ligand binding. The native agonist adenosine is utilized in the assay to activate the expressed receptors. The functionality of additional adenosine receptor subtypes identified by molecular cloning which may not have defined ligands for binding analysis can be evaluated with the natural agonist and without prior identification of a selective, high affinity, radiolabeled ligand.

According to the method of this invention, an adenosine A3 specific antagonist is administered in an amount effective to induce blockade of the receptor on eosinophils. The higher the affinity of the antagonist for the receptor, the lower the required dosage. Compounds having a pKi of greater than about 7 for the eosinophil A3 receptor and below about 6 for other adenosine receptor subtypes, may be administered by any effective means to achieve either localized or systemic contact of the antagonist with the target eosinophil A3 adenosine receptors. This might include intraveous, intramuscular, intrasynovial, intranasal, nebulized intrapulmanory, intraperitoneal or other common means for administration of therapeutic compounds. Dosages of between about 1 μg/kg and 10 mg/kg are envisioned, as necessary, to achieve the desired effect of eosinophil A3 adenosine receptor blockade.

The following examples are provided to further define but not to limit the invention defined by the foregoing description and the claims which follow:

EXAMPLE 1

STEP A:

In the first step of obtaining the partial cDNAs encoding the human A1 and A2a adenosine receptors, total RNA was extracted by homogenizing 2.3 g human ventricle in 20 ml 5M guanidine isothiocyanate, 0.1M sodium citrate, pH 6.3, 1 mM EDTA, pH 7.0, 5% beta-mercaptoethanol, and 0.5% sodium lauryl sarcosinate. The homogenate was centrifuged for 10 min. at 10,000 rpm and the resulting supernatant was layered onto a cushion of 5.7M CsCl/0.1M EDTA, pH 7.0. After 20 hrs. of centrifugation at 24,000 rpm, the resulting pellet was precipitated one time and then passed over an oligo(dT)-cellulose (PHARMACIA, Piscataway, N.J.) column to isolate poly(A)+ RNA.

An oligo(dT) primed library was synthesized from 5 µg of the poly(A)$^+$ human ventricle RNA using the YOU-PRIME cDNA SYNTHESIS KIT (PHARMACIA, Piscataway, N.J.). See Gubler and Hoffman Gene 25:263 (1983). The resulting double-stranded cDNA was ligated into λgt10 EcoRI arms (PROMEGA, Madison, Wis.) and packaged according to the GIGAPACK II GOLD PACKAGING EXTRACT protocol (STRATAGENE, La Jolla, Calif.). See Huynh et al. (1985) *DNA Cloning Techniques: A Practical Approach*, IRL Press, Oxford, p.49 and Kretz et al. Res. 17:5409.

The *E. coli* strain C600Hfl (PROMEGA, Madison, Wis.) was infected with library phage, plated on agar plates, and incubated at 37° C. The phage DNA was transferred to HYBOND-N nylon membranes (AMERSHAM, Arlington Heights, Ill.) according to the manufacturer's specifications.

Synthetic probes were constructed from overlapping oligonucleotides (A1 probe: 62+63, A2 probe: 52+53; see Table I for their sequences) based on the published dog A1 (RDC7) and A2a(RDC8) sequences (F. Libert, et al (1989) Science 244:569–572). The oligonucleotides were annealed and filled-in with $\alpha^{32}$P-dCTP (NEN, Wilmington, Del.) and Klenow enzyme. The filters were hybridized with the appropriate probe in 5×SSC, 30% formamide, 5×Denhardt's solution, 0.1% SDS, and 0.1 mg/ml sonicated salmon sperm DNA at 42° C., overnight. Following hybridization the filters were washed to a final stringency of 6×SSC at 50° C. and exposed to X-OMAT AR film (KODAK, Rochester, N.Y.) at −70° C. The resulting positives were plaque purified by two additional rounds of plating and hybridization. Insert DNA was excised with NotI and ligated into NotI digested pBLUESCRIPT H KS+ (STRATAGENE, La Jolla, Calif.). (Genebank # 52327) DNA sequences were determined by the SEQUENASE protocol (USBC, Cleveland, Ohio). See Tabor and Richardsaon, J. Biol. Chem. 264 pp 6447–6458. Two clones were isolated in these screens. The human ventricle A1 cDNA (hva1-3a) and human ventricle A2a cDNA (hva2-13) contain portions of coding sequences for proteins homologous to the reported dog A1 and A2a cDNAs, respectively. The coding region of the human A1 clone corresponds to nucleotides 482 through 981 (FIG. 2) and is 92% identical to the dog A1 sequence at the nucleotide level. The coding region of the human A2a clone corresponds to nucleotides 497 through 1239 (FIG. 4), and is 90% identical to the dog A2a sequence at the nucleotide level.

STEP B:

The human ventricle A1 adenosine receptor partial cDNA (hvA1-3a) is a 543 bp NotI fragment containing 23 bp 3' untranslated sequence and is 460 bp short of the initiation methionine based on sequence homology to the dog A1 cDNA. A modification of the 5' RACE (rapid amplification of cDNA ends) method (MA Frohman et al,(1988), Proc. Natl. Acad. Sci. U.S.A., 85:8998–9002) was used to generate the 5' coding region of the cDNA. First strand cDNA was synthesized from 1 µg of the human ventricle poly(A)$^+$ RNA in a total volume of 40 µl containing 50 mM Tris, pH 8.0, 140 mM KCl, 10 mM MgCl$_2$, 10 mM DTT, 15 mM each dNTP, 20 units RNasin (PROMEGA, Madison, Wis.), 20 pmol human primer 79 (see Table I), and 9.2 units AMV reverse transcriptase at 37° C. for 2 hrs. The reaction was then diluted to 120 ml with 0.5 mM Tris, pH 7.6/0.05 mM EDTA and passed through a SEPHACRYL S-300 SPUN COLUMN (PHARMACIA, Piscataway, N.J.). The product in the column effluent was polyadenylated in 100 mM potassium cacodylate, pH 7.2, 2mM CoCl$_2$, 0.2 mM DTT, 0.15 mM dATP, and 14 units terminal deoxynucleotidyl transferase in a total volume of 31 µl for 10 min. at 37° C. The reaction was terminated by heating at 65° C. for 15 min. and then diluted to 500 µl with 10 mM Tris, pH 8.0/1 mM EDTA (TE).

Ten µl of the poly(A)-tailed first strand cDNA was used as template in a primary PCR amplification reaction according to the GENEAMP protocol (PERKIN ELMER CETUS, Norwalk, Conn.; see Saiki et al. (1988) Science 239:487–491) containing 10 pmol primer 70, 25 pmol primer 71, and 25 pmol human primer 80 (see table I) in a total volume of 50 µl. Primer 70 is 5'-gactcgagtcgacatcga(t)$_{17}$, primer 71 is 5'-gactcgagtcgacatcga, and both are based on M. A. Frohman, et al (1988), Proc. Natl. Acad. Sci. U.S.A., 85:8998–9002. One cycle of PCR was performed of 1 min at 95° C., 2 min at 50° C., 40 min at 72° C., followed by 40 cycles of 40 sec at 94° C., 2 min at 56° C., 3 min at 72° C. The primary PCR amplification reaction product was electrophoresed through a 1.4% agarose gel and an area corresponding to approximately 600 bp was excised. The gel slice was melted and 1 µl was used as template in a secondary PCR amplification reaction containing 100 pmol primer 71 and human primer 81 (see Table I) for 30 cycles of 1 min at 94° C., 2 min at 56° C., 3 min at 72° C. The secondary PCR amplification product was digested with EcoRI and SalI and electrophoresed on a 1.4% agarose gel. An area corresponding to 500–600 bp was excised and ligated into EcoRI/SalI digested pBLUESCRIPT II KS+ (STRATAGENE, La Jolla, Calif.). The sequence of the 515 bp PCR product (5'HVA1-9) was determined by the SEQUENASE protocol (USBC, Cleveland, Ohio). The partial human ventricle A1 cDNA and the PCR product contain overlapping sequence and represent the complete coding region for the human A1 receptor, including 14 and 23 bp of 5' and 3' untranslated sequences, respectively. The sequence of the human A1 adenosine receptor cDNA so identified, is shown in FIG. 2.

STEP C:

A probe was generated by Klenow enzyme extension, including $\alpha^{32}$P-dCTP, of annealed oligonucleotides 62 and 63, and used to screen a human kidney cDNA library (CLONTECH, Palo Alto, Calif.). *E. coli* strain C600hfl (PROMEGA, Madison, Wis.) was infected with library phage and grown overnight on agar plates at 37° C. Phage DNA was transferred to HYBOND-N nylon filters according to the manufacturer's protocol (AMERSHAM, Arlington Heights, Ill.). The probe was incubated with the filters in 750 mM NaCl, 75 mM sodium citrate, 30% formamide, 0.1% sodium dodecyl sulfate, 0.5 mg/mL polyvinylpyrrolidone, 0.5 mg/mL bovine serum albumin, 0.5 mg/mL Ficoll 400, and 0.1 mg/mL salmon sperm DNA, at 42° C. overnight. The filters were washed in 0.9M NaCl and 90 mM sodium citrate at 50° C. A positively hybridizing phage (hkA1-14), was identified and purified by replating and screening with the probe twice more. The final phage plaque was transferred to 0.5 mL 50 mM Tris, pH 7.5, 8 mM MgSO$_4$, 85 mM NaCl, 1 mg/mL gelatin, and 1 µL of a 1:50 dilution in water of the phage stock was used as template for PCR amplification. 50 pmol each of 1 amL and 1 amR (Table I) oligonucleotide primers were included, and subjected to 30 cycles of 40 sec at 94° C., 1 min at 55°, 3 min at 72°, then a final 15 min at 72°, according to the GENEAMP protocol (PERKIN ELMER CETUS, Norwalk, Conn.). A 2.0 kb product was identified by agarose gel electrophoresis, and this was subcloned into the EcoRI site of pBLUESCRIPT II KS+ (STRATAGENE, La Jolla, Calif.). Sequence analysis by the SEQUENASE protocol (USBC, Cleveland, Ohio) demonstrated that this cDNA was homologous to the reported dog A1 clone. SmaI and EcoRI digestion released a DNA fragment containing coding sequence from base pair 76 through the translation STOP codon (FIG. 2) that is identical to the human ventricle A1 cDNA sequence (clones hva1-3a and 5'hva1-9). This fragment was used in construction of the full length coding sequence (see below). The human kidney cDNA also includes about 900 bp of 3' untranslated sequence.

STEP D:

The human ventricle A2a adenosine receptor partial cDNA (hvA2-13) is a 1.6 kb NotI fragment containing approximately 900 bp 3' untranslated sequence and is 496 bp short of the initiation methionine based on sequence homology to the dog A2a cDNA clone. Two consecutive rounds of 5' RACE were utilized to generate the 5' coding region of the cDNA. First strand cDNA was synthesized from 1 mg of the human ventricle poly(A)$^+$ RNA in a total volume of 40 ml containing 50 mM Tris, pH 8.0, 140 mM KCl, 10 mM MgCl$_2$, 10 mM DTT, 15 mM each dNTP, 20 units RNasin, 20 pmol human primer 68 or 74 (for 1st or 2nd round RACE respectively), and 9.2 units AMV reverse transcriptase at 37° C. for 2 hrs. The reaction was then diluted to 120 µl with 0.5 mM Tris, pH 7.6/0.05 mM EDTA and passed through a SEPHACRYL S-300 SPUN COLUMN. The products in the column effluents were polyadenylated in 100 mM potassium cacodylate, pH 7.2, 2 mM COCl$_2$, 0.2 mM DTT, 0.15 mM dATP, and 14 units terminal deoxynucleotidyl transferase in a total volume of 31 µl for 10 min. at 37° C. The poly(A) tailing reaction was terminated by heating at 65° C. for 15 min. and then diluted to 500 ml with TE.

Five or 10 µl (for 1st or 2nd round RACE respectively) of the poly(A) tailed first strand cDNA was used as template in the PCR amplification reaction according to the GENEAMP protocol containing 10 pmol primer 70, 25 pmol primer 71 (primer 70 and 71 sequences are given above), and 25 pmol human primer 69 or 75 (1 st or 2nd round RACE respectively; see Table I) in a total volume of 50 µl. One cycle of PCR was performed of 1 min at 95° C., 2 min at 50° C., 40 min at 72° C., followed by 40 cycles of 40 sec at 94° C., 2 min at 56° C., 3 min at 72° C. The PCR amplification products were digested with EcoRI and SalI and electrophoresed on a 1.4% agarose gel. Areas corresponding to 200–400 bp were excised and ligated into EcoRI/SalI digested pBLUESCRIPT II KS+ (STRATAGENE, La Jolla, Calif.). The sequences of the two A2a PCR products, the 332 bp 1 st round RACE product (5'hvA2-14) and the 275 bp 2nd round RACE product (5'hvA2-29) were determined by the SEQUENASE (USBC, Cleveland, Ohio) protocol. By sequence homology comparisons with the dog A2a adenosine receptor cDNA sequence, the 1st round RACE product (5'hvA2-14) was 258 bp short of the initiation methionine and the second round RACE product (5'HVA2-29) was determined to extend 1 bp upstream of the initiation methionine. The human ventricle A2a partial cDNA clone (hvA2-13) and the human A2a PCR products (5'hvA2-14 and 5hva2-29) contain overlapping sequence and together represent the complete coding sequence for the human adenosine A2a receptor, and include 1 bp and 0.8 kb of 5' and 3' untranslated sequence, respectively. The sequence of the human A2a adenosine receptor is shown in FIG. 4.

STEP E:

A double-stranded DNA probe was generated by Klenow enzyme extension, including $\alpha^{32}$P-dCTP, of annealed oligonucleotides 66 and 67, and used to screen a human striata cDNA library (STRATAGENE, La Jolla, Calif.). The oligonucleotide sequence was based on a region of the human ventricle A2a cDNA sequence. E. coli strain XL1-blue (STRATAGENE, La Jolla, Calif.) cells were infected with library phage and grown overnight on agar plates at 37° C. Phage DNA was transferred to HYBOND-N nylon filters according to the manufacturer's protocol (AMERSHAM, Arlington Heights, Ill.). The probe was incubated with the filters in 750 mM NaCl, 75 mM sodium citrate, 10% formamide, 0.5% sodium dodecyl sulfate, 0.5 mg/mL polyvinylpyrrolidone, 0.5 mg/mL bovine serum albumin, 0.5 mg/mL Ficoll 400, and 0.02 mg/mL salmon sperm DNA, at 42° C. overnight. The filters were washed in 0.9M NaCl and 90 mM sodium citrate at 50° C. A positively hybridizing phage (hbA2-22A) was identified and purified by replating and screening with the probe twice more, and subcloned into the plasmid pBLUESCRIPT SK- by the manufacturer's protocol (STRATAGENE, La Jolla, Calif.). See Short et al. (1988) Nucl. Acids Res. 16:7583–7600; Sorge (1988) Stratagies 1:3–7. The human brain A2a adenosine receptor cDNA (hbA2-22A) spans bp 43 of the A2 coding sequence (FIG. 4) through the translation STOP codon, and includes about 900 bp of 3' untranslated sequence. The sequence of this human brain A2a cDNA is identical to the human ventricle A2a adenosine receptor cDNA (hvA2-13, 5'hvA2-14 and 5'hvA2-29).

STEP F:

A double-stranded DNA probe was generated by Klenow enzyme extension of annealed oligonucleotides 129 and 130, including $\alpha^{32}$P-dCTP, and used to screen a human frontal cortex cDNA library (STRATAGENE, La Jolla, Calif.). The oligonucleotide sequence was based on a region of the human A2a and A1 cDNA sequence. E. coli strain XL-1 blue (STRATAGENE, La Jolla, Calif.) cells were infected with library phage and grown overnight at 37° C. Phage DNA was transferred to HYBOND-N nylon filters according to the manufacturer's protocol (AMERSHAM, Arlington Heights, Ill.). The probe was incubated with the filters in 750 mM NaCl, 75 mM sodium citrate, 10% formamide, 0.5% sodium dodecyl sulfate, 0.5 mg/mL polyvinyl-pyrrolidone, 0.5 mg/mL bovine serum albumin, 0.5 mg/mL Ficoll 400, and 0.02 mg/mL salmon sperm DNA, at 42° C. overnight. The filters were washed in 0.9M NaCl and 90 mM sodium citrate at 50° C. A positively hybridizing phage (hb-32c), was identified and purified by replating and screening with the probe twice more. The insert was subcloned to the plasmid pBLUESCRIPT SK- according to the manufacturer's protocol (STRATAGENE, La Jolla, Calif.). Sequence analysis by the SEQUENASE protocol (USBC, Cleveland, Ohio) demonstrated a complete open reading frame coding for amino acid sequence homologous to both of the previously isolated human A1 and A2a clones. This homologous adenosine receptor subtype cDNA is the A2b subtype having the sequences in FIGS. 5 and 6. A 1.3 kb SmaI-XmnI fragment was ligated into the SmaI site of pSVL (PHARMACIA, Piscataway, N.J.), giving the full length coding sequence of the A2b adenosine receptor in a plasmid suitable for its expression in COS and CHO cells. See Sprague et al. (1983) J. Virology 45:773; Templeton and Eckhart (1984) Mol. Cell Biol. 4:817.

Table I:

Sequences and directions of the primers used in the isolation of cDNA's and construction of expression plasmids, along with the positions in the clones upon which the sequences are based. Dog A1 and A2a cDNA clones are from F. Libert, et al, (1989) Science 244:569–572. Primers LamL and LamR are based on the sequence of λgt10 (T. V. Hyunh, et al. (1985) DNA Cloning: A Practical Approach, Vol 1, D. Glover, ed, IRL Press, Oxford). The A2b adenosine receptor subtype encoded by the clone hb32C was determined to be the A2b adenosine receptor subtype on the basis of the binding profile of the adenosine receptor agonist NECA. and affinities for adenosine receptor antagonists measured on membranes prepared from pSVLhb32C transfected COS7, CHO or HEK 293 cells.

| name | sequence | position | clone | direction |
|------|----------|----------|-------|-----------|
| 52 | ATTCGCAGCCACGTCCTGA-GGCGGCGGGAGCCCTTCAA-AGCAGGTGGCACCAGTGCC-CGC (SEQ ID NO. 1) | 1201–1260 | dog A2a | sense |
| 53 | GCGGAGGCTGATCTGCT-CTCCATCACTGCCATGAG-CTGCCAAGGCGCGGGCAC-TGGTGCC (SEQ. ID NO. 2) | 1305–1246 | dog A2a | antisense |
| 62 | TCCAGAAGTTCCGGGTCA-CCTTCCTTAAGATCTGGAA-TGACCACTTCCGCTGCCAGC-CCA (SEQ. ID NO. 3) | 958–1017 | dog A1 | sense |
| 63 | AGTCGTGGGGCGCCTCCT-CTGGGGGGTCCTCGTCGAC-GGGGGGCGTGGGCTGGCAG-CGGA (SEQ ID NO. 4) | 1062–1003 | dog A1 | antisense |
| 66 | GCCTCTTTGAGGATGTGG-TCCCCATGAACTACATGGT-GTACTTCA (SEQ ID NO. 5) | 500–542 | 5'hvA2-14 | sense |
| 67 | GCAGGGGCACCAGCACACA-GGCAAAGAAGTTGAAGTAC-ACCATGT (SEQ ID NO. 6) | 572–528 | 5'hva2-14 | antisense |
| 68 | TCGCGCCGCCAGGAAGAT (SEQ ID NO 7) | 616–599 | hva2-13 | antisense |
| 69 | TATATTGAATTCTAGACAC-CCAGCATGAGC (SEQ ID NO. 8) | 591–574 | hva2-13 | antisense |
| 74 | TCAATGGCGATGGCCAGG (SEQ ID NO. 9) | 303–286 | 5'hva2-14 | antisense |
| 75 | TATATTGAATTCATGGA-GCTCTGCGTGAGG- (SEQ ID NO. 10) | 276–259 | 5'hva2-14 | antisense |
| 79 | GTAGACCATGTACTCCAT (SEQ ID NO. 11) | 560–543 | hva1-3a | antisense |
| 80 | TATATTGAATTCTGACCT-TCTCGAACTCGC- (SEQ ID NO. 12) | 537–521 | hva1-3a | antisense |
| 81 | ATTGAATTCGATCACGGG-CTCCCCCATGC- (SEQ ID NO. 13) | 515–496 | hva1-3a | antisense |
| 129 | ATGGAGTACATGGTCTAC-TTCAACTTCTTTGTGTGGG-TGCTGCCCCCGCT- (SEQ ID NO. 14) | — | — | sense |
| 130 | GAAGATCCGCAAATAGACA-CCCAGCATGAGCAGAAGCG-GGGGCAGCACCC (SEQ ID NO. 15) | — | — | antisense |
| 131 | CCCTCTAGAGCCCAGCCTGT-GCCCGCCATGCCCATCATGG-GCTCC (SEQ ID NO. 16) | 2–19<br>1–14 | 5'hva2-29<br>5'hva1-9 | sense |
| 1amL | CCCACCTTTTGAGCAAGTTC (SEQ ID NO. 17) | — | λt10 | — |
| 1amR | GGCTTATGAGTATTTCTTCC (SEQ ID NO. 18) | — | λt10 | — |
| 207 | CCCAAGCTRATGAAAGCCAA CAATACC (SEQ ID NO. 27) | | | |
| 208 | TGCTCTAGACTCTGGTATCT TCACATT (SEQ ID NO. 28) | | | |

EXAMPLE 2

Human A1 adenosine receptor expression construct:

To express the human adenosine receptor cDNA in COS, CHO and HEK 293 cells, the 118 bp SalI-SmaI fragment of the human ventricle A1 PCR product (5'HVA1-9) was ligated together with the 1.8 SmaI-EcoRI fragment of the human kidney A1 adenosine receptor cDNA (hkA1-14) and the 3.0 kb SalI-EcoRI fragment of pBLUESCRIPT II KS+, resulting in a plasmid containing the contiguous full length coding sequence for the human A1 adenosine receptor cDNA and some 5' and 3' untranslated sequence. This plasmid was digested first with EcoRI, the resulting ends were filled in by Klenow enzyme extension and then the plasmid was digested with XhoI to release a fragment of 1.9 kb containing the full length human A1 adenosine receptor cDNA. The fragment was subcloned into the expression vector pSVL (PHARMACIA) which had been digested with XhoI-SmaI.

Human A2a adenosine receptor expression construct:

To express the human A2a adenosine receptor cDNA in COS, CHO or HEK 293 cells, a contiguous A2a cDNA sequence was constructed before subcloning into the expression vector, pSVL. Primer 131, containing an XbaI recognition site, 14 bp of 5' untranslated sequence of human A1 adenosine receptor cDNA, and the first 18 bp of human A2a adenosine receptor cDNA coding sequence was used with primer 75 in PCR with 1 ng of the plasmid containing the human ventricle A2a 2nd round RACE product (5'hvA2-29) as template. Twenty-five cycles of 40 sec at 94° C., 1 min at 55° C., and 3 min at 72° C., then a final incubation of 15 min at 72° C., with 1 ng of plasmid template and 50 pmol of each primer in a volume of 50 according to the GENEAMP protocol (PERKIN ELMER CETUS, Norwalk, Conn.), resulted in the expected 302 bp product determined by agarose gel electrophoresis. The 172 bp XbaI-EagI digestion product of this DNA fragment was ligated together with 1125 bp EagI-BglII digestion product of the human striata A2a adenosine receptor cDNA (hbA2-22A) and XbaI-SmaI digested pSVL (PHARMACIA), generating the full length human A2a adenosine receptor cDNA coding sequence in a plasmid suitable for its expression in COS, CHO or HEK 293 cells.

Mammalian cell expression:

COS7 cells (ATCC #1651-CRL) were grown in complete medium, Dulbecco's modified Eagles's medium, DMEM (GIBCO, Grand Island, N.Y.) containing 10% fetal bovine serum, 100 U/mL penicillin-streptomycin and 2 mM glutamine, in 5% $CO_2$ at 37° C. Transient transfection of COS7 cells was performed by the $CaPO_4$ method (Graham, F. L. and Van Der Erb, A. J. (1973) Virology 52:456–567) using the Mammalian Transfection Kit (STRATAGENE). See Chen and Okayama Mol. Cell Biol. 7:2745–2752. Plasmid DNA (15 μg) was precipitated with 125 mM $CaCl_2$ in BBS (N,N-bis(2-hydroxyethyl)-2-aminoethanesulfonic acid buffered saline) at room temperature for 30 minutes. The DNA precipitate was added to the COS7 cells and incubated for 18 h in 5% $CO_2$ at 37° C. The precipitate was removed and the cells were washed twice with serum free DMEM. Cells were incubated in complete medium in 5% $CO_2$ at 37° C. for 48 h prior to the binding assay.

Stable expression in CHO or HEK 293 cells:

To establish stable cell lines, CHO or HEK 293 cells were co-transfected with 20 μg of pSVL containing the adenosine receptor cDNA and 1 μg of pWLneo (STRATAGENE) containing the neomycin gene. See Southern and Berg (1982) J. Mol. App. Gen. 1:327–341. Transfection was performed by the $CaPO_4$ method. DNA was precipitated at room temperature for 30 minutes, added to the CHO cells and incubated 18 h in 5% $CO_2$ at 37° C. The precipitate was removed and the cells were washed twice with serum free DMEM. Cells were incubated for 24 h in 5% $CO_2$ at 37° C., replated in 24-well dishes at a dilution of 1:10, and incubated an additional 24 h before adding selection medium, DMEM containing 10% fetal bovine serum, 100 U/mL penicillin-streptomycin, 2 mM glutamine and 0.5 mg/mL G418 (GIBCO). Transfected cells were incubated at 5% $CO_2$, 37° C. until viable colonies were visible, approximately 14–21 days. Colonies were selected and propagated. The cell clone with the highest number of human adenosine receptors was selected for subsequent application in the binding assay.

EXAMPLE 3

Binding studieS;

Membranes were prepared from transiently transfected COS7 cells 48 h after transfection or from G418-selected stably transfected CHO or HEK 293 cells. Cells were harvested in 1 mM EDTA in phosphate buffered saline and centrifuged at 2000×g for 10 minutes. The cell pellet was washed once with phosphate buffered saline. The cell pellet was resuspended in 2 mL of 5 mM Tris, pH 7.6/5 mM $MgCl_2$. Membranes were prepared from the cells by freeze-thaw lysis in which the suspension was frozen in a dry ice/ethanol bath and thawed at 25° C. twice. The suspension was homogenized after adding an additional 2 mL of 5 mM Tris, pH 7.6/5 mM $MgCl_2$, in a glass dounce homogenizer with 20 strokes. The membranes were pelleted at 40,000×g at 4° C. for 20 minutes. The membrane pellet was resuspended at a protein concentration of 1–2 mg/mL in binding assay buffer, 50 mM Tris, pH 7.6/10 mM $MgCl_2$. Protein concentration was determined by the method of Bradford ((1976) Anal. Biochem. 72: 248–250). Before the binding assay was performed, the membranes were incubated with adenosine deaminase (BOEHRINGER MANNHEIM), 2 U/mL for 30 minutes at 37° C. Saturation binding of [$^3$H]-cyclohexyladenosine (CHA) was performed on membranes prepared from pSVLA1 transfected COS7 or CHO cells.

Membranes (100 μg) were incubated in the presence of 0.2 U/mL adenosine deaminase with increasing concentrations of CHA (NEN, 32 Ci/mmol) in the range of 0.62–30 nM for 120 minutes at 25° C. in a total volume of 500 μL. The binding assay was terminated by rapid filtration and three washes with ice-cold 50 mM Tris, pH 7.6/10 mM $MgCl_2$ on a SKATRON CELL HARVESTER equipped with a receptor binding filtermat (SKATRON INSTRUMENTS, INC). Non-specific binding was determined in the presence of 100 μM $N^6$-cyclopentyladenosine (CPA). Bound radioactivity was measured by scintillation counting in READY SAFE SCINTILLATION COCKTAIL (BECKMAN). For competition binding experiments, membranes were incubated with 5 nM [$^3$H]-CHA and various concentrations of A1 adenosine receptor agonists. Saturation binding of [$^3$H] CGS-21680 was performed on membranes prepared from pSVLA2a transfected COS7 cells. Membranes (100 mg) were incubated in the presence of 0.2 U/mL s adenosine deaminase with increasing concentrations of CGS21680 (NEN, 48.6 Ci/mmol) in the range of 0.62–80 nM for 90 minutes at 25° C. in a total volume of 500 μL. The binding assay was terminated by rapid filtration with three washes with ice-cold 50 mM Tris, pH 7.6/10 mM $MgCl_2$ on a Skatron cell harvester equipped with a receptor binding filtermat (SKATRON INSTRUMENTS, INC). Non-specific binding was determined in the presence of 100 μM CPA.

Bound radioactivity was measured by scintillation counting in READY SAFE LIQUID SCINTILLATION COCKTAIL (BECKMAN). For competition binding experiments, membranes were incubated with 5 nM [$^3$H]-CGS21680 and various concentrations of A2 adenosine receptor agonists.

Saturation binding of [$^3$H]5'-N-ethylcarboxamidoadenosine (NECA) was performed on membranes (100 µg) prepared from pSVLhb32C (A2b) transfected COS7 cells in the presence of adenosine deaminase with increasing concentrations of NECA (NEN, 15.1 Ci/mmol) in the range of 1.3–106 nM for 90 minutes at 25° C. in a total volume of 500 µL. The assay was terminated by rapid filtration and three washes with ice-cold binding buffer on a cell harvester equipped with a receptor binding filtermat (SKATRON INSTRUMENTS, INC). Bound radioactivity was measured by scintillation counting. Non-specific binding was measured on membranes prepared from non-transfected COS7 cells. For competition binding experiments, membranes from transfected cells were incubated with 10 nM [$^3$H]NECA and varying concentrations of adenosine receptor antagonists.

EXAMPLE 4

The human A3 adenosine receptor was cloned from a human striata cDNA library. Oligonucleotide probes were designed based on the rat A3 sequence of Zhou et al., Proc. Natl. Acad. Sci. 89, 7432 (1992). The complete sequence of the human A3 adenosine receptor was determined and the protein sequence deduced. The cloned human A3 adenosine receptor is expressed in a heterologous expression system in COS, CHO and HEK 293 cells. Radiolabeled adenosine receptor agonists and antagonists are used to measure the binding properties of the expressed receptor. Stable cell lines can be used to evaluate and identify adenosine receptor agonists, antagonists and enhancers.

STEP A:

A synthetic probe homologous to the rat A3 adenosine receptor was generated using the polymerase chain reaction (PCR). Three Ml of rat brain cDNA was used as template in a PCR amplification reaction according to the GENEAMP protocol (PERKIN ELMER CETUS, Norwalk, Conn.) containing 50 pmol of primers 207 (5'-cccaagcttatgaaagccaacaatacc) (SEQ. ID NO: 27) and 208 (5'-tgctctagactctggtatcttcacatt) (SEQ. ID NO: 28) in a total volume of 50 Ml. Primers 207 and 208 are based on the published rat A3 adenosine receptor sequence (Zhou, et al, (1992), Proc. Natl. Acad. Sci. U.S.A., 89:7432–7406). Forty cycles of 40 sec at 94° C., 1 min at 55° C., 3 min at 72° C. were performed and the resulting 788 bp fragment was subcloned into HindIII-XbaI digested pBLUESCRIPT II KS+ (STRATAGENE, La Jolla, Calif.). The sequence was verified by the SEQUENASE protocol (USBC, Cleveland, Ohio).

STEP B:

The 788 bp PCR fragment was labeled with $\alpha^{32}$P-dCTP using the MULTIPRIME DNA LABELLING SYSTEM (AMERSHAM, Arlington Heights, Ill.) and used to screen a human striata cDNA library (STRATAGENE, La Jolla, Calif.). E. coli strain XL-1 Blue (STRATAGENE, La Jolla, Calif.) cells were infected with library phage and grown overnight at 37° C. Phage DNA was transferred to HYBOND-N nylon filters according to the manufacturer's protocol (AMERSHAM, Arlington Heights, Ill.). The probe was incubated with the filters in 5× SSC, 30% formamide, 5× Denhardt's solution, 0.5% sodium dodecyl sulfate, and 50 Mg/ml sonicated salmon testis DNA. The filters were washed in 2× SSC at 55° C. A positively hybridizing phage (HS-21a) was identified and plaque purified by two additional rounds of plating and hybridization. The insert was subcloned to the plasmid pBLUESCRIPT II SK- according to the manufacturer's protocol (STRATAGENE, La Jolla, Calif.). Upon sequence analysis using the SEQUENASE protocol (USBC, Cleveland, Ohio) it was determined that clone HS-21a contained the complete open reading frame corresponding to the human homolog of the rat A3 adenosine receptor. The coding region of the human A3 adenosine receptor cDNA is 78% identical to the rat sequence at the nucleotide level and contains 265 bp and 517 bp of 5' and 3' untranslated sequence, respectively. The 1.7 kb fragment was excised using sites present in the multiple cloning site of pBLUESCRIPT II SK- (STRATAGENE, La Jolla, Calif.) and subcloned into XhoI/SacI digested pSVL (PHARMACIA, Piscataway, N.J.) for its expression in COS and CHO cells.

EXAMPLE 5

Mammalian cell expression:

COS7 cells (ATCC #1651-CRL) were grown in complete medium, Dulbecco's modified Eagles's medium, DMEM (GIBCO, Grand Island, N.Y.) containing 10% fetal bovine serum, 100 U/mL penicillin-streptomycin and 2 mM glutamine, in 5% $CO_2$ at 37° C. Transient transfection of COS7 cells was performed by the $CaPO_4$ method (Graham, F. L. and Van Der Erb, A. J. (1973) Virology 52:456–567) using the Mammalian Transfection Kit (STRATAGENE). Plasmid DNA (15 µg) was precipitated with 125 mM $CaCl_2$ in BBS (N,N-bis(2-hydroxyethyl)-2-aminoethanesulfonic acid buffered saline) at room temperature for 30 minutes. The DNA precipitate was added to the COS7 cells and incubated for 18 h in 5% $CO_2$ at 37° C. The precipitate was removed and the cells were washed twice with serum free DMEM. Cells were incubated in complete medium in 5% $CO_2$ at 37° C. for 48 h prior to the binding assay.

Stable expression in CHO cells:

To establish stable cell lines, CHO cells were cotransfected with 20 µg of pSVL containing the adenosine receptor cDNA and 1 mg of pWLneo (STRATAGENE) containing the neomycin gene. Transfection was performed by the $CaPO_4$ method. DNA was precipitated at room temperature for 30 minutes, added to the COS7 cells and incubated 18 h in 5% $CO_2$ at 37° C. The precipitate was removed and the cells were washed twice with serum free DMEM. Cells were incubated for 24 h in 5% $CO_2$ at 37° C., replated in 24-well dishes at a dilution of 1:10, and incubated an additional 24 h before adding selection medium, DMEM containing 10% fetal bovine serum, 100 U/mL penicillinn-streptomycin, 2 mM glutamine and 1.0 mg/mL G418 (GIBCO). Transfected cells were incubated at 5% $CO_2$, 37° C. until viable colonies were visible, approximately 14–21 days. Colonies were selected and propagated. The cell clone with the highest number of human adenosine receptors was selected for subsequent application in the binding assay.

EXAMPLE 6

Binding assay:

Membranes were prepared from transiently transfected COS7 cells 48 h after transfection or from G418-selected stably transfected CHO or HEK 293 cells. Cells were harvested in 1 mM EDTA in phosphate buffered saline and centrifuged at 2000×g for 10 minutes. The cell pellet was washed once with phosphate buffered saline. The cell pellet was resuspended in 2 mL of 5 mM Tris, pH 7.6/5 mM $MgCl_2$. Membranes were prepared from the cells by freeze-thaw lysis in which the suspension was frozen in a dry ice/ethanol bath and thawed at 25° C. twice. The suspension was homogenized after adding an additional 2 mL of 5 mM Tris, pH 7.6/5 mM $MgCl_2$, in a glass dounce homogenizer with 20 strokes. The membranes were pelleted at 40,000×g at 4° C. for 20 minutes. The membrane pellet was resuspend at a protein concentration of 1–2 mg/mL in binding assay buffer, 50 mM Tris, pH 7.6/10 mM $MgCl_2$. Protein concentration was determined by the method of Bradford ((1976) Anal. Biochem. 72: 248–250). Before the binding assay was performed, the membranes were incubated with adenosine deaminase (BOEHRINGER MANNHEIM), 2 U/mL for 30 minutes at 37° C. Saturation binding of $[^{125}I]$-$N^6$-aminobenzyladenosine ($^{125}I$-ABA) or $[^{125}I]$-$N^6$-2-(4-amino-3-iodophenyl)ethyladenosine (APNEA) was performed on membranes prepared from pSVLA3 transfected COS7 cells. Membranes (100 μg) were incubated in the presence of 0.2 U/mL adenosine deaminase with increasing concentrations of $^{125}I$-ABA in the range of 0.1–30 nM for 120 minutes at 25° C. in a total volume of 500 μL. The binding assay was terminated by rapid filtration and three washes with ice-cold 50 mM Tris, pH 7.6/10 mM $MgCl_2$ on a Skatron cell harvester equipped with a receptor binding filtermat (SKATRON INSTRUMENTS, INC). Non-specific binding was determined on non-transfected cells. Bound radioactivity was measured by scintillation counting in Ready Safe Scintillation Cocktail (BECKMAN).

EXAMPLE 7

In vitro transcription and oocyte expression:

The 1.3 kb XhoI-BamHI fragment of the pSVL expression construct (described in Example 2) containing the full length human A2a adenosine receptor coding sequence was ligated into SalII-SpeI digested pGEMA (Swanson, et al, (1990) Neuron 4:929–939). The resulting plasmid, pGEMA2, was linearized with NotI, forming a template for in vitro transcription with T7 RNA polymerase. The homologous adenosine receptor subtype cDNA in pBluescript SK- was used as a template for in vitro transcription by T3 polymerase after removal of most of the 5' untranslated region, with the exception of 20 bp, as a 0.3 kb SmaI fragment. The $K^+$ channel cDNA, Kv3.2b was employed as a negative control in the cAMP accumulation assay. The generation of Kv3.2b RNA was described by Luneau, et al, ((1991) FEBS Letters 1:163–167). Linearized plasmid templates were used with the STRATAGENE mCAP kit according to the manufacturer's protocol, except that the SP6 RNA polymerase reaction was performed at 40° C. Oocytes were harvested from mature female *Xenopus laevis*, treated with collagenase, and maintained at 18° C. in ND96 medium (GIBCO) supplemented with 1 mM sodium pymvate and 100 μg/mL gentamycin. Fifty nanoliters (10 ng) of RNA diluted in $H_2O$ was injected and oocytes were incubated at 18° C. for 48 hours.

EXAMPLE 8 cAMP accumulation assay in oocytes:

Oocytes injected with either human adenosine receptor transcript or the Kv3.2b transcript were transferred to fresh medium supplemented with 1 mM of the phosphodiesterase inhibitor, Ro 20-1724 (RBI, Natick, Mass.) and 1 mg/mL bovine serum albumin incubated for 30 minutes and transferred to an identical medium with or without the agonist adenosine (10 mM) for an additional 30 minutes at room temperature. Groups of 5–10 oocytes were lysed by transfer to ND96/100 mM HCl/1 mM Ro 20-1724 in microfuge tubes, shaken, incubated at 950° C. for 3 min, and centrifuged at 12000 g for 5 min. Supernatants were stored at −70° C. before cAMP measurements. Cyclic AMP levels were determined by radioimmunoassay (RIANEN kit, DuPont/NEN) using the acetylation protocol. The adenosine receptor antagonist, 8-(p-sulfophenyl)theophylline (100 μM) was utilized to inhibit the cAMP response induced by adenosine in oocytes expressing the adenosine receptors.

EXAMPLE 9 cAMP accumulation in stable CHO cell lines:

The changes in cAMP accumulation can alternatively be measured in stably transfected CHO cells expressing the human adenosine receptor subtypes. CHO cells are washed twice in phosphate buffered saline (PBS) and detached in 0.2% EDTA in PBS. The cells are pelleted at 800 rpm for 10 min and resuspended in KRH buffer (140 mM NaCl/5 mM KCl/2 mM $CACl_2$/1.2 mM $MgSO_4$/1.2 mM $KH_2PO_4$/6 mM glucose/25 mM Hepes buffer, pH 7.4). The cells are washed once in KRH buffer and resuspended at $10^7$ cells/mL. The cell suspension (100 μL) is mixed with 100 μL of KRH buffer containing 200 μM Ro 20-1724 and incubated at 37° C. for 10 minutes. Adenosine (10 μM) was added in 200 μL KRH buffer containing 200 μM Ro 20-1724 and incubated at 37° C. for 20 minutes. After the incubation, 400 μL of 0.5 mM NaOAc (pH 6.2) was added and the sample was boiled for 20 minutes. The supernatant was recovered by centrifugation for 15 minutes and stored at −70° C. cAMP levels were determined by radioimmunoassay (RIANEN kit, DuPont/NEN) using the acetylation protocol. The effect of antagonists on cAMP accumulation are measured by preincubation for 20 minutes before adding adenosine.

EXAMPLE 10

Expression Construct and Transfection

The 1.7 kb HS-21a cDNA (A3) was subcloned as a SalI-BamHI fragment into the expression vector pCMV5 (Mumby, S. M., Heukeroth, R. O., Gordon, J. I. and Gilman, A. G. (1990) Proc. Natl. Acad. Sci. U.S.A. 87, 728–732.) creating the vector pCMV5-A3. CHO or HEK 293 cells stably expressing the human HS-21a cDNA were prepared by co-transfection of 15 μg pCMV5-A3 and 1 μg pWLneo (Stratagene) using the calcium phosphate method. Stable cell lines were also generated using EBV based mammalian expression vectors, pREP (INVITROGEN). Neomycin resistant colonies were selected in 1 mg/mL G418 (GIBCO). Stable colonies were screened for expression of HS-21a by $^{125}I$-ABA binding.

EXAMPLE 11

Binding Studies

Membranes were prepared from stable CHO cell lines in 10 mM Hepes, pH 7.4 containing 0.1 mM benzamidine and 0.1 mM PMSF as described (Mahan, L. C., et al., (1991) Mol. Pharmacol. 40, 1–7). Pellets were resuspended in 5 mM Hepes, pH 7.4/5 mM $MgCl_2$/0.1 mM benzamidine/0.1 mM PMSF at a protein concentration of 1–2 mg/mL and were incubated with adenosine deaminase (Boehringer Mannheim), 2 U/mL at 37° C. for 20 minutes. Saturation binding of $^{125}I$-ABA was carded out on 50 μg of membranes for 120 minutes at 25° C. in a total volume of 100 μL. The assay was terminated by rapid filtration and three washes with ice-cold binding buffer on a Skatron harvester equipped with a receptor binding filtermat (Skatron Instruments, INC). The specific activity of $^{125}I$-ABA, initially 2,200

Ci/mmol, was reduced to 100 Ci/mmol with nonradioactive I-ABA for saturation analysis. Nonspecific binding was measured in the presence of 1 μM I-ABA. The $K_D$ and $B_{max}$ values were calculated by the EBDA program (McPherson, G. A. (1983) Computer Programs for Biomedicine 17, 107–114). Competition binding of agonists and antagonists was determined with $^{125}$I-ABA (0.17–2.0 nM, 2000 Ci/mmol). Nonspecific binding was measured in the presence of 400 μM NECA. Binding data were analyzed and competition curves were constructed by use of the nonlinear regression curve fitting program Graph PAD InPlot, Version 3.0 (Graph Pad Software, San Diego). $K_i$ values were calculated using the Cheng-Prusoff derivation (Cheng, Y. C. and Prusoff, H. R. (1973) Biochem. Pharmacol. 22, 3099–3108.).

Figure 11A:
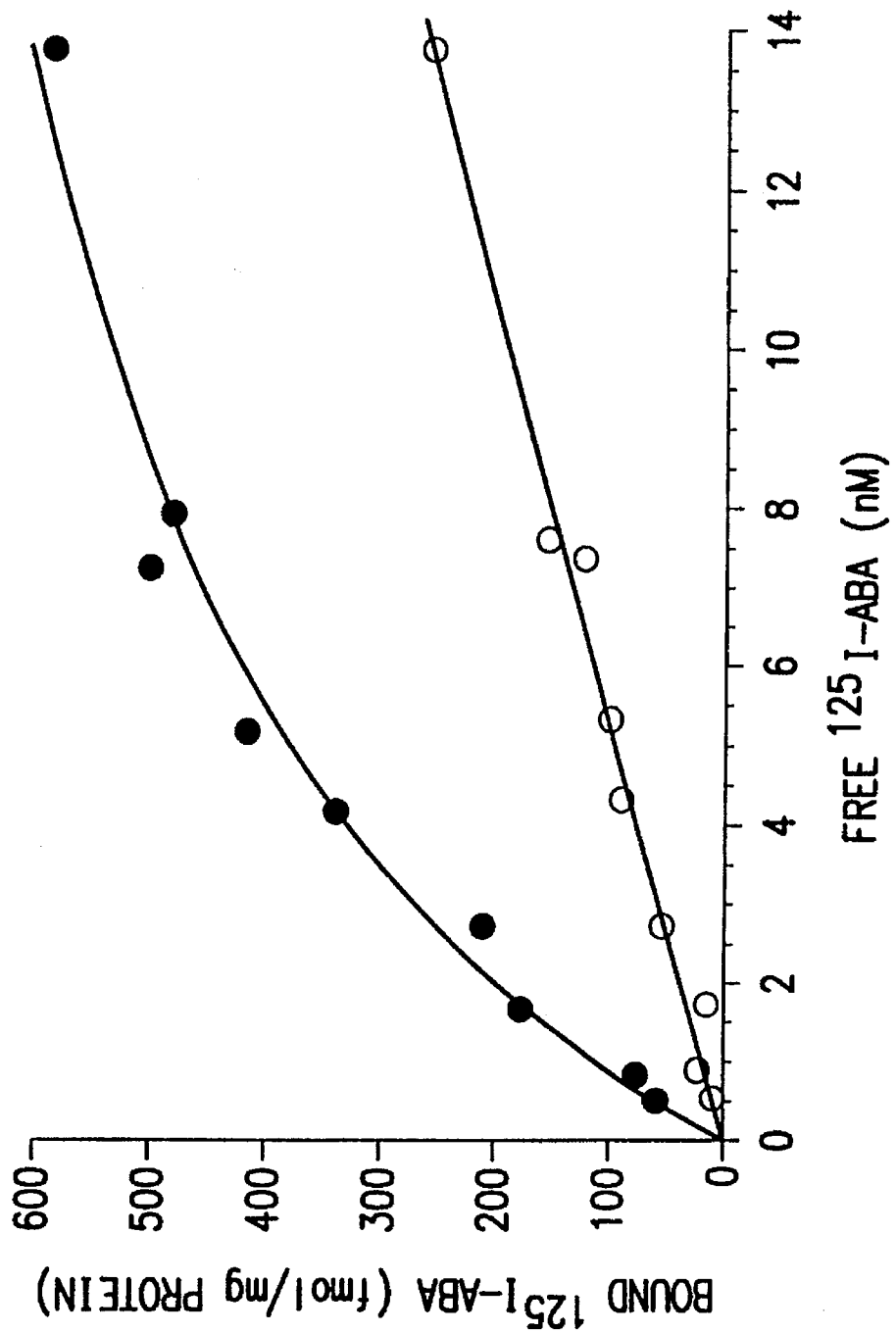
FIG. 11, A and B (A) Equilibrium binding of $^{125}$I-ABA to membranes prepared from A3 stable transfected CHO cells shows specific (●) and nonspecific (○) binding. Nonspecific binding was measured in the presence of 1 mM I-ABA. (B) Scatchard transformation of the specific binding.

The binding properties of the receptor encoded by HS-21a were evaluated on membranes prepared from CHO cells stably expressing the HS-21a cDNA. The radioligand, $^{125}$I-ApNEA, was previously used to characterize rat A3 adenosine receptors. In preliminary experiments, high non-specific $^{125}$I-APNEA binding to CHO cell membranes was observed which interfered with the measurement of specific binding to expressed receptors. Specific and saturable binding of the adenosine receptor agonist, $^{125}$I-ABA was measured on membranes prepared from the stably transfected cells (FIG. 11A). The specific binding of $^{125}$I-ABA could be prevented by either 1 mM nonradioactive I-ABA or 400 μM NECA. No specific binding of $^{125}$I-ABA was measured on membranes prepared from non-transfected CHO cells. The specific binding of $^{125}$I-ABA measured in either the presence of 10 μM GTPγS or 100 mM Gpp(NH)p was reduced by 56 and 44% respectively, relative to the specific binding measured in the absence of the uncoupling reagents. These results suggest that $^{125}$I-ABA exhibits some agonist activity on the receptor encoded by the HS-21a cDNA expressed in the stable CHO cell line. $^{125}$I-ABA binds to membranes prepared from the HS-21a stable CHO cells with a dissociation constant of 10 nM ($B_{max}$=258 fmol/mg protein) with a Hill coefficient of 0.99 indicating binding to a single class of high affinity sites (FIG. 11B).

Figure 12A:
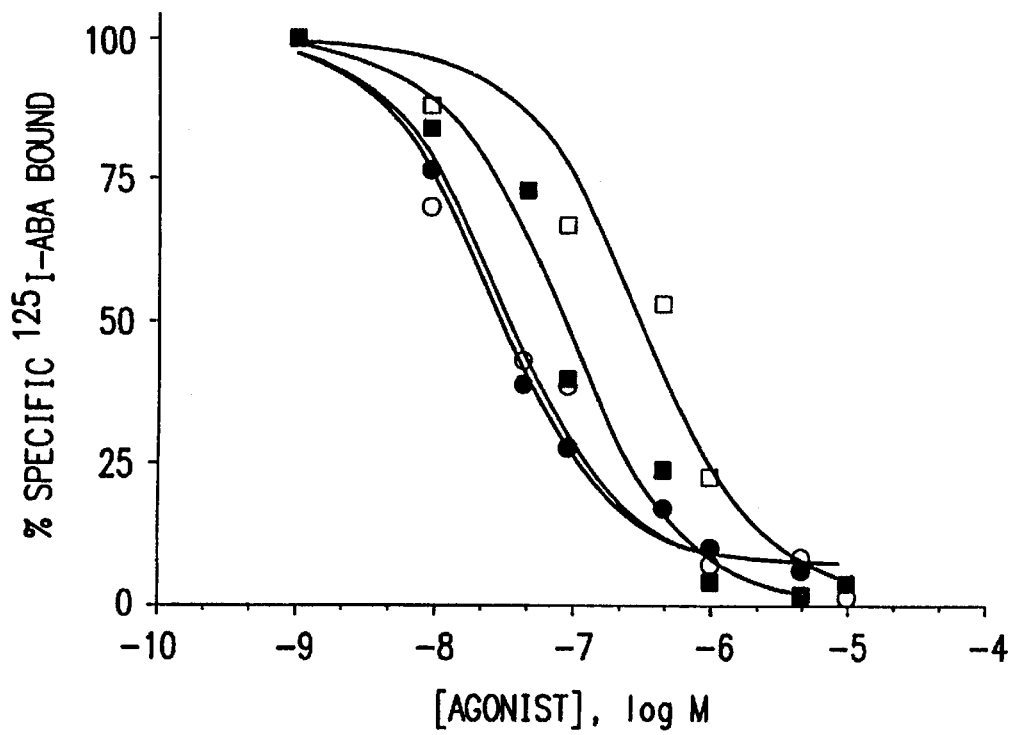
FIG. 12 Competition by agonists and antagonists for $^{125}$I-ABA binding to membranes prepared from stably transfected CHO cells expressing the human A3 adenosine receptor. Agonists (top panel), (●) NECA, (○) R-PIA, (●) CPA, ( ) S-PIA; antagonists (bottom panel), (●) I-ABOPX, (●) BW-A1433, (○) XAC, ( ) DPCPX.
Figure 12B:
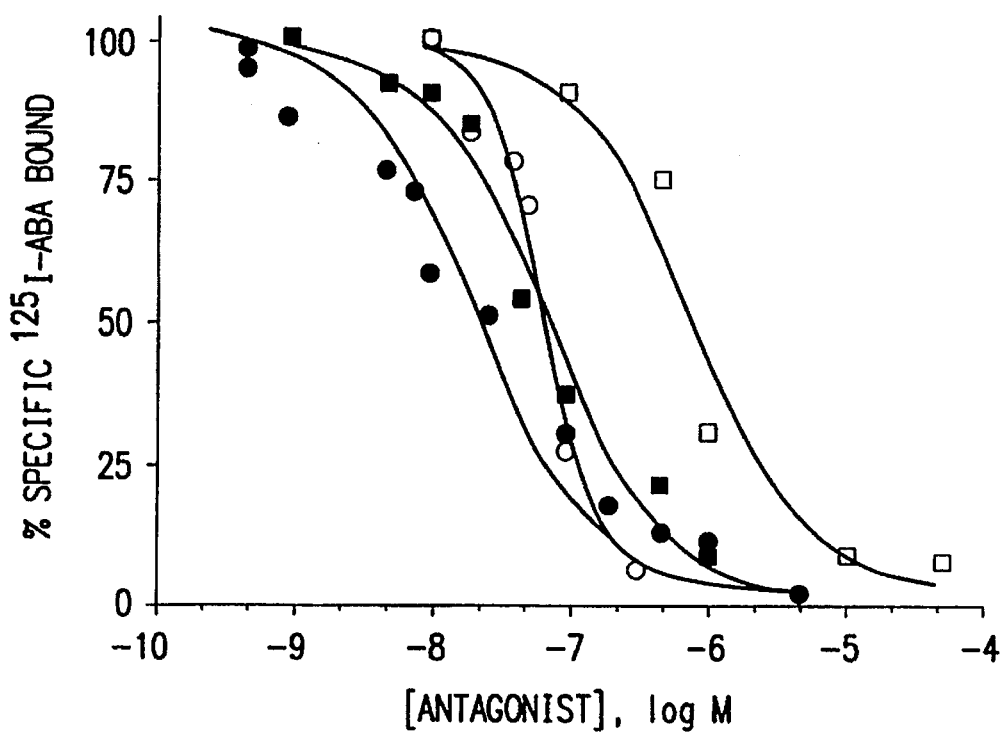
Figure 13A:
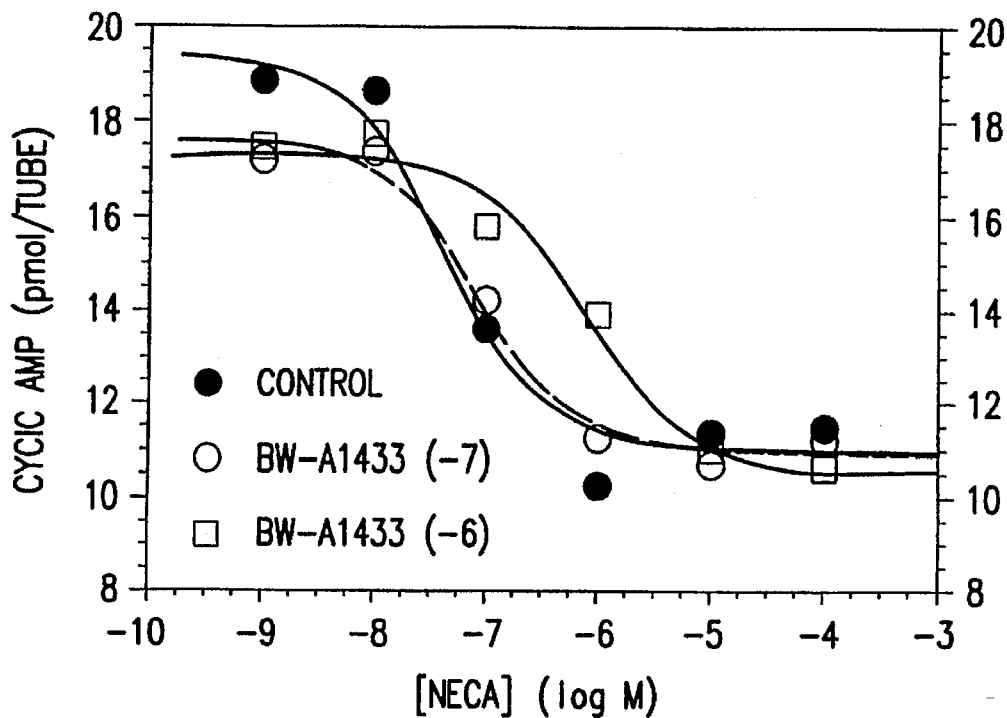
FIG. 13, A and B Competition by antagonists of NECA-inhibited cyclic AMP accumulation in CHO cells stably expressing the human A3 adenosine receptor. Dose response curves to NECA measured in the absence or presence of two concentrations of BW-A1433, XAC and I-ABOPX. The ED50's were used to construct Schild plots. Each figure is representative of 2–3 experiments.
Figure 13B:
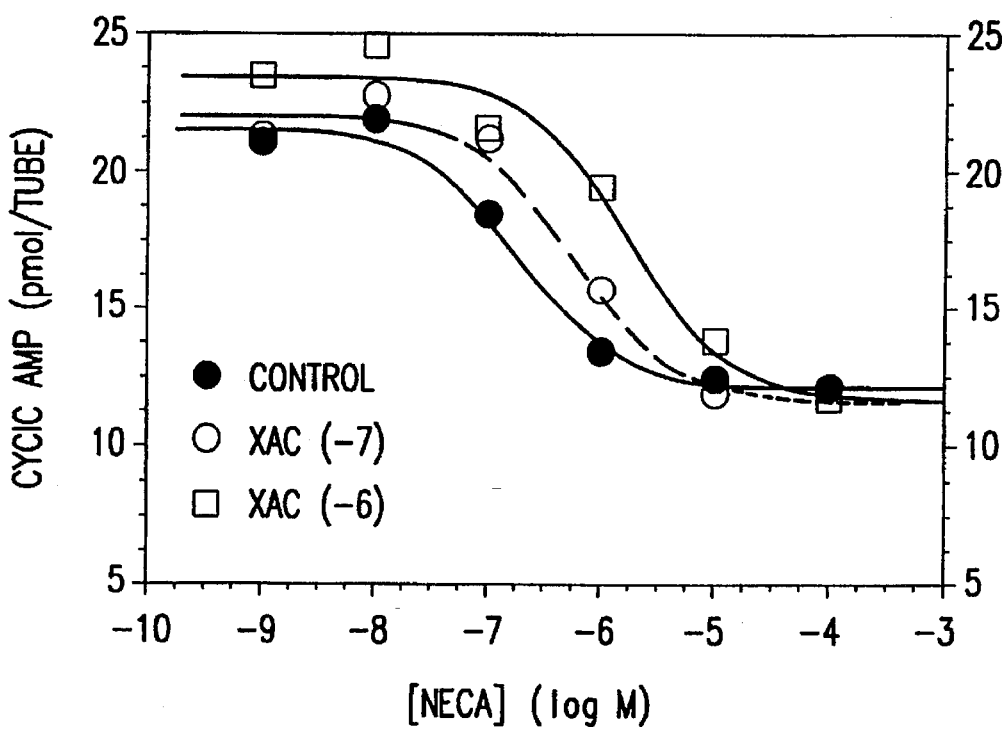
Figure 13C:
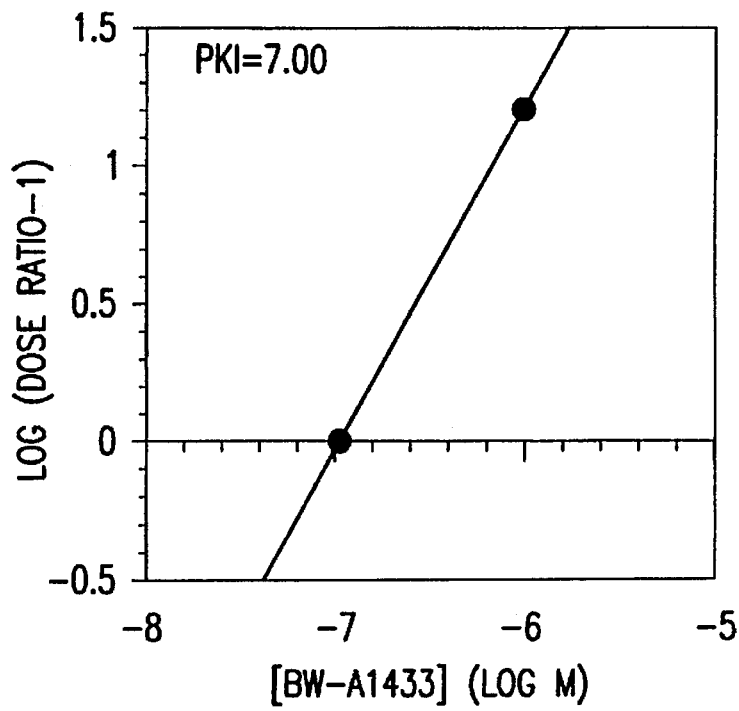
Figure 13D:
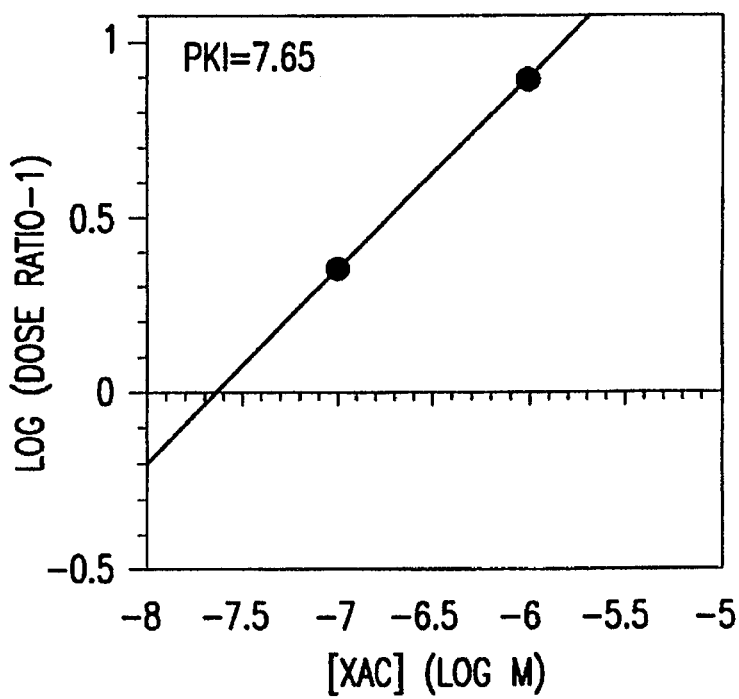
Figure 13E:
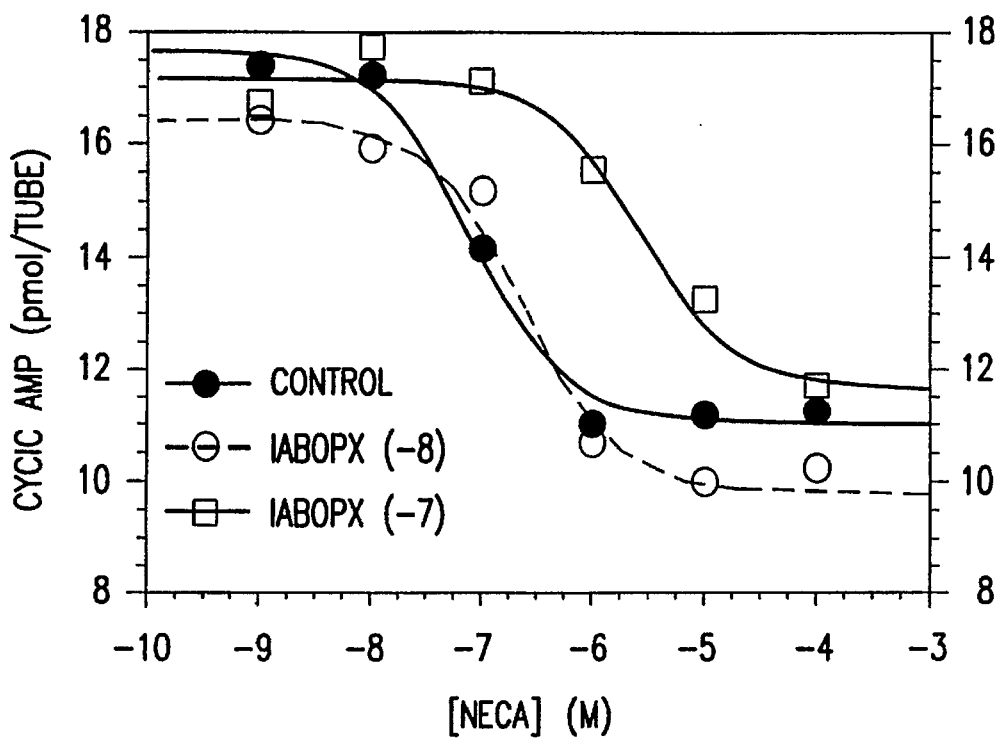
Figure 13F:
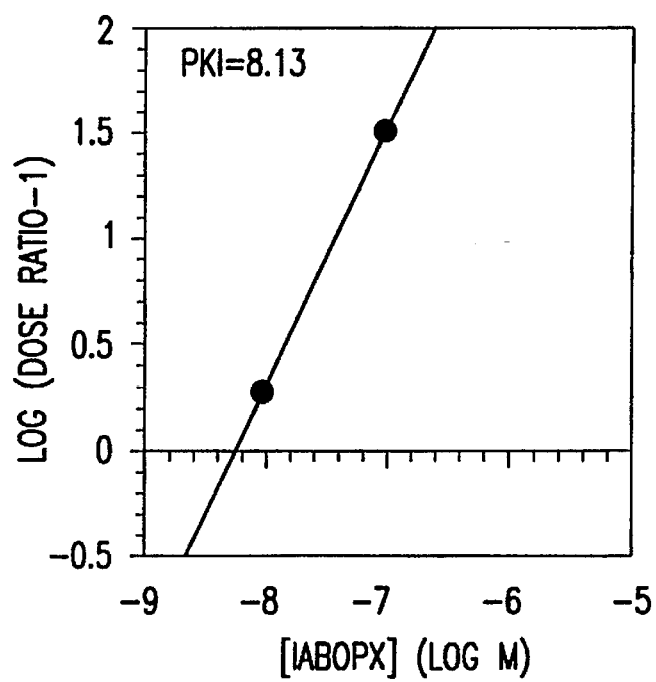

The competition of adenosine receptor agonists and antagonists for binding to HS-21a receptors was determined (FIG. 12). The $K_i$ values for agonists (top panel) were calculated to be 26 nM for NECA, 34 nM for R-PIA, 89 nM for CPA and 320 nM for S-PIA, resulting in a potency order profile of NECA>R-PIA>CPA>S-PIA. In contrast to the insensitivity of adenosine receptor antagonists reported for the rat A3 adenosine receptor subtype, a number of xanthine antagonists exhibited competition with $^{125}$I-ABA for binding to the HS-21a receptor (FIG. 12, lower panel). Studies of the sheep A3 adenosine receptor indicated that 8-phenylxanthines substituted in the para-position with acidic substituents are high affinity antagonists. By evaluating additional xanthines in this class we determined that I-ABOPX is the highest affinity antagonist yet reported for A3 adenosine receptors. The $K_i$ values for antagonists were calculated to be 18 nM for I-ABOPX, 55 nM for BW-A1433, 70 nM for XAC and 750 nM for DPCPX, resulting in a potency order profile of I-ABOPX>BW-A1433>XAC>DPCPX.

EXAMPLE 12 cAMP Studies

Determinations were made on stably transfected CHO cells in suspension as described (Linden et al., (1993) Mol. Pharm. 44:524–532). Supernatants (500 μL) were acetylated and acetylcyclic AMP was measured by automated radioimmunoassay (Hamilton, B. R. and Smith, D. O. (1991) J. Physiol. (Lond.) 432, 327–341). Antagonist dissociation constants were estimated from $pA_2$ values as described by Schild (1957) Pharm. Rev. 9, 242–246).

The ability of the HS-21a receptor stably expressed in CHO cells to couple to the cAMP regulatory system was measured using adenosine as an agonist. Adenosine (10 μM) produced a 30% inhibition of the forskolin-stimulated increase in cAMP. In the absence of forskolin, adenosine had no effect on the cAMP levels. In non-transfected CHO cells, adenosine had no effect on cAMP levels when measured with or without forskolin treatment.

I-ABA produced only about half as much inhibition of forskolin-stimulated cyclic AMP accumulation in CHO cells as did NECA and other agonists (PIA and CPA). Furthermore, in the presence of I-ABA, the dose response curve of NECA to lower cyclic AMP was right-shifted. These data indicate that I-ABA is a partial agonist in this system. Dose-response curves of NECA-induced inhibition of forskolin-stimulated cAMP accumulation were also right shifted in the presence of competing xanthine antagonists (FIG. 13). Schild analyses were used to estimate the $K_i$ from $pA_2$ values. The $K_i$ values determined by competitive binding for various agonists and antagonists are compared with the $K_A$ values in the functional cAMP assay in Table 1. The potency order profiles were nearly identical for the binding and functional assays, however, the $K_a$ of agonists to lower cAMP were consistently higher (i.e. lower potency) than $K_i$ values determined from competitive binding assays. Although the conditions of these assays differ, these data suggest that recombinant A3 receptors are not well coupled to inhibition of cyclic AMP accumulation in CHO cells.

EXAMPLE 13

Northern Blot Analysis

Human poly(A)$^+$ RNA from different tissue sources (Clontech) was fractionated on a 1% agarose-formaldehyde gel (Sambrook, J., Fritsch, E. and Maniatis, T. (1989) *Molecular Cloning: A Laboratory Manual*, Second Edition, (Cold Spring Harbor Press, Cold Spring Harbor, N.Y.), transferred to Hybond-N membranes and hybridized in 5×SSPE, 5×Denhardt's, 0.5% SDS, 50 mg/mL sonicated salmon testis DNA, with 30% formamide (for A1, A2a, and A2b) or 50% formamide (for HS-21a) at 42° C. DNA probes corresponding to nucleotides 512–1614, 936–2168, and 321–1540 of accession numbers X68485(A1), X68486 (A2a), and X68487(A2b) respectively, and a 1.7 kb SalI-BamHI fragment of HS-21a were labeled with $\alpha^{32}$P-dCTP by the random priming method. Filters were washed under high stringency conditions in 0.1×SSC at 65° C.

Figure 14A:
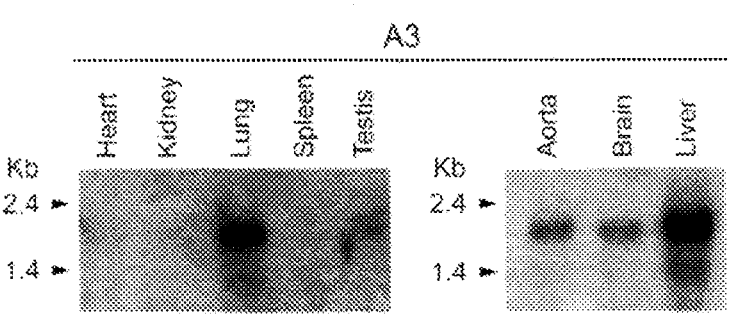
FIG. 14, A and B Northern blot analysis of the four human adenosine receptor subtypes. (A) 5 mg poly(A)$^+$ RNA from various human tissues probed with HS-21a. The two blots shown were transferred, hybridized and exposed separately. (B) 7.5 mg poly(A)$^+$ RNA from various human tissues probed with either A1, A2a, or A2b. Each blot was transferred and exposed separately.
Figure 14B:
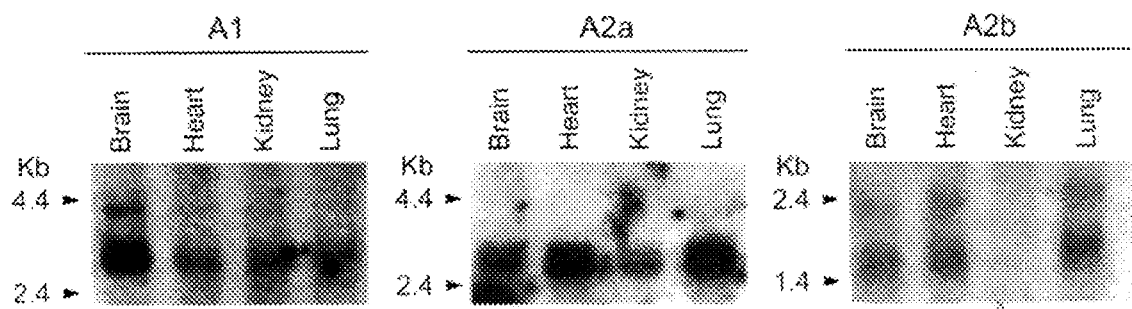

Poly A$^+$ RNA from a number of human tissues was evaluated by Northern blot analyses to establish the distribution of tissue expression for the HS-21a transcript (FIG. 14A). A 2 kb transcript was most abundantly expressed in lung and liver, with moderate amounts observed in brain and aorta. Low levels of expression were also observed in testis and heart. No expression was detected in spleen or kidney. The profile of lung=liver>>brain=aorta>testis>heart determined for HS-21a is considerably different from the tissue distribution of the other human adenosine receptor subtypes (FIG. 14B). A human A1 transcript (2.9 kb) is expressed in brain, heart, kidney and lung with the most abundant expression observed in the brain. A second hybridizing band of 4.3 kb is also observed in lower amounts in the brain. In contrast to the results obtained for the A1 adenosine receptor, the A2a adenosine receptor transcript (2.8 kb) is equally expressed in brain, heart and kidney with slightly higher levels of expression detected in the lung. (Two hybridizing bands were observed when the full length A2a coding sequence was used as a probe and may be the result of cross-hybridization with the A1 transcript (upper band)). In human brain, the expression of the A1 adenosine receptor subtype is most abundant in the cortex [Dodd, P. R., Watson, W. E. J., and Johnston, G. A. R. (1986) Clin. Exp. Pharmacol. Physiol. 13, 711–722] and the expression of the A2a adenosine receptor subtype mRNA has been shown by in situ hybridization to be restricted to the caudate, putamen and nucleus accumbens [Schiffmann, S. N., Libert, F., Vassart, G. and Vanderhaeghen, J. J. (1991) Neurosci. Lett. 130, 177–181]. The human brain mRNA utilized in the Northern analysis was prepared from the brain stem, pons, cerebellum, telencephalon, diencephalon and mesencephalon regions of the brain and does not represent enriched transcripts from those regions of the brain in which the most abundant expression of A1 and A2a adenosine receptors has been indicated by radioligand binding or in situ hybridization studies. For the human A2b subtype, two hybridizing transcripts of 1.7 kb and 2.1 kb were observed in brain, heart and lung. The smaller 1.7 kb transcript was more abundant. In contrast to the expression of the A1 and A2a adenosine receptor transcripts, no expression of A2b transcript was observed in the kidney. From the comparison of the distribution of human adenosine receptor transcripts, it can be concluded that the subtype transcripts are widely distributed but differ from each other in the abundance found in particular tissues.

EXAMPLE 14

UP-REGULATION OF A3 ADENOSINE RECEPTOR EXPRESSION ON CYTOKINE TREATED EOSINOPHILS AND HYPERSENSITIVITY THEREOF TO ADENOSINE

In asthmatics, mean adenosine concentrations measured in BAL fluid are significantly elevated relative to normal patients (Driver, et al. (1993) Am. Rev. Respir. Dis. 148:91–97). High concentrations of adenosine in airway fluids are therefore available for binding to and activation of A3 receptors that we have discovered are present on eosinophils. Accumulation of activated eosinophils in bronchial mucosa in response to an allergic challenge and activation of the A3 receptors results in eosinophil degranulation and exacerbation of the inflammatory and allergic responses. This example demonstrates the up-regulation of the A3 adenosine receptor on cytokine treated eosinophils and hence the hypersensitivity of activated eosinophils to adenosine agonists.

STEP A

Eosinophils and neutrophils (80–99% purity) were purified from human peripheral blood by an immunomagnetic procedure described by Hansel et al. (1991) J. Immunol. Methods 145: 105–110. Isolated cells (2–2.6×10$^6$ cells/mL) were cultured in the presence of 150 pM human recombinant granulocyte-macrophage colony stimulating factor, GM-CSF (Calbiochem, San Diego, Calif.) for 16 hours in RPMI with 10% fetal calf serum, at 37° C. in 5% $CO_2$. Total RNA was extracted by the guanidinium isothiocyanate method (Chirgwin, J. M., et al, (1979) Biochemistry 18:5294–5299) from approximately 1.3×10$^7$ human eosinophils (+) or (−) GM-CSF stimulation. First strand cDNA was reverse transcribed from 600 ng total RNA in a volume of 20 µl containing 20 mM Tris-HCL (pH 8.4), 50 mM KCl, 2.5 mM $MgCl_2$, 0.1 mg/ml bovine serum albumin (BSA), 0.5 mM dNTP's, 10 mM DTT, 10 units SUPERSCRIPT II reverse transcriptase (LIFE TECHNOLOGIES, INC., Gathersburg, Md.), and 50 ng random hexamers.

STEP B

Human adenosine receptor subtype transcript expression was determined using the polymerase chain reaction (PCR). Three µl of the randomly primed first strand cDNA, (+) or (−) GM-CSF stimulation, was used as template in a PCR amplification reaction according to the GENEAMP protocol (PERKEN ELMER CETUS, Norwalk, Conn.) containing 50 pmol subtype selective primers in a total volume of 100 µl. Primer pairs for amplification (see Table 1) were 266+267 (A1), 253+254 (A2a), 261+262 (A2b), 230+236 (A3), and 141+142 for glyceraldehyde-3-phosphate dehydrogenase (GAPDH). Primer pairs for amplification of adenosine receptor subtypes were designed to span four (A1 primers) and five (A2a, A2b and A3 primers) transmembrane domains and gave no or incorrect sized PCR products when used to amplify human genomic DNA. Primers 141+142 are based on the published human GAPDH sequence (Tokunaga, K., et al, (1987) Cancer Research 47:5616–5619). Cycling parameters were 1 min at 94° C., 1 min at 55° C., 3 min at 72° C. for 35 cycles (A1), 25 cycles (A2a), 35 cycles (A3), and 20 cycles (GAPDH). Cycling parameters for A2b were 1 min at 94° C., 1 min at 59° C., 3 min at 72° C. for 30 cycles.

STEP C

Ten µl of each PCR amplification reaction was elecrophoresed on a 1.4% agarose gel and alkaline blotted to Zeta-Probe GT membranes according to the manufacturer's protocol (BIO-RAD, Hercules, Calif.). Membranes were hybridized in 0.25M sodium phosphate (pH 7.2), 0.5M NaCl, 7.0% sodium dodecyl sulphate (SDS), 1 mM EDTA, 1% BSA, and 1×10$^6$ cpm/ml $^{32}$P labeled probe at 50° C. Double-stranded DNA probes were generated by Klenow enzyme extension of annealed oligonucleotide pairs including $\alpha^{32}$P-dCTP. Oligonucleotide pairs for probe synthesis (see Table 1) were 268+269 (A1), 66+67 (A2a), 263+264 (A2b), 259+260 (A3), and 143+144 (GAPDH). Oligonucleotides 259+260 are based on the published sheep A3 adenosine receptor (Linden, J., et al, (1993) Mol. Pharmacol. 44:524–532) and 143+144 on the human GAPDH sequence (Tokunaga et al). Following hybridization membranes were washed to a final stringency of 75 mM NaCl, 7.5 mM sodium citrate, 0.1% SDS and exposed to autoradiography film. The presence of A2a, A2b and A3 receptor PCR products were detected from normal and GM-CSF treated eosinophils. In contrast, no A1 products were observed in either normal or GM-CSF treated eosinophils.

STEP D

PCR reaction products were quantitated using a Molecular Dynamics Phosphorimager and ImageQuant software. Phosphor storage screens were exposed to hybridized membranes for 3 hrs (A2a,A2b,A3) or 15 hrs for GAPDH. A1 was not exposed because no signal was present after autoradiography. Quantitation of GAPDH was used to correct message level differences in the (+) or (−) GM-CSF stimulated human eosinophils. Analysis of quantitation data on the effect of GM-CSF stimulation of human eosinophils showed no change in A2a message levels, an approximate 3-fold increase in A2b message levels, and an approximate 10-fold increase in A3 message levels. These observations are the result of an experiment, in which genomic contamination was detected in the total RNA isolated from both normal and GM-CSF stimulated eosinophils. Specific adenosine receptor amplification primers were designed to be unaffected by potential genomic DNA contamination, however, GAPDH PCR products detected result from amplification of cDNA transcribed from total RNA and genomic DNA. The amount of GAPDH amplified is used to normalize message levels between the normal and GM-CSF stimulated eosinophils. Threrefore, it is possible that the increased amount of A3 and A2b transcript expression measured after GM-CSF stimulation is underestimated.

The observed up-regulation of the A3 adenosine receptor expression as a result of eosinophil exposure to cytokines demonstrates the hypersensitivity to adenosine agonists. Treatment of cytokine activated eosinophils with A3 adenosine antagonists, such as I-AOBPX, results in blockade of this hypersensitivity and inhibition of eosinophil degranulation and effector function.

EXAMPLE 15

IDENTIFICATION OF THE A3 ADENOSINE RECEPTOR ON EOSINOPHILS

Antisense and sense oligonucleotide probes were derived from the sheep A3 sequence (Linden et al. (1993) Mol. Pharmacol. 44: 524–532) for in situ hybridization of sheep lung sections. Oligonucletide sequences used were 281 antisense, 280 sense, 283 antisense, 282 sense. Antisense and sense oligonucleotide probes were derived from the human A3 sequence (243 antisense, 242 sense, 252 antisense, 251 sense) for in situ hybridization on human lung sections. Oligonucleotides were labeled with $^{35}$S-dATP by terminal deoxynucleotidyl transferase (Boehringer Mannheim) according to the manufacturer's protocol.

Cryostat sections (12 µm) of lung tissue were mounted onto poly-L-lysine coated slides, fixed for 10 minutes in 4% paraformaldehyde/phosphate buffered saline, rinsed twice for 5 minutes in phosphate buffered saline and dehydrated through an ethanol gradient. Prior to hybridization, prepared slides were incubated with 1 µg/mL proteinase K in phosphate buffered saline for 5 minutes at 37° C. Slides were re-fixed in 4% paraformaldehyde and equilibrated in 0.1M triethanolamine for five minutes, acetylated in 0.1M triethanolamine with 0.25% acetic anhydride for 10 minutes, washed twice in 2× SSC, dehydrated through an ethanol gradient and air dried. Prehybridization was carried out in a moist chamber at 45° C. for 1–2 hours in hybridization buffer (50% formamide, 4× SSC, 1× Denhardt's solution, 0.5% SDS, 20 mM dithiothreitol, 500 µg/mL yeast tRNA, 100 µg/mL poly A, 10% dextran sulphate). Tissue sections were hybridized overnight at 45° C. in hybridization buffer containing $2\times10^6$ cpm $^{35}$S-labeled oligonucleotide/50 µL per slide. After incubation, sections were washed twice in 4× SSC at room temperature for 15 minutes and twice in 1× SSC at room temperature for 15 minutes. Low stringency washes utilized two washes with 1× SSC at 37° C. for 15 minutes and two washes with 1× SSC at 55° C. for 15 minutes. High stringency washes utilized two washes with 0.1× SSC at 37° C. for 15 minutes and two washes with 0.1× SSC at 55° C. for 15 minutes. β-mercaptoethanol, 0.1% and 0.1% Nathiosulfate was included in all wash buffers. At the completion of the washes, slides were dehydrated through an ethanol gradient containing 0.3M NH$_4$OAc. Slides were dipped in LM-1 photoemulsion (Amersham) and exposed for 2–5 weeks. After development, slides were counterstained with hematoxylin and eosin (H&E) for cell visualization.

Figure 15A:
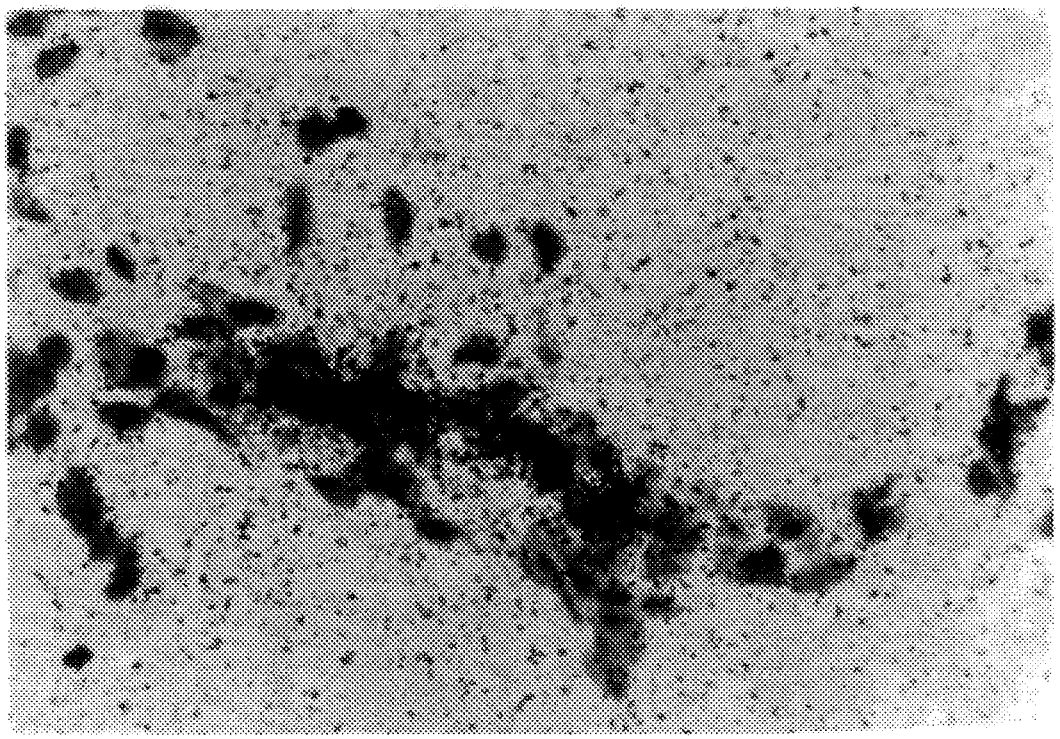
FIG. 15, A and B Hybridization of antisense (A) and sense (B) A3 subtype oligonucleotide probes on sheep lung. 40× magnification of slides showing hybridization of peripheral eosinophils. Length of exposure was 23 days.
Figure 15B:
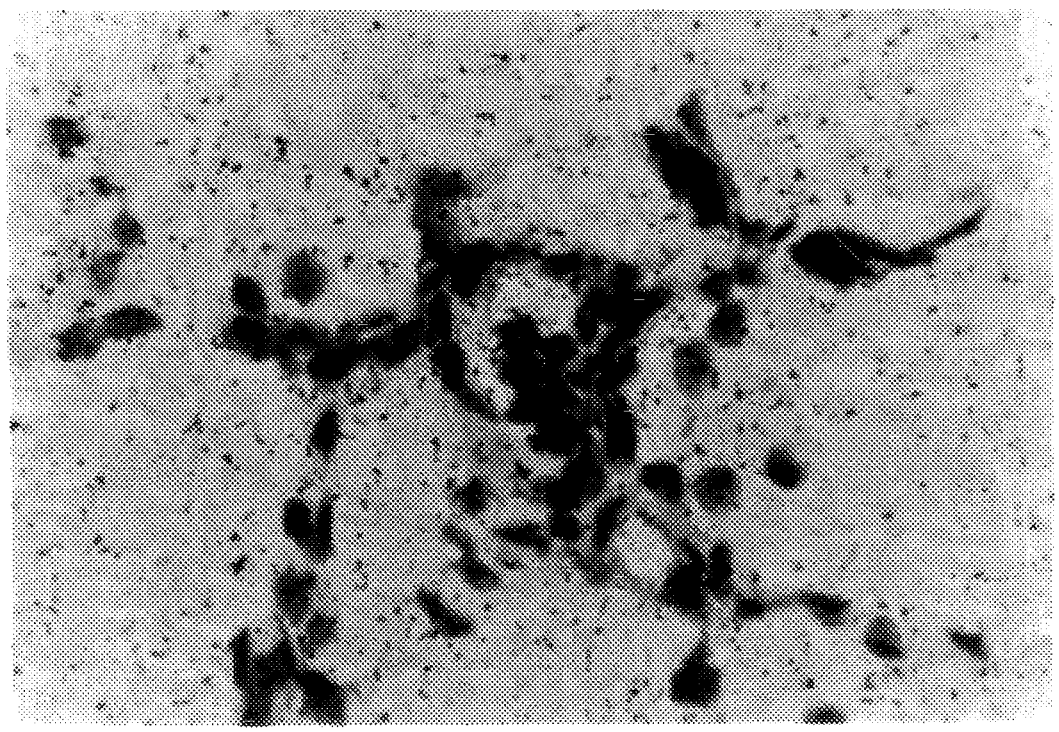
Figure 16A:
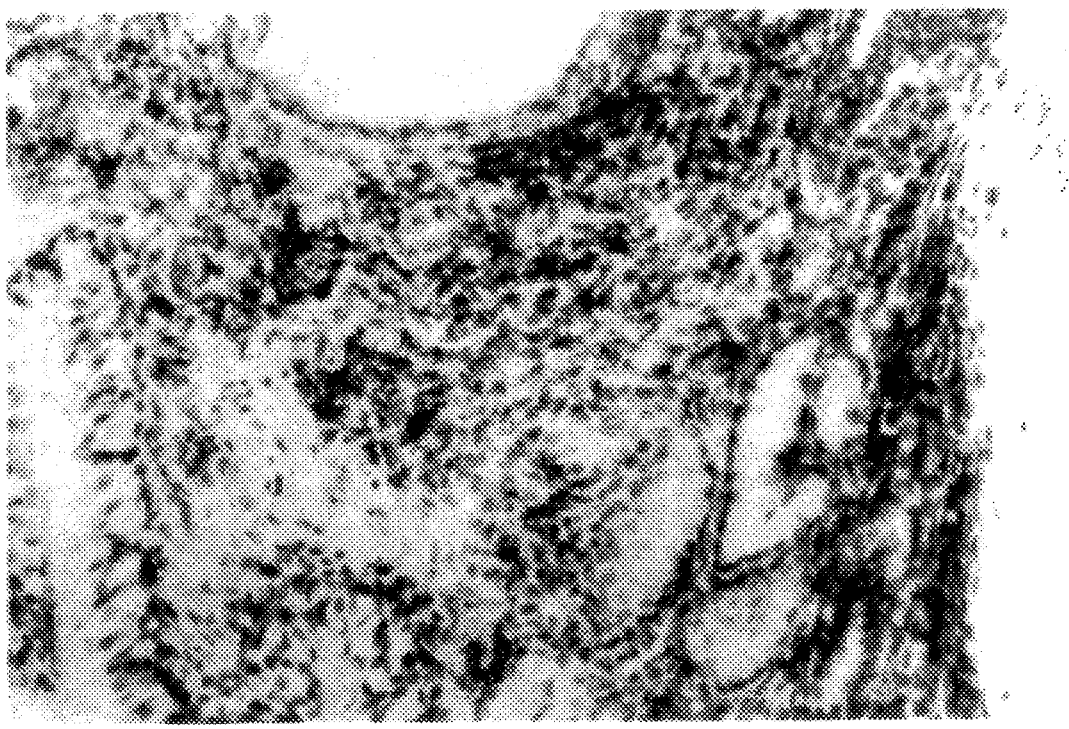
FIG. 16, A and B Hybridization of antisense (A) and sense (B) A3 subtype oligonucleotide probes on sheep lung. 16× magnification of slides showing hybridization of eosinophils within the submucosa. Length of exposure was 21 days.
Figure 16B:
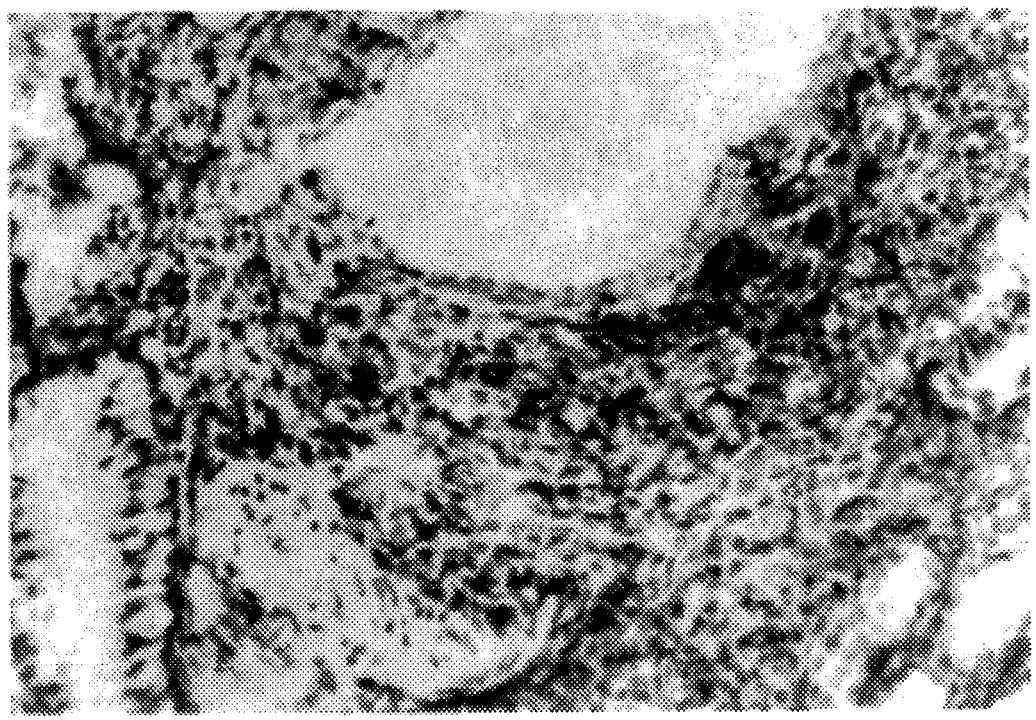
Figure 17A:
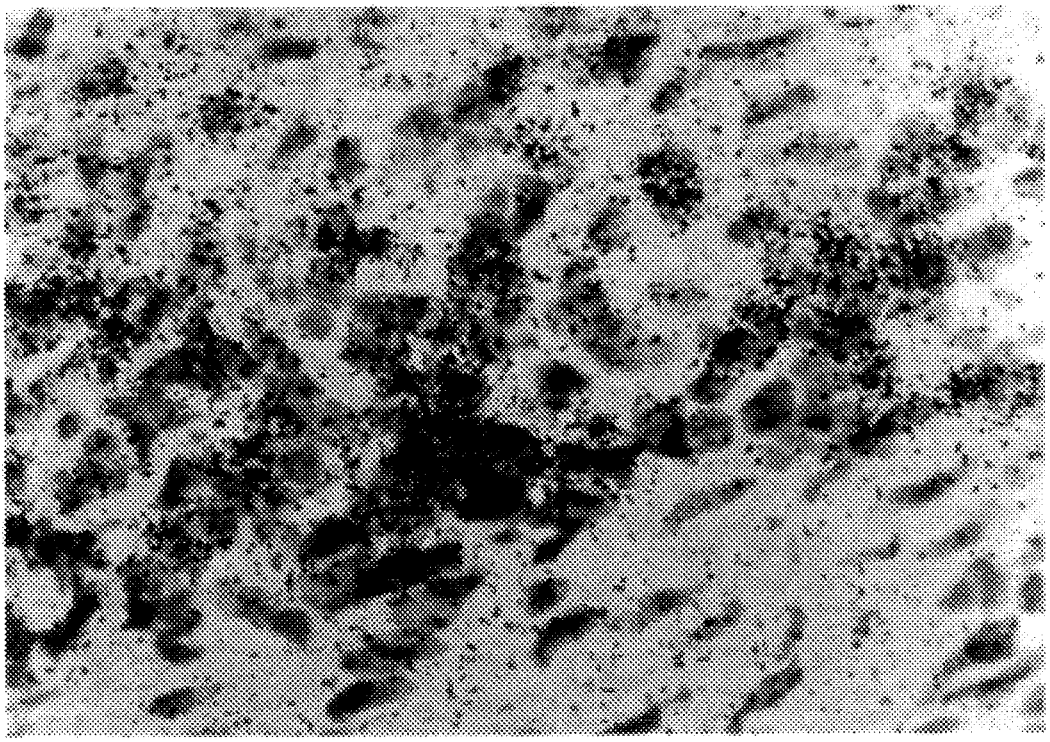
FIG. 17, A and B Hybridization of antisense (A) and sense (B) A3 subtype oligonucleotide probes on sheep lung. 40× magnification of slides showing hybridization of eosinophils within the submucosa. Length of exposure was 21 days.
Figure 17B:
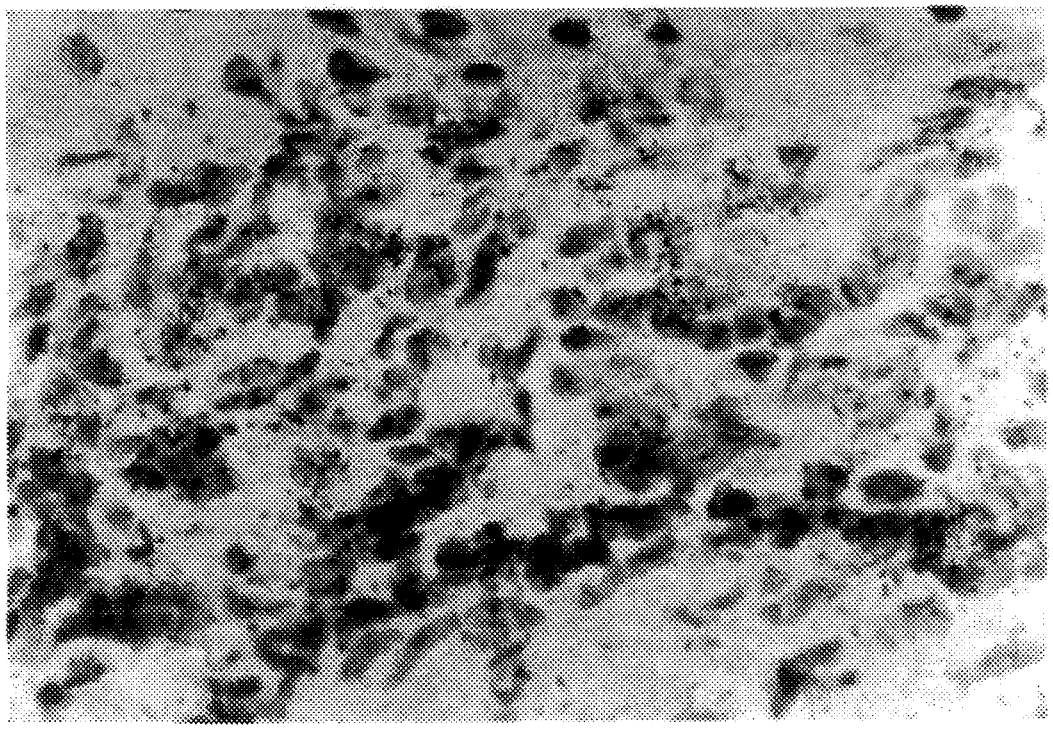
Figure 18A:
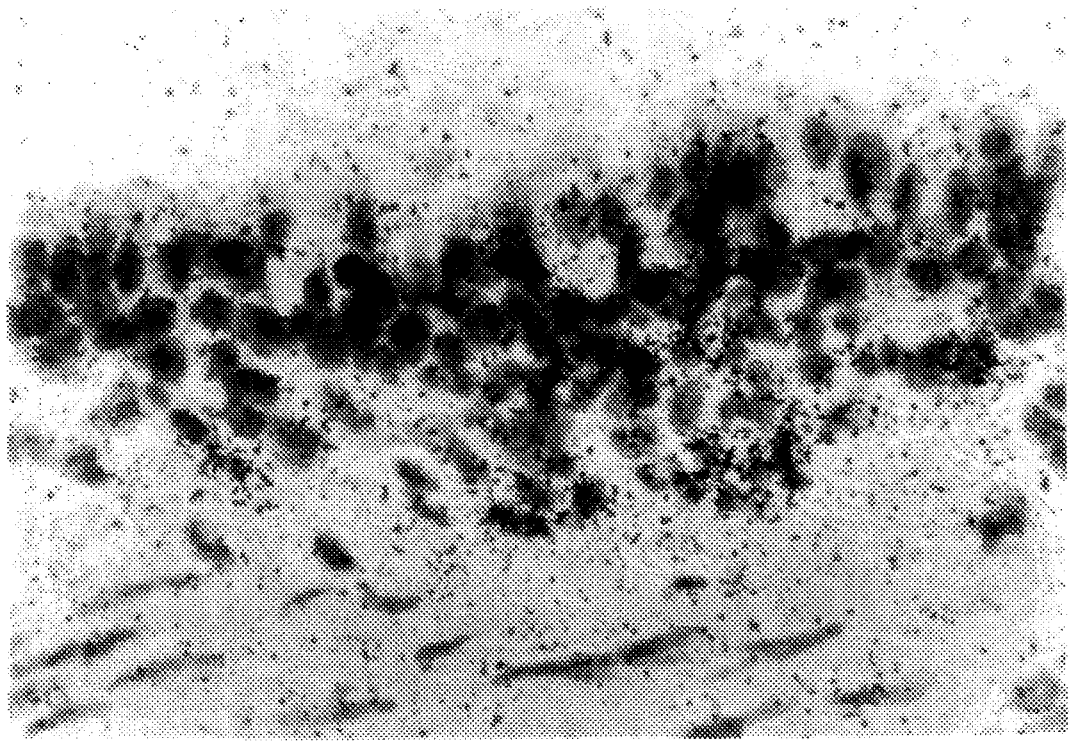
FIG. 18, A and B Hybridization of antisense (A) and sense (B) A3 subtype oligonucleotide probes on sheep lung. 40× magnification of slides showing hybridization of eosinophils within the epithelium. Length of exposure was 21 days.
Figure 18B:
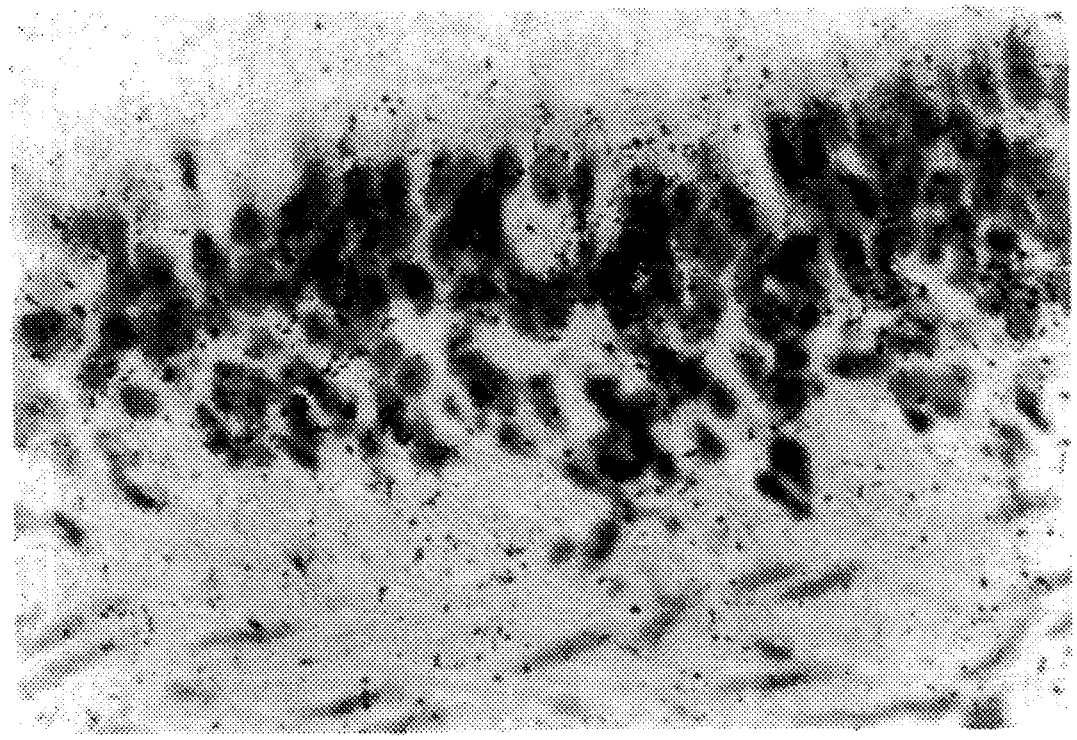
Figure 19A:
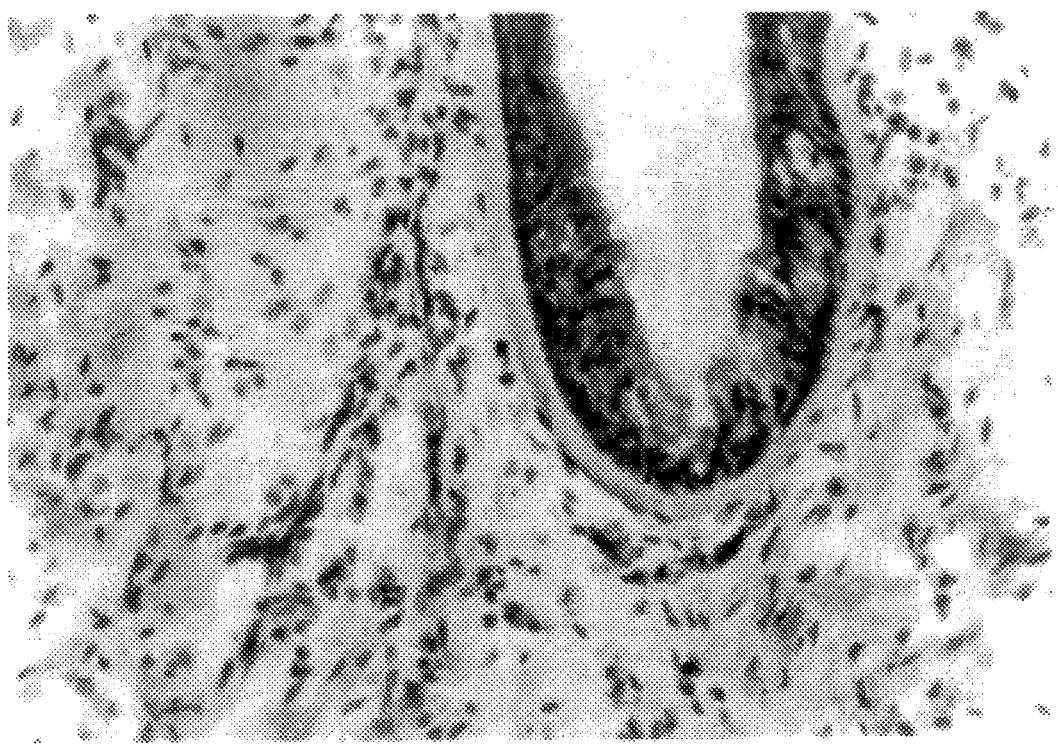
FIG. 19, A and B Hybridization of antisense (A) and sense (B) A3 subtype oligonucleotide probes on human cartilaginous bronchus. 16× magnification of slides showing hybridization of eosinophils within the submucosa.
Figure 19B:
Figure 20:
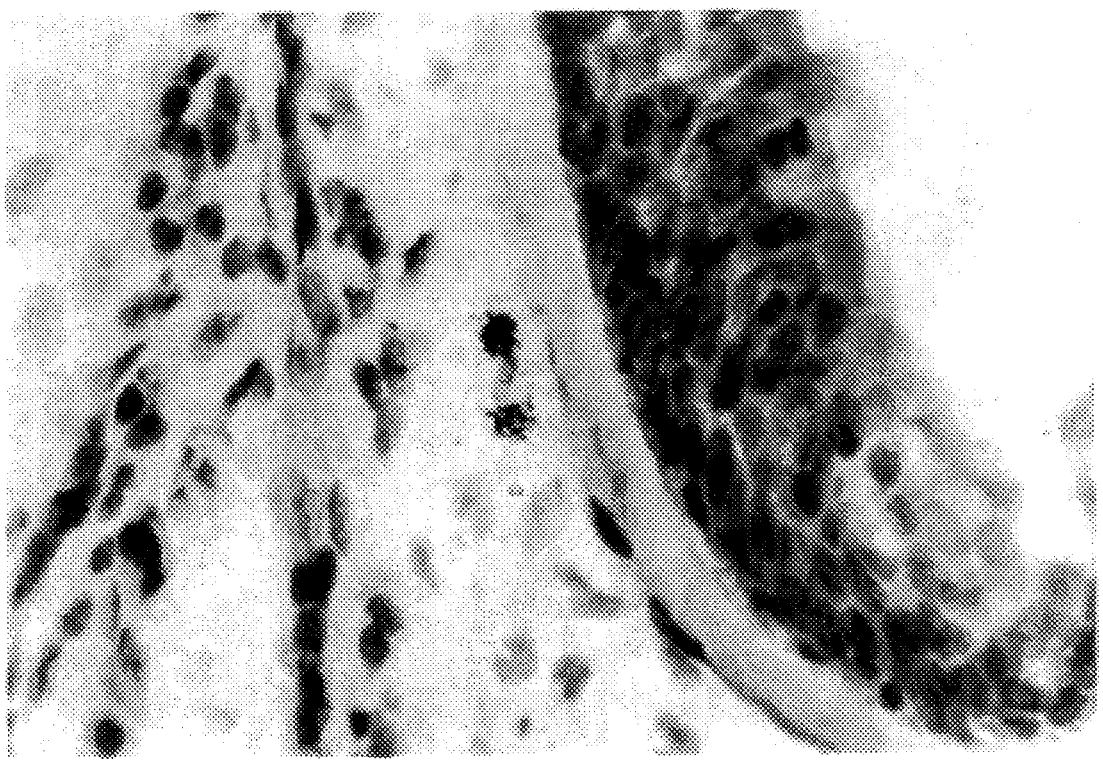
Figure 21A:
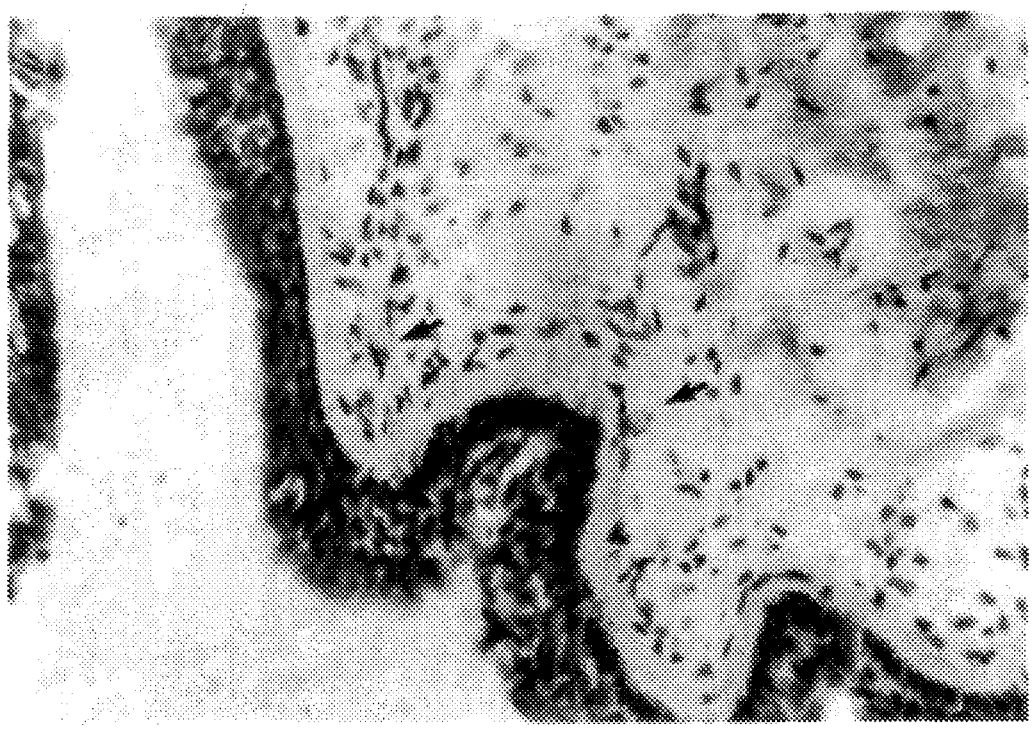
FIG. 21, A and B Hybridization of antisense A3 subtype oligonucleotide probe on human lung section. 16× (A) and 40× (B) magnification of eosinophil within the submucosa.
Figure 21B:
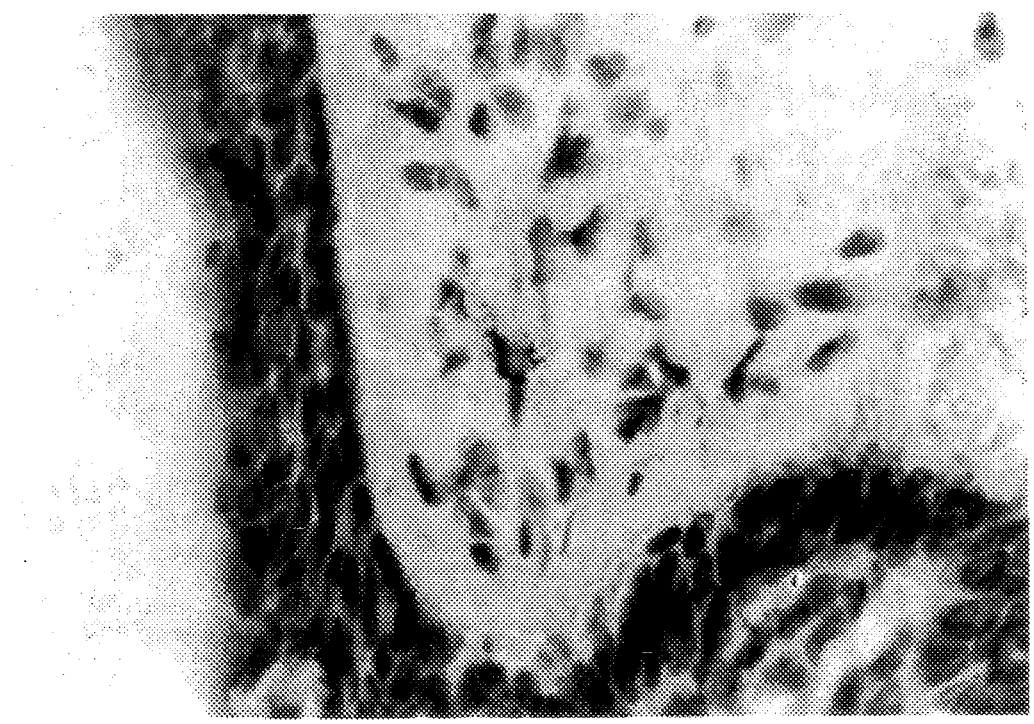

Antisense hybridization was localized specifically on eosinophils in the periphery (FIG. 15), submucosa (FIGS. 16 and 17) and epithelium (FIG. 18) within sheep lung. (Four pairs of photographs showing antisense (a) and sense (b) oligo hybridizations on H&E stained sections). Positive identification of eosinophils was confirmed with the use of Hansel's stain. Sense probes showed no specific hybridization. In human cartilaginous bronchus (FIGS. 19, 20, 21), hybridization of antisense oligonucleotide probes were localized on eosinophils in the submucosa. In both sheep and human lung sections, no hybridization was observed in the endothelium, smooth muscle or glands.

TABLE 1

| NAME | SEQUENCE |
|---|---|
| 66 | 5'GCCTCTTTGAGGATGTGGTCCCCATGAACTACATGGTGTACTTCA, SEQ ID:29: |
| 67 | 5'GCAGGGGCACCAGCACACAGGCAAAGAAGTTGAAGTACACCATGT, SEQ.ID:30: |
| 141 | 5'TCACCATCTTCCAGGAGC, SEQ.ID:31: |
| 142 | 5'ACTCCTTGGAGGCCATGT, SEQ.ID:32: |
| 143 | 5'TCCTGCACCACCAACTGCTTAGCCCCCCTGGCCAAGGTCATCCAT, SEQ.ID. 33: |
| 144 | 5'CATGAGCCCTTCCACGATGCCAAAGTTGTCATGGATGACCTTGGC, SEQ.ID:34: |
| 230 | 5'GTTACCTACATCACCATG, SEQ.ID:35: |
| 236 | 5'GTTAGATAAGTTCAGACT, SEQ.ID:36: |
| 242 | 5'CTGACCTCAGAGTACCACAGAAATGTCACCTTCCTTTCATGCCAA, SEQ.ID:37: |
| 243 | 5'TTGGCATGAAAGGAAGGTGACATTTCTGTGGTACTCTGAGGTCAG, SEQ.ID:38: |
| 251 | 5'CTCAGTCTGAACTTATCTAACTCCAAAGAGACAGGTGCATTTTATG, SEQ.ID:39: |
| 252 | 5'CATAAAATGCACCTGTCTCTTTGGAGTTAGATAAGTTCAGACTGAG, SEQ.ID:40: |
| 253 | 5'TCCTCGGTGTACATCACG, SEQ.ID:41: |
| 254 | 5'TCCATCTGCTTCAGCTGT, SEQ.ID:42: |
| 259 | 5'CTGGGCCTTTGCTGGCTGGTGTCATTCCTGGTGGGATTGACCCCC, SEQ.ID:43: |
| 260 | 5'TGAGGTCAGTTTCATGTTCCAGCCAAACATGGGGGTCAATCCCAC, SEQ.ID:44: |
| 261 | 5'ATGCTGCTGGAGACACAGGA, SEQ.ID:45: |
| 262 | 5'TGGTCCATCAGCTCAGTGC, SEQ.ID:46: |
| 263 | 5'GGTGGAACAGTAAAGACAGTGCCACCAACAACTGCACAGAACCCTGGGATGGAACCACGA, SEQ.ID:47: |
| 264 | 5'GGACCACATTCTCAAAGAGACACTTCACAAGGCAGCAGCTTTCATTCGTGGTTCCATCCC, SEQ.ID:48: |
| 266 | 5'CTACATCGGCATCGAGGT, SEQ.ID:49: |
| 267 | 5'GAACTCGCACTTGATCAC, SEQ.ID:50: |
| 268 | 5'TGGTGGGACTGACCCCTATGTTTGGCTGGAACAATCTGAGTGCGG, SEQ.ID:51: |
| 269 | 5'TGCTGCCGTTGGCTGCCCAGGCCCGCTCCACCGCACTCAGATTGT, SEQ.ID:52: |
| 280 | 5'CTGAGCTCAGCAGACGAAAACCTCACCTTCCTACCCTGCCGA, SEQ.ID:53: |

TABLE 1-continued

| NAME | SEQUENCE |
|---|---|
| 281 | 5'TCGGCAGGGTAGGAAGGTGAGGTTTTCGTCTGCTGAGCTCAG, SEQ.ID:54: |
| 282 | 5'CTCAGCCAGAGCTTTTCTGGCTCCAGAGAGACAGGCGCATTCTATG, SEQ.ID:55: |
| 283 | 5'CATAGAATGCGCCTGTCTCTCTGGAGCCAGAAAAGCTCTGGCTGAG, SEQ.ID:56: |

EXAMPLE 16

SPECIFIC INHIBITION OF ADENOSINE INDUCED EOSINOPHIL ACTIVATION

We have discovered that adenosine, adenosine metabolites and other A3 adenosine receptor agonists induce eosinophil activation in animals and that this can be prevented by selective antagonists of the A3 receptor. The release of enzymes, bioactive amines and arachidonic acid metabolites following eosinophil activation causes vasoconstriction, edema, leukocyte accumulation, and ultimately, tissue damage. Eosinophil activation is a component of: myocardial reperfusion injury, hypersensitivity reactions (asthma, allergic rhinitis, and urticaria), ischemic bowel disease, autoimmune inflammationa, and atopic dermatitis and many other diseases. The invention consists of the use of any of a series of highly specific A3 adenosine receptor antagonists to treat or prevent these diseases and pathologic effects that result from eosinophil activation.

The effects of A3 adenosine receptor ligands on eosinophil degranulation are determined by the generation of superoxide anion from opsinized zymosan activated human eosinophils using the reduction of horse heart ferricytochrome c (Babior, et al. (1973) J. Clin. Invest. 52: 741–744). Specificically, isolated eosinophils ($1 \times 10^6$ cells/mL) are resuspended in Hank's balanced salt solution and preincubated with adenosine or the A3 adenosine agonist, $N^6$-(4-amino-3-iodoaminobenzyl)adenosine, I-ABA, in the absence or presence of adenosine receptor antagonists, such as 3-(3-iodo-4-aminobenzyl)-8-(4-oxyacetate)phenyl-1-propylxanthine, I-ABOPX, at 37° C. for 15 min in the presence of cytoclasin B (5 µg/mL) and 100 µM cytochrome c. Oposinized zymosan particles (2 mg/mL) are added and cells were incubated for 60–90 minutes. The reaction is terminated by centrifugation (400×g, 5 min) at 4° C. and supernatants were recovered. Supernatant absorbance is measured at 550 nm in a spectrophotometer. The amount of superoxide anion generated is determined from the amount of cytochrome c reduced. The amount of cytochrome c reduced is converted to nanomoles by using the molar extinction coefficient of $2.1 \times 10^4 M^{-1} cm^{-1}$.

The provision of A3 adenosine receptor selective antagonists significantly inhibits release of superoxide anion from eosinophils exposed to activating amounts of adenosine or adenosine agonist analogs according to this assay.

While the foregoing specification teaches the principles of the present invention, with examples provided for the purpose of illustration, it will be understood that the practice of the invention encompasses all of the usual variations, adaptations, modifications, as come within the scope of the following claims and its equivalents.

What is claimed is:

1. A method for treating or preventing allergic and inflammatory diseases which comprises contacting the eosinophil A3 adenosine receptor with an amount of an A3 adenosine receptor subtype specific antagonist effective to prevent eosinophil activation.

2. The method of claim 1 wherein said allergic and inflammatory diseases are selected from asthma, hypersensitivity, rhinitis, hay fever, serum sickness, allergic vasculitis, atopic dermatitis, dermatitis, psorasis, eczema, idiopathic pulmonary fibrosis, eosinophillic cholecystitis, chronic airway inflammation, hypereosinophilic syndromes, eosinophillic gastroenteritis, edema, urticaria, eosinophilic myocardial disease, episodic angioedema with eosinophilia, inflammatory bowel disease, ulcerative colitis, allergic granulomatosis, carcinomatosis, eosinophilic granuloma and familial histiocytosis.

3. The method of claim 2 wherein said antagonist is:

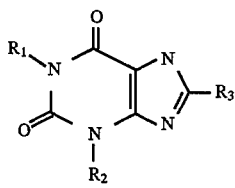

wherein $R_1$, $R_2$, and $R_3$, independently, are as defined below:

| $R_1$ | $R_2$ | R3 |
|---|---|---|
| lower alkyl | benzyl<br>halogenated benzyl<br>amino-benzyl<br>halogenated amino-benzyl. | benzyl-acid |

4. The method of claim 3 wherein said xanthine is:

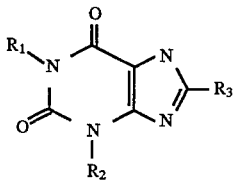

wherein $R_1$, $R_2$, and $R_3$, independently, are as defined below:

| $R_1$ | $R_2$ | R3 |
|---|---|---|
| —$C_3H_7$ | —$C_3H_7$ | —$CH_2$—$C_6H_4$—O-acid |
| —$CH_3$ | -benzyl | —$CH_2$—COO— |
| —$C_2H_5$ | -halogenated benzyl<br>-aminobenzyl<br>-halogenated aminobenzyl | -indole | wherein said acid is -indole, -carboxylate, sulphonate, phosphonate.

5. The method of claim 4 wherein the xanthine is selected from the group consisting of IABOPX, and BW-A1433.

6. A method for preventing or treating asthma, hypersensitivity, rhinitis, hay fever, serum sickness, allergic vasculitis, atopic dermatitis, dermatitis, psorasis, eczema, idiopathic pulmonary fibrosis, eosinophillic cholecystitis, chronic airway intimation, hypereosinophilic syndromes, eosinophillic gastroenteritis, edema, urticaria, eosinophilic myocardial disease, episodic angioedema with eosinophilia, inflammatory bowel disease, ulcerative colitis, allergic granulomatosis, carcinomatosis, eosinophilic granuloma and familial histiocytosis in a human which comprises administering an amount of a xanthine or a xanthine derivative having an affinity for the A3 subtype of the human adenosine receptor on eosinophils which is at least one order of magnitude greater than the affinity for either the A1, A2a or A2b subtypes of the human adenosine receptor effective to antagonize activation of the adenosine receptor of the A3 subtype.

* * * * *

UNITED STATES PATENT AND TRADEMARK OFFICE
CERTIFICATE OF CORRECTION

PATENT NO. : 5,646,156

DATED : 7/8/97

INVENTOR(S) : Marlene A. Jacobson, Robert G. Johnson and Christopher A. Salvatore It is certified that error appears in the above-identified patent and that said Letters Patent is hereby corrected as shown below:

Column 72, line 25 please delete " intimation" and insert -- inflammation --.

Signed and Sealed this

Seventeenth Day of March, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
ATTCGCAGCC ACGTCCTGAG GCGGCGGGAG CCCTTCAAAG CAGGTGGCAC CAGTGCCCGC        60
```

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

GCGGAGGCTG ATCTGCTCTC CATCACTGCC ATGAGCTGCC AAGGCGCGGG CACTGGTGCC 60

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

TCCAGAAGTT CCGGGTCACC TTCCTTAAGA TCTGGAATGA CCACTTCCGC TGCCAGCCCA 60

( 2 ) INFORMATION FOR SEQ ID NO:4:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

AGTCGTGGGG CGCCTCCTCT GGGGGGTCCT CGTCGACGGG GGGCGTGGGC TGGCAGCGGA 60

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

GCCTCTTTGA GGATGTGGTC CCCATGAACT ACATGGTGTA CTTCA 45

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

GCAGGGGCAC CAGCACACAG GCAAAGAAGT TGAAGTACAC CATGT 45

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

TCGCGCCGCC AGGAAGAT 18

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

TATATTGAAT TCTAGACACC CAGCATGAGC 30

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

TCAATGGCGA TGGCCAGG 18

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

TATATTGAAT TCATGGAGCT CTGCGTGAGG  30

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

GTAGACCATG TACTCCAT  18

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

TATATTGAAT TCTGACCTTC TCGAACTCGC  30

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

ATTGAATTCG ATCACGGGCT CCCCCATGC  29

(2) INFORMATION FOR SEQ ID NO:14:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

ATGGAGTACA TGGTCTACTT CAACTTCTTT GTGTGGGTGC TGCCCCCGCT  50

( 2 ) INFORMATION FOR SEQ ID NO:15:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

GAAGATCCGC AAATAGACAC CCAGCATGAG CAGAAGCGGG GGCAGCACCC     50

( 2 ) INFORMATION FOR SEQ ID NO:16:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

CCCTCTAGAG CCCAGCCTGT GCCCGCCATG CCCATCATGG GCTCC     45

( 2 ) INFORMATION FOR SEQ ID NO:17:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

CCCACCTTTT GAGCAAGTTC     20

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

GGCTTATGAG TATTTCTTCC     20

( 2 ) INFORMATION FOR SEQ ID NO:19:

( i ) SEQUENCE CHARACTERISTICS:
    ( A ) LENGTH: 326 amino acids (B) TYPE: amino acid
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:19:

```
Met Pro Pro Ser Ile Ser Ala Phe Gln Ala Ala Tyr Ile Gly Ile Glu
1               5                   10                  15
Val Leu Ile Ala Leu Val Ser Val Pro Gly Asn Val Leu Val Ile Trp
                20                  25                  30
Ala Val Lys Val Asn Gln Ala Leu Arg Asp Ala Thr Phe Cys Phe Ile
            35                  40                  45
Val Ser Leu Ala Val Ala Asp Val Ala Val Gly Ala Leu Val Ile Pro
    50                  55                  60
Leu Ala Ile Leu Ile Asn Ile Gly Pro Gln Thr Tyr Phe His Thr Cys
65                  70                  75                  80
Leu Met Val Ala Cys Pro Val Leu Ile Leu Thr Gln Ser Ser Ile Leu
                85                  90                  95
Ala Leu Leu Ala Ile Ala Val Asp Arg Tyr Leu Arg Val Lys Ile Pro
            100                 105                 110
Leu Arg Tyr Lys Met Val Val Thr Pro Arg Arg Ala Ala Val Ala Ile
        115                 120                 125
Ala Gly Cys Trp Ile Leu Ser Phe Val Val Gly Leu Thr Pro Met Phe
    130                 135                 140
Gly Trp Asn Asn Leu Ser Ala Val Glu Arg Ala Trp Ala Ala Asn Gly
145                 150                 155                 160
Ser Met Gly Glu Pro Val Ile Lys Cys Glu Phe Glu Lys Val Ile Ser
                165                 170                 175
Met Glu Tyr Met Val Tyr Phe Asn Phe Phe Val Trp Val Leu Pro Pro
            180                 185                 190
Leu Leu Leu Met Val Leu Ile Tyr Leu Glu Val Phe Tyr Leu Ile Arg
        195                 200                 205
Lys Gln Leu Asn Lys Lys Val Ser Ala Ser Ser Gly Asp Pro Gln Lys
    210                 215                 220
Tyr Tyr Gly Lys Glu Leu Lys Ile Ala Lys Ser Leu Ala Leu Ile Leu
225                 230                 235                 240
Phe Leu Phe Ala Leu Ser Trp Leu Pro Leu His Ile Leu Asn Cys Ile
                245                 250                 255
Thr Leu Phe Cys Pro Ser Cys His Lys Pro Ser Ile Leu Thr Tyr Ile
            260                 265                 270
Ala Ile Phe Leu Thr His Gly Asn Ser Ala Met Asn Pro Ile Val Tyr
        275                 280                 285
Ala Phe Arg Ile Gln Lys Phe Arg Val Thr Phe Leu Lys Ile Trp Asn
    290                 295                 300
Asp His Phe Arg Cys Gln Pro Ala Pro Pro Ile Asp Glu Asp Leu Pro
305                 310                 315                 320
Glu Glu Arg Pro Asp Asp
                325
```

(2) INFORMATION FOR SEQ ID NO:20:

(i) SEQUENCE CHARACTERISTICS:

(A) LENGTH: 981 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

| | | | | | | |
|---|---|---|---|---|---|---|
| ATGCCGCCCT | CCATCTCAGC | TTTCCAGGCC | GCCTACATCG | GCATCGAGGT | GCTCATCGCC | 60 |
| CTGGTCTCTG | TGCCCGGGAA | CGTGCTGGTG | ATCTGGGCGG | TGAAGGTGAA | CCAGGCGCTG | 120 |
| CGGGATGCCA | CCTTCTGCTT | CATCGTGTCG | CTGGCGGTGG | CTGATGTGGC | CGTGGGTGCC | 180 |
| CTGGTCATCC | CCCTCGCCAT | CCTCATCAAC | ATTGGGCCAC | AGACCTACTT | CCACACCTGC | 240 |
| CTCATGGTTG | CCTGTCCGGT | CCTCATCCTC | ACCCAGAGCT | CCATCCTGGC | CTGCTGGCA | 300 |
| ATTGCTGTGG | ACCGCTACCT | CCGGGTCAAG | ATCCCTCTCC | GGTACAAGAT | GGTGGTGACC | 360 |
| CCCCGGAGGG | CGGCGGTGGC | CATAGCCGGC | TGCTGGATCC | TCTCCTTCGT | GGTGGGACTG | 420 |
| ACCCCTATGT | TTGGCTGGAA | CAATCTGAGT | GCGGTGGAGC | GGGCCTGGGC | AGCCAACGGC | 480 |
| AGCATGGGGG | AGCCCGTGAT | CAAGTGCGAG | TTCGAGAAGG | TCATCAGCAT | GGAGTACATG | 540 |
| GTCTACTTCA | ACTTCTTTGT | GTGGGTGCTG | CCCCCGCTTC | TCCTCATGGT | CCTCATCTAC | 600 |
| CTGGAGGTCT | TCTACCTAAT | CCGCAAGCAG | CTCAACAAGA | AGGTGTCGGC | CTCCTCCGGC | 660 |
| GACCCGCAGA | AGTACATGG | GAAGGAGCTG | AAGATCGCCA | AGTCGCTGGC | CCTCATCCTC | 720 |
| TTCCTCTTTG | CCCTCAGCTG | GCTGCCTTTG | CACATCCTCA | ACTGCATCAC | CCTCTTCTGC | 780 |
| CCGTCCTGCC | ACAAGCCCAG | CATCCTTACC | TACATTGCCA | TCTTCCTCAC | GCACGGCAAC | 840 |
| TCGGCCATGA | ACCCCATTGT | CTATGCCTTC | CGCATCCAGA | AGTTCCGCGT | CACCTTCCTT | 900 |
| AAGATTTGGA | ATGACCATTT | CCGCTGCCAG | CCTGCACCTC | CCATTGACGA | GGATCTCCCA | 960 |
| GAAGAGAGGC | CTGATGACTA | G | | | | 981 |

(2) INFORMATION FOR SEQ ID NO:21:

(i) SEQUENCE CHARACTERISTICS:
(A) LENGTH: 412 amino acids
(B) TYPE: amino acid
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:21:

```
Met Pro Ile Met Gly Ser Ser Val Tyr Ile Thr Val Glu Leu Ala Ile
 1               5                  10                  15

Ala Val Leu Ala Ile Leu Gly Asn Val Leu Val Cys Trp Ala Val Trp
                20                  25                  30

Leu Asn Ser Asn Leu Gln Asn Val Thr Asn Tyr Phe Val Val Ser Leu
            35                  40                  45

Ala Ala Ala Asp Ile Ala Val Gly Val Leu Ala Ile Pro Phe Ala Ile
        50                  55                  60

Thr Ile Ser Thr Gly Phe Cys Ala Ala Cys His Gly Cys Leu Phe Ile
65                  70                  75                  80
```

| | | | | | | | | | | | | | | | |
|---|---|---|---|---|---|---|---|---|---|---|---|---|---|---|---|
|Ala|Cys|Phe|Val|Leu 85|Val|Leu|Thr|Gln|Ser 90|Ser|Ile|Phe|Ser|Leu 95|Leu|
|Ala|Ile|Ala|Ile 100|Asp|Arg|Tyr|Ile|Ala 105|Ile|Arg|Ile|Pro|Leu 110|Arg|Tyr|
|Asn|Gly|Leu 115|Val|Thr|Gly|Thr|Arg 120|Ala|Lys|Gly|Ile|Ile 125|Ala|Ile|Cys|
|Trp|Val 130|Leu|Ser|Phe|Ala|Ile 135|Gly|Leu|Thr|Pro|Met 140|Leu|Gly|Trp|Asn|
|Asn 145|Cys|Gly|Gln|Pro|Lys 150|Glu|Gly|Lys|Asn|His 155|Ser|Gln|Gly|Cys|Gly 160|
|Glu|Gly|Gln|Val|Ala 165|Cys|Leu|Phe|Glu|Asp 170|Val|Val|Pro|Met|Asn 175|Tyr|
|Met|Val|Tyr|Phe 180|Asn|Phe|Phe|Ala|Cys 185|Val|Leu|Val|Pro|Leu 190|Leu|Leu|
|Met|Leu|Gly 195|Val|Tyr|Leu|Arg|Ile 200|Phe|Leu|Ala|Ala|Arg 205|Arg|Gln|Leu|
|Lys|Gln 210|Met|Glu|Ser|Gln|Pro 215|Leu|Pro|Gly|Glu|Arg 220|Ala|Arg|Ser|Thr|
|Leu 225|Gln|Lys|Glu|Val|His 230|Ala|Ala|Lys|Ser|Leu 235|Ala|Ile|Ile|Val|Gly 240|
|Leu|Phe|Ala|Leu|Cys 245|Trp|Leu|Pro|Leu|His 250|Ile|Ile|Asn|Cys|Phe 255|Thr|
|Phe|Phe|Cys|Pro 260|Asp|Cys|Ser|His|Ala 265|Pro|Leu|Trp|Leu|Met 270|Tyr|Leu|
|Ala|Ile|Val 275|Leu|Ser|His|Thr|Asn 280|Ser|Val|Val|Asn|Pro 285|Phe|Ile|Tyr|
|Ala|Tyr 290|Arg|Ile|Arg|Glu|Phe 295|Arg|Gln|Thr|Phe|Arg 300|Lys|Ile|Ile|Arg|
|Ser 305|His|Val|Leu|Arg|Gln 310|Gln|Glu|Pro|Phe|Lys 315|Ala|Ala|Gly|Thr|Ser 320|
|Ala|Arg|Val|Leu|Ala 325|Ala|His|Gly|Ser|Asp 330|Gly|Glu|Gln|Val|Ser 335|Leu|
|Arg|Leu|Asn|Gly 340|His|Pro|Pro|Gly|Val 345|Trp|Ala|Asn|Gly|Ser 350|Ala|Pro|
|His|Pro|Glu 355|Arg|Arg|Pro|Asn|Gly 360|Tyr|Ala|Leu|Gly|Leu 365|Val|Ser|Gly|
|Gly|Ser 370|Ala|Gln|Glu|Ser|Gln 375|Gly|Asn|Thr|Gly|Leu 380|Pro|Asp|Val|Glu|
|Leu 385|Leu|Ser|His|Glu|Leu 390|Lys|Gly|Val|Cys|Pro 395|Glu|Pro|Pro|Gly|Leu 400|
|Asp|Asp|Pro|Leu|Ala 405|Gln|Asp|Gly|Ala|Gly 410|Val|Ser| | | | |

( 2 ) INFORMATION FOR SEQ ID NO:22:

( i ) SEQUENCE CHARACTERISTICS:
        ( A ) LENGTH: 1239 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

| | | | | | |
|---|---|---|---|---|---|
| ATGCCCATCA | TGGGCTCCTC | GGTGTACATC | ACGGTGGAGC | TGGCCATTGC | TGTGCTGGCC | 60 |
| ATCCTGGGCA | ATGTGCTGGT | GTGCTGGGCC | GTGTGGCTCA | ACAGCAACCT | GCAGAACGTC | 120 |
| ACCAACTACT | TTGTGGTGTC | ACTGGCGGCG | GCCGACATCG | CAGTGGGTGT | GCTCGCCATC | 180 |
| CCCTTTGCCA | TCACCATCAG | CACCGGGTTC | TGCGCTGCCT | GCCACGGCTG | CCTCTTCATT | 240 |
| GCCTGCTTCG | TCCTGGTCCT | CACGCAGAGC | TCCATCTTCA | GTCTCCTGGC | CATCGCCATT | 300 |
| GACCGCTACA | TTGCCATCCG | CATCCCGCTC | CGGTACAATG | GCTTGGTGAC | CGGCACGAGG | 360 |
| GCTAAGGGCA | TCATTGCCAT | CTGCTGGGTG | CTGTCGTTTG | CCATCGGCCT | GACTCCCATG | 420 |
| CTAGGTTGGA | ACAACTGCGG | TCAGCCAAAG | GAGGGCAAGA | ACCACTCCCA | GGGCTGCGGG | 480 |
| GAGGGCCAAG | TGGCCTGTCT | CTTTGAGGAT | GTGGTCCCCA | TGAACTACAT | GGTGTACTTC | 540 |
| AACTTCTTTG | CCTGTGTGCT | GGTGCCCCTG | CTGCTCATGC | TGGGTGTCTA | TTTGCGGATC | 600 |
| TTCCTGGCGG | CGCGACGACA | GCTGAAGCAG | ATGGAGAGCC | AGCCTCTGCC | GGGGGAGCGG | 660 |
| GCACGGTCCA | CACTGCAGAA | GGAGGTCCAT | GCTGCCAAGT | CACTGGCCAT | CATTGTGGGG | 720 |
| CTCTTTGCCC | TCTGCTGGCT | GCCCCTACAC | ATCATCAACT | GCTTCACTTT | CTTCTGCCCC | 780 |
| GACTGCAGCC | ACGCCCCTCT | CTGGCTCATG | TACCTGGCCA | TCGTCCTCTC | CCACACCAAT | 840 |
| TCGGTTGTGA | ATCCCTTCAT | CTACGCCTAC | CGTATCCGCG | AGTTCCGCCA | GACCTTCCGC | 900 |
| AAGATCATTC | GCAGCCACGT | CCTGAGGCAG | CAAGAACCTT | TCAAGGCAGC | TGGCACCAGT | 960 |
| GCCCGGGTCT | TGGCAGCTCA | TGGCAGTGAC | GGAGAGCAGG | TCAGCCTCCG | TCTCAACGGC | 1020 |
| CACCCGCCAG | GAGTGTGGGC | CAACGGCAGT | GCTCCCCACC | CTGAGCGGAG | GCCCAATGGC | 1080 |
| TATGCCCTGG | GGCTGGTGAG | TGGAGGGAGT | GCCCAAGAGT | CCCAGGGGAA | CACGGGCCTC | 1140 |
| CCAGACGTGG | AGCTCCTTAG | CCATGAGCTC | AAGGGAGTGT | GCCCAGAGCC | CCCTGGCCTA | 1200 |
| GATGACCCCC | TGGCCCAGGA | TGGAGCAGGA | GTGTCCTGA | | | 1239 |

( 2 ) INFORMATION FOR SEQ ID NO:23:

( i ) SEQUENCE CHARACTERISTICS:
        ( A ) LENGTH: 332 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Modified-site
        ( B ) LOCATION: 216
        ( D ) OTHER INFORMATION: /label=threonine ( x i ) SEQUENCE DESCRIPTION: SEQ ID NO:23:

| Met | Leu | Leu | Glu | Thr | Gln | Asp | Ala | Leu | Tyr | Val | Ala | Leu | Glu | Leu | Val |
|---|---|---|---|---|---|---|---|---|---|---|---|---|---|---|---|
| 1 | | | | 5 | | | | | 10 | | | | | 15 | |

| Ile | Ala | Ala | Leu | Ser | Val | Ala | Gly | Asn | Val | Leu | Val | Cys | Ala | Ala | Val |
|---|---|---|---|---|---|---|---|---|---|---|---|---|---|---|---|
| | | | 20 | | | | | 25 | | | | | 30 | | |

| Gly | Thr | Ala | Asn | Thr | Leu | Gln | Thr | Pro | Thr | Asn | Tyr | Phe | Leu | Val | Ser |
|---|---|---|---|---|---|---|---|---|---|---|---|---|---|---|---|
| | | 35 | | | | 40 | | | | | 45 | | | | |

| Leu | Ala | Ala | Ala | Asp | Val | Ala | Val | Gly | Leu | Phe | Ala | Ile | Pro | Phe | Ala |
|---|---|---|---|---|---|---|---|---|---|---|---|---|---|---|---|
| | 50 | | | | | 55 | | | | | 60 | | | | |

| Ile | Thr | Ile | Ser | Leu | Gly | Phe | Cys | Thr | Asp | Phe | Tyr | Gly | Cys | Leu | Phe |
|---|---|---|---|---|---|---|---|---|---|---|---|---|---|---|---|
| 65 | | | | | 70 | | | | | 75 | | | | | 80 |

| | | | | | | | | | | | | | | |
|---|---|---|---|---|---|---|---|---|---|---|---|---|---|---|
| Leu | Ala | Cys | Phe | Val 85 | Leu | Val | Leu | Thr | Gln 90 | Ser | Ser | Ile | Phe | Ser 95 | Leu |
| Leu | Ala | Val | Ala 100 | Val | Asp | Arg | Tyr | Leu 105 | Ala | Ile | Cys | Val | Pro 110 | Leu | Arg |
| Tyr | Lys | Ser 115 | Leu | Val | Thr | Gly 120 | Thr | Arg | Ala | Arg | Gly 125 | Val | Ile | Ala | Val |
| Leu | Trp 130 | Val | Leu | Ala | Phe 135 | Gly | Ile | Gly | Leu | Thr 140 | Pro | Phe | Leu | Gly | Trp |
| Asn 145 | Ser | Lys | Asp | Ser | Ala 150 | Thr | Asn | Asn | Cys | Thr 155 | Glu | Pro | Trp | Asp | Gly 160 |
| Thr | Thr | Asn | Glu | Ser 165 | Cys | Cys | Leu | Val | Lys 170 | Cys | Leu | Phe | Glu | Asn 175 | Val |
| Val | Pro | Met | Ser 180 | Tyr | Met | Val | Tyr | Phe 185 | Asn | Phe | Phe | Gly | Cys 190 | Val | Leu |
| Pro | Pro | Leu 195 | Leu | Ile | Met | Leu | Val 200 | Ile | Tyr | Ile | Lys | Ile 205 | Phe | Leu | Val |
| Ala | Cys 210 | Arg | Gln | Leu | Gln | Arg 215 | Xaa | Glu | Leu | Met | Asp 220 | His | Ser | Arg | Thr |
| Thr 225 | Leu | Gln | Arg | Glu | Ile 230 | His | Ala | Ala | Lys | Ser 235 | Leu | Ala | Met | Ile | Val 240 |
| Gly | Ile | Phe | Ala | Leu 245 | Cys | Trp | Leu | Pro | Val 250 | His | Ala | Val | Asn | Cys 255 | Val |
| Thr | Leu | Phe | Gln 260 | Pro | Ala | Gln | Gly | Lys 265 | Asn | Lys | Pro | Lys | Trp 270 | Ala | Met |
| Asn | Met | Ala 275 | Ile | Leu | Leu | Ser | His 280 | Ala | Asn | Ser | Val | Val 285 | Asn | Pro | Ile |
| Val | Tyr 290 | Ala | Tyr | Arg | Asn | Arg 295 | Asp | Phe | Arg | Tyr | Thr 300 | Phe | His | Lys | Ile |
| Ile 305 | Ser | Arg | Tyr | Leu | Leu 310 | Cys | Gln | Ala | Asp | Val 315 | Lys | Ser | Gly | Asn | Gly 320 |
| Gln | Ala | Gly | Val | Gln 325 | Pro | Ala | Leu | Gly | Val 330 | Gly | Leu | | | | |

(2) INFORMATION FOR SEQ ID NO:24:

( i ) SEQUENCE CHARACTERISTICS:
  ( A ) LENGTH: 999 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:24:

```
ATGCTGCTGG AGACACAGGA CGCGCTGTAC GTGGCGCTGG AGCTGGTCAT CGCCGCGCTT    60
TCGGTGGCGG GCAACGTGCT GGTGTGCGCC GCGGTGGGCA CGGCGAACAC TCTGCAGACG   120
CCCACCAACT ACTTCCTGGT GTCCCTGGCT GCGGCCGACG TGGCCGTGGG GCTCTTCGCC   180
ATCCCCTTTG CCATCACCAT CAGCCTGGGC TTCTGCACTG ACTTCTACGG CTGCCTCTTC   240
CTCGCCTGCT TCGTGCTGGT GCTCACGCAG AGCTCCATCT TCAGCCTTCT GGCCGTGGCA   300
GTCGACAGAT ACCTGGCCAT CTGTGTCCCG CTCAGGTATA AAGTTTGGT CACGGGGACC    360
CGAGCAAGAG GGGTCATTGC TGTCCTCTGG GTCCTTGCCT TGGCATCGG ATTGACTCCA    420
TTCCTGGGGT GGAACAGTAA AGACAGTGCC ACCAACAACT GCACAGAACC CTGGGATGGA   480
```

-continued

```
ACCACGAATG AAAGCTGCTG CCTTGTGAAG TGTCTCTTTG AGAATGTGGT CCCCATGAGC      540

TACATGGTAT ATTTCAATTT CTTTGGGTGT GTTCTGCCCC CACTGCTTAT AATGCTGGTG      600

ATCTACATTA AGATCTTCCT GGTGGCCTGC AGGCAGCTTC AGCGCACTGA GCTGATGGAC      660

CACTCGAGGA CCACCCTCCA GCGGGAGATC CATGCAGCCA AGTCACTGGC CATGATTGTG      720

GGGATTTTTG CCCTGTGCTG GTTACCTGTG CATGCTGTTA ACTGTGTCAC TCTTTTCCAG      780

CCAGCTCAGG GTAAAAATAA GCCCAAGTGG GCAATGAATA TGGCCATTCT TCTGTCACAT      840

GCCAATTCAG TTGTCAATCC CATTGTCTAT GCTTACCGGA ACCGAGACTT CCGCTACACT      900

TTTCACAAAA TTATCTCCAG GTATCTTCTC TGCCAAGCAG ATGTCAAGAG TGGGAATGGT      960

CAGGCTGGGG TACAGCCTGC TCTCGGTGTG GGCCTATGA                             999
```

(2) INFORMATION FOR SEQ ID NO:25:

(i) SEQUENCE CHARACTERISTICS:
        (A) LENGTH: 318 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:25:

```
Met Pro Asn Asn Ser Thr Ala Leu Ser Leu Ala Asn Val Thr Tyr Ile
 1               5                  10                  15

Thr Met Glu Ile Phe Ile Gly Leu Cys Ala Ile Val Gly Asn Val Leu
            20                  25                  30

Val Ile Cys Val Val Lys Leu Asn Pro Ser Leu Gln Thr Thr Thr Phe
        35                  40                  45

Tyr Phe Ile Val Ser Leu Ala Leu Ala Asp Ile Ala Val Gly Val Leu
    50                  55                  60

Val Met Pro Leu Ala Ile Val Val Ser Leu Gly Ile Thr Ile His Phe
65                  70                  75                  80

Tyr Ser Cys Leu Phe Met Thr Cys Leu Leu Leu Ile Phe Thr His Ala
                85                  90                  95

Ser Ile Met Ser Leu Leu Ala Ile Ala Val Asp Arg Tyr Leu Arg Val
               100                 105                 110

Lys Leu Thr Val Arg Tyr Lys Arg Val Thr Thr His Arg Arg Ile Trp
           115                 120                 125

Leu Ala Leu Gly Leu Cys Trp Leu Val Ser Phe Leu Val Gly Leu Thr
       130                 135                 140

Pro Met Phe Gly Trp Asn Met Lys Leu Thr Ser Glu Tyr His Arg Asn
145                 150                 155                 160

Val Thr Phe Leu Ser Cys Gln Phe Val Ser Val Met Arg Met Asp Tyr
                165                 170                 175

Met Val Tyr Phe Ser Phe Leu Thr Trp Ile Phe Ile Pro Leu Val Val
               180                 185                 190

Met Cys Ala Ile Tyr Leu Asp Ile Phe Tyr Ile Ile Arg Asn Lys Leu
           195                 200                 205

Ser Leu Asn Leu Ser Asn Ser Lys Glu Thr Gly Ala Phe Tyr Gly Arg
       210                 215                 220

Glu Phe Lys Thr Ala Lys Ser Leu Phe Leu Val Leu Phe Leu Phe Ala
```

```
                225                     230                     235                     240

Leu  Ser  Trp  Leu  Pro  Leu  Ser  Ile  Ile  Asn  Cys  Ile  Ile  Tyr  Phe  Asn
                            245                      250                     255

Gly  Glu  Val  Pro  Gln  Leu  Val  Leu  Tyr  Met  Gly  Ile  Leu  Leu  Ser  His
                            260                      265                     270

Ala  Asn  Ser  Met  Met  Asn  Pro  Ile  Val  Tyr  Ala  Tyr  Lys  Ile  Lys  Lys
                  275                           280                     285

Phe  Lys  Glu  Thr  Tyr  Leu  Leu  Ile  Leu  Lys  Ala  Cys  Val  Val  Cys  His
                  290                           295                     300

Pro  Ser  Asp  Ser  Leu  Asp  Thr  Ser  Ile  Glu  Lys  Asn  Ser  Glu
        305                           310                      315
```

( 2 ) INFORMATION FOR SEQ ID NO:26:

( i ) SEQUENCE CHARACTERISTICS:
        ( A ) LENGTH: 957 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

```
ATGCCCAACA  ACAGCACTGC  TCTGTCATTG  GCCAATGTTA  CCTACATCAC  CATGGAAATT      60
TTCATTGGAC  TCTGCGCCAT  AGTGGGCAAC  GTGCTGGTCA  TCTGCGTGGT  CAAGCTGAAC     120
CCCAGCCTGC  AGACCACCAC  CTTCTATTTC  ATTGTCTCTC  TAGCCCTGGC  TGACATTGCT     180
GTTGGGGTGC  TGGTCATGCC  TTTGGCCATT  GTTGTCAGCC  TGGGCATCAC  AATCCACTTC     240
TACAGCTGCC  TTTTTATGAC  TTGCCTACTG  CTTATCTTTA  CCCACGCCTC  CATCATGTCC     300
TTGCTGGCCA  TCGCTGTGGA  CCGATACTTG  CGGGTCAAGC  TTACCGTCAG  ATACAAGAGG     360
GTCACCACTC  ACAGAAGAAT  ATGGCTGGCC  CTGGGCCTTT  GCTGGCTGGT  GTCATTCCTG     420
GTGGGATTGA  CCCCCATGTT  TGGCTGGAAC  ATGAAACTGA  CCTCAGAGTA  CCACAGAAAT     480
GTCACCTTCC  TTTCATGCCA  ATTTGTTTCC  GTCATGAGAA  TGGACTACAT  GGTATACTTC     540
AGCTTCCTCA  CCTGGATTTT  CATCCCCCTG  GTTGTCATGT  GCGCCATCTA  TCTTGACATC     600
TTTTACATCA  TTCGGAACAA  ACTCAGTCTG  AACTTATCTA  ACTCCAAAGA  GACAGGTGCA     660
TTTTATGGAC  GGGAGTTCAA  GACGGCTAAG  TCCTTGTTTC  TGGTTCTTTT  CTTGTTTGCT     720
CTGTCATGGC  TGCCTTTATC  TATCATCAAC  TGCATCATCT  ACTTTAATGG  TGAGGTACCA     780
CAGCTTGTGC  TGTACATGGG  CATCCTGCTG  TCCCATGCCA  ACTCCATGAT  GAACCCTATC     840
GTCTATGCCT  ATAAAATAAA  GAAGTTCAAG  GAAACCTACC  TTTTGATCCT  CAAAGCCTGT     900
GTGGTCTGCC  ATCCCTCTGA  TTCTTTGGAC  ACAAGCATTG  AGAAGAATTC  TGAGTAG       957
```

( 2 ) INFORMATION FOR SEQ ID NO:27:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:27:

CCCAAGCTTA TGAAAGCCAA CAATACC 27

( 2 ) INFORMATION FOR SEQ ID NO:28:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:28:

TGCTCTAGAC TCTGGTATCT TCACATT 27

( 2 ) INFORMATION FOR SEQ ID NO:29:

( i ) SEQUENCE CHARACTERISTICS:
  ( A ) LENGTH: 45 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:29:

GCCTCTTTGA GGATGTGGTC CCCATGAACT ACATGGTGTA CTTCA 45

( 2 ) INFORMATION FOR SEQ ID NO:30:

( i ) SEQUENCE CHARACTERISTICS:
  ( A ) LENGTH: 45 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:30:

GCAGGGGCAC CAGCACACAG GCAAAGAAGT TGAAGTACAC CATGT 45

( 2 ) INFORMATION FOR SEQ ID NO:31:

( i ) SEQUENCE CHARACTERISTICS:
  ( A ) LENGTH: 18 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:31:

TCACCATCTT CCAGGAGC 18

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:32:

ACTCCTTGGA GGCCATGT                                                  18

( 2 ) INFORMATION FOR SEQ ID NO:33:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:33:

TCCTGCACCA CCAACTGCTT AGCCCCCTG GCCAAGGTCA TCCAT       45

( 2 ) INFORMATION FOR SEQ ID NO:34:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:34:

CATGAGCCCT TCCACGATGC CAAAGTTGTC ATGGATGACC TTGGC       45

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:35:

GTTACCTACA TCACCATG                                                 18

( 2 ) INFORMATION FOR SEQ ID NO:36:

(i) SEQUENCE CHARACTERISTICS:
 (A) LENGTH: 18 base pairs
 (B) TYPE: nucleic acid
 (C) STRANDEDNESS: both
 (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:36:

GTTAGATAAG TTCAGACT　　　　　　　　　　　　　　　　　　　　　　　　18

(2) INFORMATION FOR SEQ ID NO:37:

(i) SEQUENCE CHARACTERISTICS:
 (A) LENGTH: 45 base pairs
 (B) TYPE: nucleic acid
 (C) STRANDEDNESS: both
 (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:37:

CTGACCTCAG AGTACCACAG AAATGTCACC TTCCTTTCAT GCCAA　　　　　　45

(2) INFORMATION FOR SEQ ID NO:38:

(i) SEQUENCE CHARACTERISTICS:
 (A) LENGTH: 45 base pairs
 (B) TYPE: nucleic acid
 (C) STRANDEDNESS: both
 (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:38:

TTGGCATGAA AGGAAGGTGA CATTTCTGTG GTACTCTGAG GTCAG　　　　　　45

(2) INFORMATION FOR SEQ ID NO:39:

(i) SEQUENCE CHARACTERISTICS:
 (A) LENGTH: 46 base pairs
 (B) TYPE: nucleic acid
 (C) STRANDEDNESS: both
 (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:39:

CTCAGTCTGA ACTTATCTAA CTCCAAAGAG ACAGGTGCAT TTTATG　　　　　46

(2) INFORMATION FOR SEQ ID NO:40:

(i) SEQUENCE CHARACTERISTICS:
 (A) LENGTH: 46 base pairs
 (B) TYPE: nucleic acid
 (C) STRANDEDNESS: both ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:40:

CATAAAATGC ACCTGTCTCT TTGGAGTTAG ATAAGTTCAG ACTGAG     46

( 2 ) INFORMATION FOR SEQ ID NO:41:

( i ) SEQUENCE CHARACTERISTICS:
            ( A ) LENGTH: 18 base pairs
            ( B ) TYPE: nucleic acid
            ( C ) STRANDEDNESS: both
            ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:41:

TCCTCGGTGT ACATCACG     18

( 2 ) INFORMATION FOR SEQ ID NO:42:

( i ) SEQUENCE CHARACTERISTICS:
            ( A ) LENGTH: 18 base pairs
            ( B ) TYPE: nucleic acid
            ( C ) STRANDEDNESS: both
            ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:42:

TCCATCTGCT TCAGCTGT     18

( 2 ) INFORMATION FOR SEQ ID NO:43:

( i ) SEQUENCE CHARACTERISTICS:
            ( A ) LENGTH: 45 base pairs
            ( B ) TYPE: nucleic acid
            ( C ) STRANDEDNESS: both
            ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:43:

CTGGGCCTTT GCTGGCTGGT GTCATTCCTG GTGGGATTGA CCCCC     45

( 2 ) INFORMATION FOR SEQ ID NO:44:

( i ) SEQUENCE CHARACTERISTICS:
            ( A ) LENGTH: 45 base pairs
            ( B ) TYPE: nucleic acid
            ( C ) STRANDEDNESS: both
            ( D ) TOPOLOGY: linear ( i i ) MOLECULE TYPE: cDNA (i i i) HYPOTHETICAL: NO (i v) ANTI-SENSE: YES (x i) SEQUENCE DESCRIPTION: SEQ ID NO:44:

TGAGGTCAGT TTCATGTTCC AGCCAAACAT GGGGGTCAAT CCCAC                  45

(2) INFORMATION FOR SEQ ID NO:45:

(i) SEQUENCE CHARACTERISTICS:
   (A) LENGTH: 20 base pairs
   (B) TYPE: nucleic acid
   (C) STRANDEDNESS: both
   (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:45:

ATGCTGCTGG AGACACAGGA                                              20

(2) INFORMATION FOR SEQ ID NO:46:

(i) SEQUENCE CHARACTERISTICS:
   (A) LENGTH: 19 base pairs
   (B) TYPE: nucleic acid
   (C) STRANDEDNESS: both
   (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:46:

TGGTCCATCA GCTCAGTGC                                               19

(2) INFORMATION FOR SEQ ID NO:47:

(i) SEQUENCE CHARACTERISTICS:
   (A) LENGTH: 60 base pairs
   (B) TYPE: nucleic acid
   (C) STRANDEDNESS: both
   (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:47:

GGTGGAACAG TAAAGACAGT GCCACCAACA ACTGCACAGA ACCCTGGGAT GGAACCACGA   60

(2) INFORMATION FOR SEQ ID NO:48:

(i) SEQUENCE CHARACTERISTICS:
   (A) LENGTH: 60 base pairs
   (B) TYPE: nucleic acid
   (C) STRANDEDNESS: both
   (D) TOPOLOGY: linear (i i) MOLECULE TYPE: cDNA (i i i) HYPOTHETICAL: NO (i v) ANTI-SENSE: YES ( x i ) SEQUENCE DESCRIPTION: SEQ ID NO:48:

GGACCACATT CTCAAAGAGA CACTTCACAA GGCAGCAGCT TTCATTCGTG GTTCCATCCC    60

( 2 ) INFORMATION FOR SEQ ID NO:49:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:49:

CTACATCGGC ATCGAGGT    18

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:50:

GAACTCGCAC TTGATCAC    18

( 2 ) INFORMATION FOR SEQ ID NO:51:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: both ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:51:

TGGTGGGACT GACCCCTATG TTTGGCTGGA ACAATCTGAG TGCGG    45

( 2 ) INFORMATION FOR SEQ ID NO:52:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:52:

TGCTGCCGTT GGCTGCCCAG GCCCGCTCCA CCGCACTCAG ATTGT    45

( 2 ) INFORMATION FOR SEQ ID NO:53:

( i ) SEQUENCE CHARACTERISTICS:
    ( A ) LENGTH: 42 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:53:

CTGAGCTCAG CAGACGAAAA CCTCACCTTC CTACCCTGCC GA    42

( 2 ) INFORMATION FOR SEQ ID NO:54:

( i ) SEQUENCE CHARACTERISTICS:
    ( A ) LENGTH: 42 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:54:

TCGGCAGGGT AGGAAGGTGA GGTTTTCGTC TGCTGAGCTC AG    42

( 2 ) INFORMATION FOR SEQ ID NO:55:

( i ) SEQUENCE CHARACTERISTICS:
    ( A ) LENGTH: 46 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:55:

CTCAGCCAGA GCTTTTCTGG CTCCAGAGAG ACAGGCGCAT TCTATG    46

( 2 ) INFORMATION FOR SEQ ID NO:56:

( i ) SEQUENCE CHARACTERISTICS:
    ( A ) LENGTH: 46 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:56:

CATAGAATGC GCCTGTCTCT CTGGAGCCAG AAAAGCTCTG GCTGAG    46